(12) United States Patent
Fei et al.

(10) Patent No.: US 12,138,262 B2
(45) Date of Patent: Nov. 12, 2024

(54) PROCESS OF MANUFACTURE OF A COMPOUND FOR INHIBITING THE ACTIVITY OF SHP2, AS WELL AS PRODUCTS RESULTING FROM ACID ADDITION

(71) Applicant: Novartis AG, Basel (CH)

(72) Inventors: Zhongbo Fei, Shanghai (CN); Gang Lu, Changshu (CN); Yinbo Wan, Changshu (CN); Jianhua Wang, Changshu (CN); Quanbing Wu, Changshu (CN); Hao Zhang, Changshu (CN)

(73) Assignee: NOVARTIS AG, Basel (CH)

( * ) Notice: Subject to any disclaimer, the term of this patent is extended or adjusted under 35 U.S.C. 154(b) by 697 days.

(21) Appl. No.: 17/280,637

(22) PCT Filed: Sep. 18, 2019

(86) PCT No.: PCT/IB2019/057864
§ 371 (c)(1),
(2) Date: Mar. 26, 2021

(87) PCT Pub. No.: WO2020/065453
PCT Pub. Date: Apr. 2, 2020

(65) Prior Publication Data
US 2021/0346375 A1 Nov. 11, 2021

(30) Foreign Application Priority Data
Sep. 29, 2018 (WO) ................ PCT/CN2018/108739

(51) Int. Cl.
*A61K 31/497* (2006.01)
*A61K 45/06* (2006.01)
(Continued)

(52) U.S. Cl.
CPC ............ *A61K 31/497* (2013.01); *A61K 45/06* (2013.01); *C07D 491/107* (2013.01); *C07B 2200/13* (2013.01)

(58) Field of Classification Search
CPC .... A61K 31/497; A61K 45/06; A61K 31/438; A61K 31/496; C07D 491/107;
(Continued)

(56) References Cited

U.S. PATENT DOCUMENTS 10,077,276 B2 * 9/2018 Chen ....................... A61P 35/02
10,336,774 B2 * 7/2019 Chen ....................... A61P 35/00
(Continued)

FOREIGN PATENT DOCUMENTS

TW          202035417 A    10/2020
WO     WO 2009/053737 A2    4/2009
(Continued)

OTHER PUBLICATIONS

Saal C, Becker A. Pharmaceutical salts: a summary on doses of salt formers from the Orange Book. Eur J Pharm Sci. Jul. 1, 20136; 49(4):614-23. doi: 10.1016/j.ejps.2013.05.026. Epub Jun. 5, 2013. PMID: 23747999. (Year: 2013).*
(Continued)

*Primary Examiner* — Mark L Shibuya
*Assistant Examiner* — Kevin S Martin
(74) *Attorney, Agent, or Firm* — LATHROP GPM LLP; Brian C. Trinque

(57) ABSTRACT

The invention relates to a method for the manufacture of a compound of Formula I as mentioned above, or a pharmaceutically acceptable salt, acid co-crystal, hydrate or other solvate thereof, said method comprising reacting a compound of the formula II with a compound of the formula III according to the following reaction scheme: wherein A, LG, n and m are as defined in the Summary of the Invention.

(Continued)

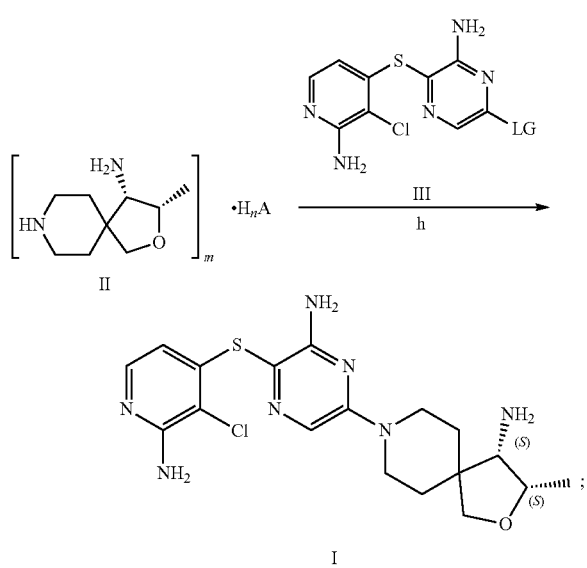

14 Claims, 10 Drawing Sheets

(51) Int. Cl.

| | |
|---|---|
| C07D 491/107 | (2006.01) |
| A61K 31/438 | (2006.01) |
| A61K 31/496 | (2006.01) |
| A61P 35/00 | (2006.01) |
| C07D 211/22 | (2006.01) |
| C07D 211/62 | (2006.01) |
| C07D 213/127 | (2006.01) |
| C07D 213/61 | (2006.01) |
| C07D 401/12 | (2006.01) |

(58) Field of Classification Search
CPC .............. C07D 213/127; C07D 213/61; C07D 401/12; C07D 211/22; C07D 211/62; C07B 2200/13; Y02P 20/55; A61P 35/00
See application file for complete search history.

(56) References Cited

U.S. PATENT DOCUMENTS

| | | | | |
|---|---|---|---|---|
| 2021/0371429 A1* | 12/2021 | Chen | ................... | C07D 471/10 |
| 2022/0073537 A1* | 3/2022 | Chen | ................... | C07D 401/04 |

FOREIGN PATENT DOCUMENTS

| | | | | |
|---|---|---|---|---|
| WO | WO 2011/029804 A1 | 3/2011 | | |
| WO | WO 2015/107493 A1 | 7/2015 | | |
| WO | WO 2015/107494 A1 | 7/2015 | | |
| WO | WO-2015107495 A1 * | 7/2015 | ........... | A61K 31/495 |
| WO | WO 2016/203404 A1 | 12/2016 | | |
| WO | WO 2016/203405 A1 | 12/2016 | | |
| WO | WO 2016/203406 A1 | 12/2016 | | |
| WO | WO 2017/211303 A1 | 12/2017 | | |
| WO | WO 2017/216706 A1 | 12/2017 | | |
| WO | WO 2018/080916 A1 | 5/2018 | | |
| WO | WO 2018/130928 A1 | 7/2018 | | |
| WO | WO 2018/136265 A1 | 7/2018 | | |
| WO | WO 2018/172984 A1 | 9/2018 | | |
| WO | WO 2020/065452 A1 | 4/2020 | | |
| WO | WO 2020/165732 A1 | 8/2020 | | |
| WO | WO 2020/165733 A1 | 8/2020 | | |
| WO | WO 2020/165734 A1 | 8/2020 | | |
| WO | WO 2021/171261 A1 | 9/2021 | | |
| WO | WO 2021/224867 A1 | 11/2021 | | |
| WO | WO 2022/009098 A1 | 1/2022 | | |

OTHER PUBLICATIONS

Bastin et al., "Salt Selection and Optimisation Procedures for Pharmaceutical New Chemical Entities", *Organic Process Research & Development* 4:427-435 (2000), doi:10.1021/op000018u.

Bernstein, "Polymorphism of Molecular Crystals", Moscow, Nauka, Chapter 7.3.2, Bioavailability pp. 324-330 (2007).

Caira, "Crystalline Polymorphism of Organic Compounds", *Topics in Current Chemistry* 198:163-208 (1998).

Gould, "Salt selection for basic drugs", *International Journal of Pharmaceuticals* 33:201-217 (1986).

Kümmerer, "Pharmaceuticals in the Environment", *Annual Review of Environment and Resources* 35:57-75 (2010), doi: 10.1146/annurev-environ-052809-161223.

Morissette et al., "High-throughput crystallization: polymorphs, salts, co-crystals and solvates of pharmaceutical solids", *Advanced Drug Delivery Reviews* 56(3):275-300 (2004), https://doi.org/10.1016/j.addr.2003.10.020.

Serajuddin, "Salt formation to improve drug solubility", *Advanced Drug Reviews* 59:603-616 (2007), https://doi.org/10.1016/j.addr.2007.05.010.

Awad et al., "Deprotonation of chloropyridines using lithium magnesates", *Tetrahedron Letters* 45:7873-7877 (2004).

International Search Report and Written Opinion for International Application No. PCT/IB2019/057864, mailed Feb. 11, 2020, 22 pages.

Evans et al., "Asymmetric Induction in Methyl Ketone Aldol Additions to α-Alkoxy and α,β-Bisalkoxy Aldehydes: A Model for Acyclic Stereocontrol", *Journal of the American Chemical Society* 128(29):9433-9441 (2006).

Trost et al., "Development of ProPhenol Ligands for the Diastereo- and Enantioselective Synthesis of β-Hydroxy-α-amino Esters", *Journal of the American Chemical Society* 136(8):3016-3019 (2014).

Kuznetsova, Methodical instructions, Irkutsk State University (Gouvpoigu), General Physics Department, 2005.

Mashkovskiy, Drugs, Manual for Physicians, 15th Edition, pp. 10-11, 2005.

Balbach et al., "Pharmaceutical evaluation of early development candidates 'the 100 mg-approach'", *International Journal of Pharmaceutics* 275:1-12 (2004).

Singhal et al., "Drug polymorphism and dosage form design: a practical perspective", *Advanced Drug Delivery Reviews* 56:335-347 (2004).

Berge et al., "Pharmaceutical Salts", *Journal of Pharmaceutical Sciences* 66(1):1-19 (1977).

* cited by examiner

PROCESS OF MANUFACTURE OF A COMPOUND FOR INHIBITING THE ACTIVITY OF SHP2, AS WELL AS PRODUCTS RESULTING FROM ACID ADDITION

BACKGROUND

Field of the Invention

The present invention relates to (pharmaceutically acceptable) salts, and polymorphs thereof, of a compound capable of inhibiting the activity of SHP2, as well as polymorphs of the free base form of said compound, and/or to a process for the manufacture of said compound, (pharmaceutically acceptable) salts and polymorphs thereof.

BACKGROUND OF THE INVENTION

The Src Homology-2 phosphatase (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

The compound with the name (3S,4S)-8-(6-amino-5-((2-amino-3-chloropyridin-4-yl)thio)pyrazin-2-yl)-3-methyl-2-oxa-8-azaspiro[4.5]decan-4-amine, which has the formula I,

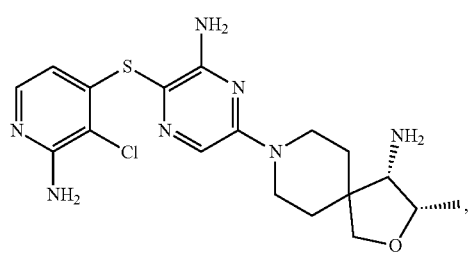

(I)

is described in WO/2015/107495 A1 as an inhibitor of SHP2, where also various therapeutic methods and treatment methods are also described.

The Src Homology-2 phosphatase (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

Mutations in the PTPN11 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compound that can be manufactured according to the present invention fulfills the need of small molecules to that inhibit the activity of SHP2.

WO/2015/107495 A1 describes a method for the manufacture of the compound of the formula I which can be characterized by the following reaction scheme 1:

Scheme 1:

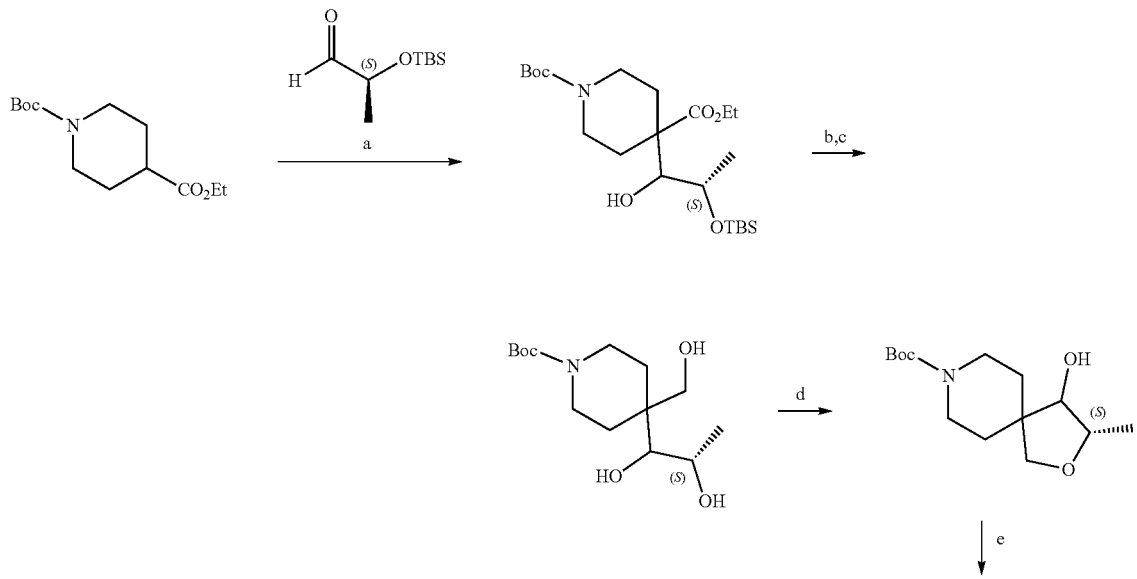

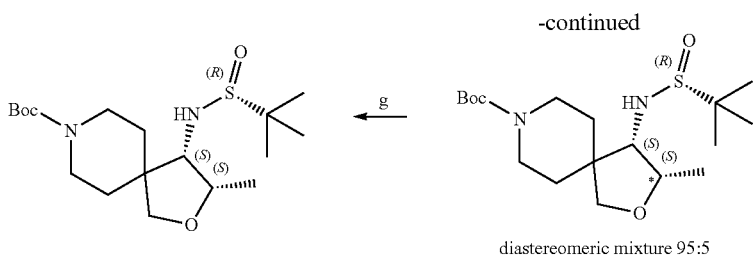
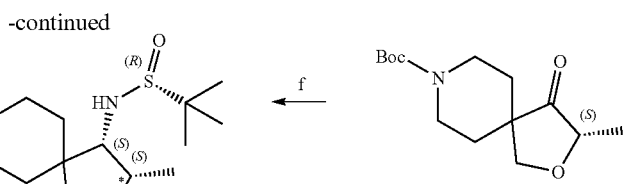

diastereomeric mixture 95:5

The last compound resulting from step g above was then reacted as in the following scheme 2:

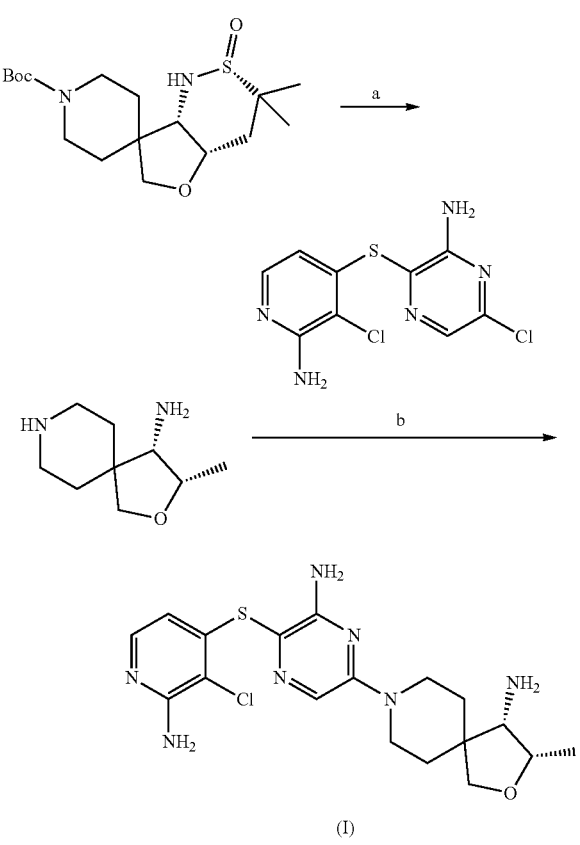

Thus the compound of formula I is obtained (last compound in the scheme 2, above). The synthesis requires at least the 9 steps shown and is rather appropriate for synthesis in laboratory amounts.

The manufacture is complicated and requires, for example, the separation of the diastereomers at step g in reaction scheme 1, above. Furthermore, many of the intermediates do not crystallize so that they have to be used without taking advantage of higher purity based on crystallization.

In addition, further chromatographic steps are used in the process.

Furthermore, the aldehyde starting material for reaction a in Scheme 1 above is a compound known from the literature but not available in bulk (only in gram scale, for example from Aldlab Chemicals), showing some inherent instability so that advantageously it is prepared and used immediately. Thus for large scale synthesis (for example, in kilogram or more scale manufacturing) it is more problematic to use.

In addition, the cyclisation (step d in Scheme 1, above) has only moderate yield, with educt, the tosylate of the desired product and further impurity also being present, so that separation is required.

The ketone substrate product of step e in Scheme 1) is partially racemized, even if enantiomeric pure aldehyde starting material is used, resulting in the formation of 4 diastereomers in step f (which actually comprises two steps, condensation and reduction), leading to a 95:5 ratio of the two major disatereomers which would require further separation.

Furthermore, the synthesis involves many oily intermediates as indicated in the following scheme:

Scheme 1A

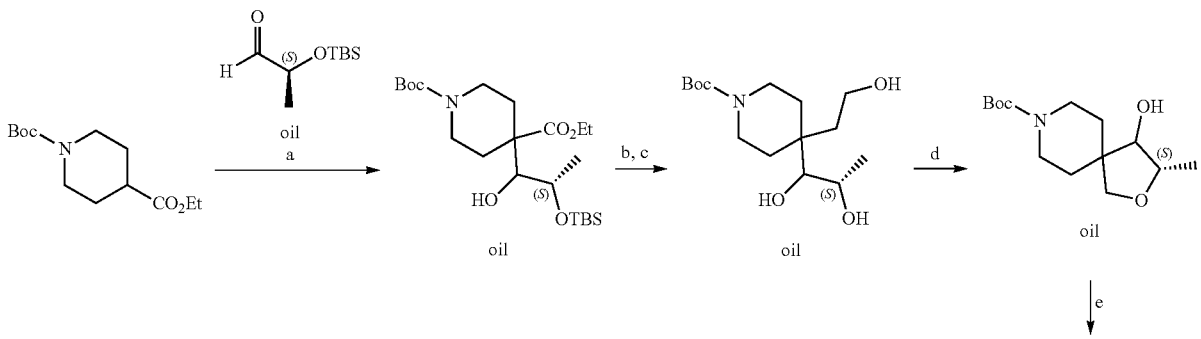

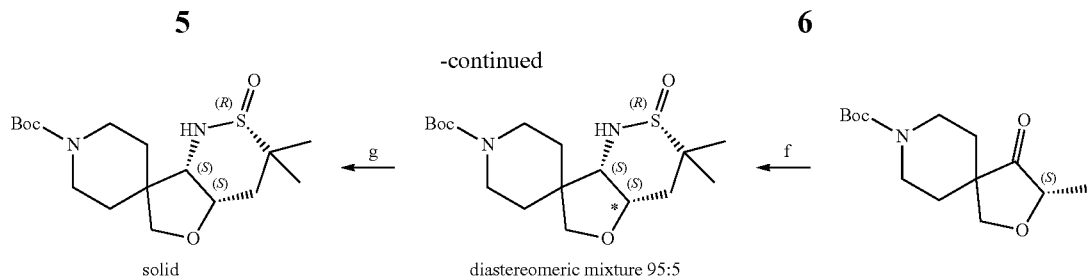

solid      diastereomeric mixture 95:5

Therefore, the process, though readily feasible on a laboratory scale, is not ideal for manufacture at a large scale.

The compound added in reaction b in Scheme 2 is obtained in WO 2015/107495 A1 as "Intermediate 10" follows:

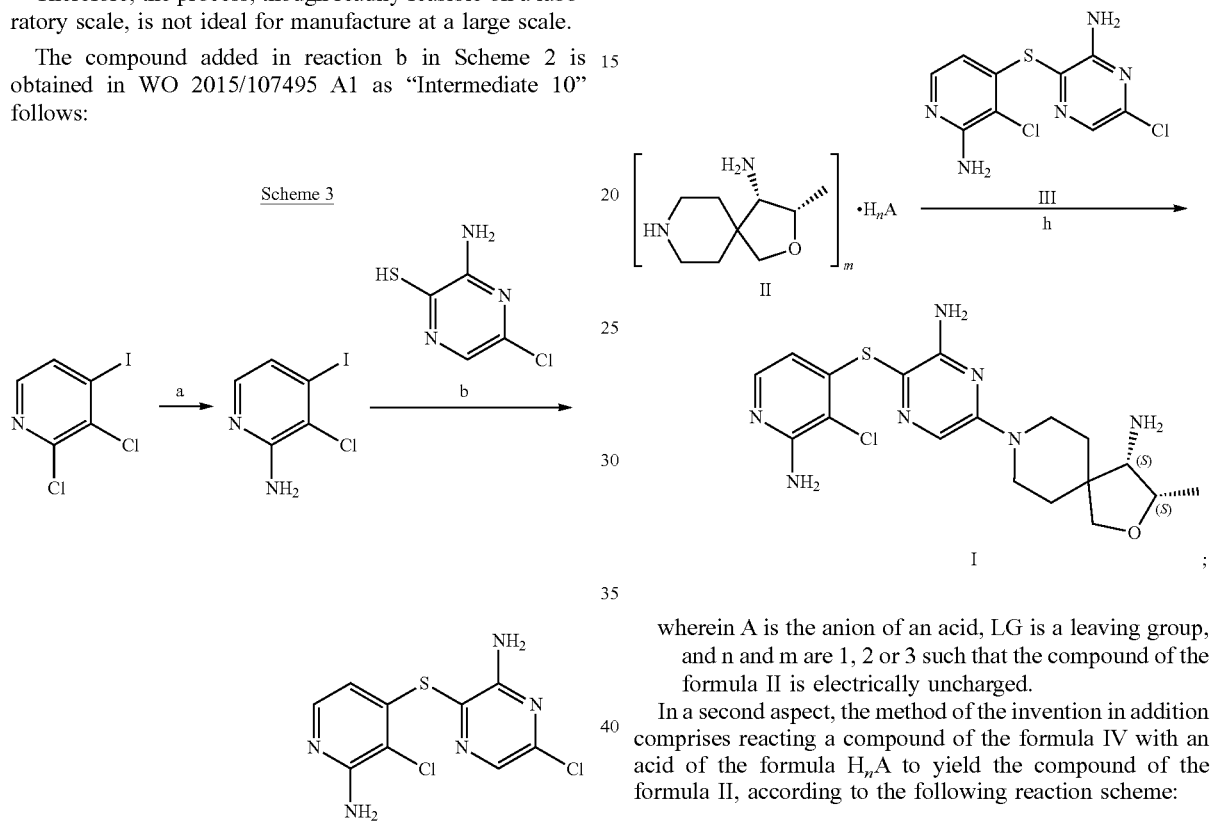

An issue here is the relatively low yield of the amine resulting from reaction a in Scheme 3.

In addition, while WO 2015/107495 A1 generically mentions that pharmaceutically acceptable salts of the compound of the formula I may be obtainable, no concrete reason for obtaining such salts and no specific examples of salts are described.

In addition, given the many potentially salt forming groups in formula I, it is not clear whether any salts with a clear stoichiometry can be formed at all.

SUMMARY OF THE INVENTION

In a first aspect, the present invention provides a method for the manufacture of a compound of Formula I as mentioned above, or a pharmaceutically acceptable salt, acid co-crystal, hydrate or other solvate thereof, said method comprising reacting a compound of the formula II with a compound of the formula III according to the following reaction scheme:

wherein A is the anion of an acid, LG is a leaving group, and n and m are 1, 2 or 3 such that the compound of the formula II is electrically uncharged.

In a second aspect, the method of the invention in addition comprises reacting a compound of the formula IV with an acid of the formula $H_nA$ to yield the compound of the formula II, according to the following reaction scheme:

wherein $R_1$ is a protecting group for the secondary amino, HY is a chiral acid, A is the anion of an acid, and n and m are integers 1, 2 or 3 such that the compound of the formula II is electrically uncharged.

In a third aspect, the method of the invention in addition comprises reacting a compound of the formula V, or a salt thereof, with a chiral acid of the formula HY to yield the compound of the formula IV according to the following reaction scheme:

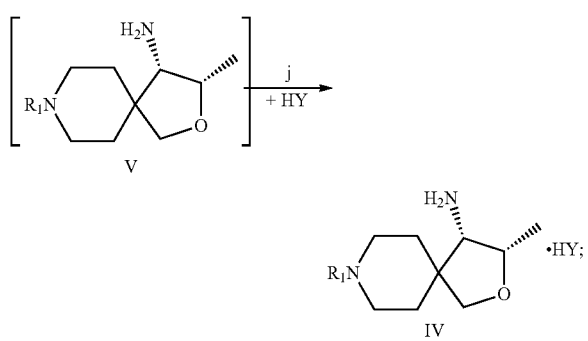

wherein $R_1$ is a protecting group for secondary amino and HY is a chiral acid.

In a fourth aspect, the method of the invention in addition comprises reacting a compound of the formula VI to yield the compound of the formula V according to the following reaction scheme:

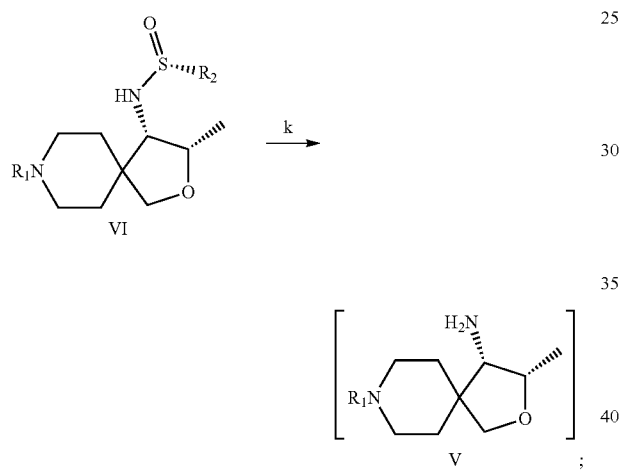

wherein $R_1$ is a protecting group for secondary amino and $R_2$ is alkyl, especially tertiary alkyl.

In a fifth aspect, the method of the invention in addition comprises reducing a compound of the formula VII to yield the compound of the formula VI according to the following reaction scheme:

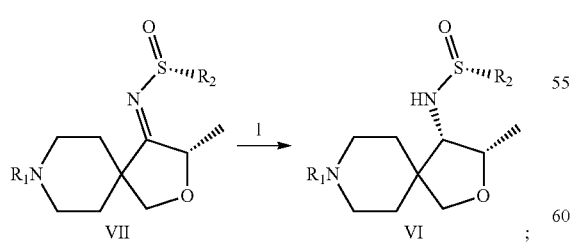

wherein $R_1$ is a protecting group for the secondary amino and $R_2$ is alkyl, preferably tertiary-alkyl.

In a sixth aspect, the method of the invention in addition comprises reacting a compound of the formula VIII with a compound of the formula IX to yield the compound of the formula VII according to the following reaction scheme:

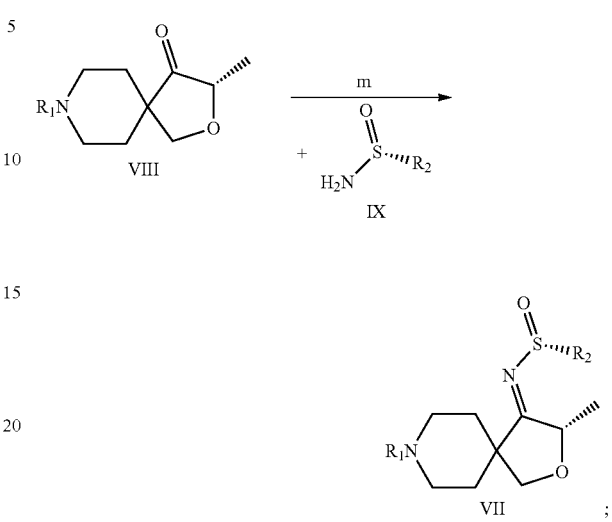

wherein $R_1$ is a protecting group for secondary amino and $R_2$ is alkyl, preferably tert.-alkyl.

In a seventh aspect, the method of the invention in addition comprises oxidising a compound of the formula X to yield the compound of the formula VIII according to the following reaction scheme:

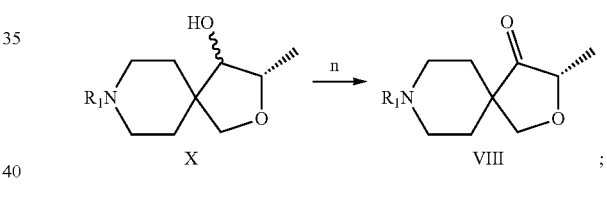

wherein $R_1$ is a protecting group for secondary amino.

In an eighth aspect, the method of the invention in addition comprises cyclizing a compound of the formula XI to yield the compound of the formula X according to the following reaction scheme:

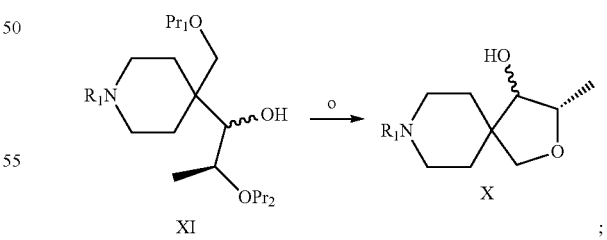

wherein $R_1$ is protecting group for secondary amino, $Pr_1O$ is a leaving group and $Pr_2$ is a substituted silyl protecting group.

In a ninth aspect, the method of the invention in addition comprises protecting a compound of the formula XII with a compound of the formula $Pr_1H$ to yield the compound of the formula XI according to the following reaction scheme:

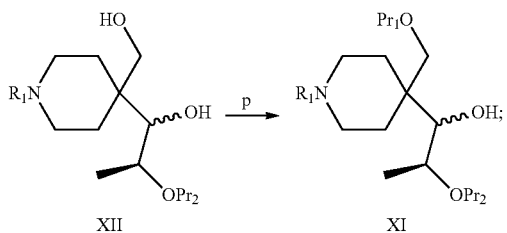

wherein $R_1$ is a protecting group for secondary amino, $Pr_1O$ is a leaving group, especially toluenesulfonyl, and $Pr_2$ is a substituted silyl protecting group, especially a trialkyl- or a diphenylalkyl-silyl group, especially tert-butyldimethylsilyl.

In a tenth aspect, the method of the invention in addition comprises reducing a compound of the formula XIII to yield the compound of the formula XII according to the following reaction scheme:

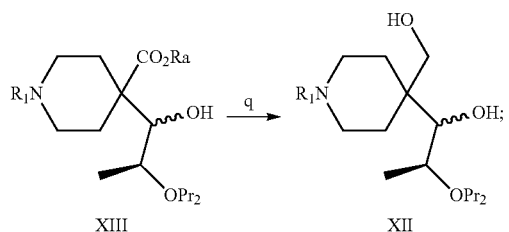

wherein $R_1$ is a protecting group for secondary amino, Ra is an unsubstituted or substituted alkyl or an unsubstituted or substituted aryl group and $Pr_2$ is a substituted silyl protecting group, especially a trialkyl- or a diphenylalkyl-silyl group, especially tert-butyldimethylsilyl.

In an eleventh aspect, the method of the invention in addition comprises reacting a compound of the formula XIV with a compound of the formula XV to yield the compound of the formula XIII according to the following reaction scheme:

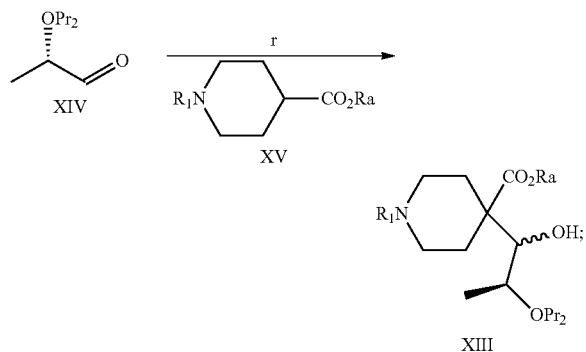

wherein $R_1$ is a protecting group for secondary amino, Ra is an unsubstituted or substituted alkyl or an unsubstituted or substituted aryl group and $Pr_2$ is a substituted silyl protecting group, especially trialkyl- or a diphenylalkyl-silyl group, especially tert-butyldimethylsilyl.

In a twelfth aspect, the method of the invention in addition comprises reducing a compound of the formula XVI to yield the compound of the formula XIV according to the following reaction scheme:

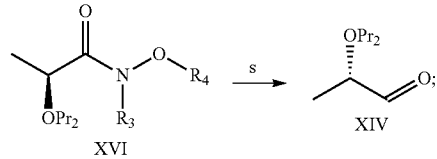

wherein $Pr_2$ is a substituted silyl protecting group, especially trialkyl- or a diphenylalkyl-silyl group, especially tert-butyldimethylsilyl, $R_3$ is an alkyl group and $R_4$ is an alkyl group.

In a thirteenth aspect, the method of the invention in addition comprises reacting an ester compound of the formula XVII with a compound of the formula $R_4ONHR_3$ to yield the compound of the formula XVI according to the following reaction scheme:

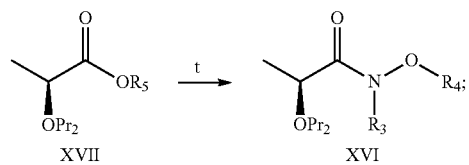

wherein $Pr_2$ is a substituted silyl protecting group, especially trialkyl- or a diphenylalkyl-silyl group, especially tert-butyldimethylsilyl, $R_3$ is an alkyl group, $R_4$ is an alkyl group and $R_5$ is an unsubstituted or substituted alkyl group or an unsubstituted or substituted aryl group.

In a fourteenth aspect, the method of the invention in addition comprises protecting a compound of the formula XVIII with a compound of the formula $Pr_2HAL$ to yield the compound of the formula XVII according to the following reaction scheme:

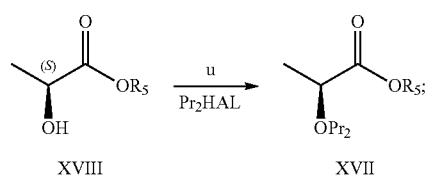

wherein $Pr_2$ is a substituted silyl protecting group, especially trialkyl- or a diphenylalkyl-silyl group, especially tert-butyldimethylsilyl, HAL is halo and $R_5$ is an unsubstituted or substituted alkyl group or an unsubstituted or substituted aryl group.

In a fifteenth aspect of the invention, the compound of the formula I in free base form, especially obtainable or preferably obtained according to the first aspect of the invention or according to any one of the second to fourteenth invention aspects, is preferably converted to an acid addition salt of the formula I* by reaction with an inorganic or preferably organic acid of the formula $H_rB$ according to the following reaction scheme:

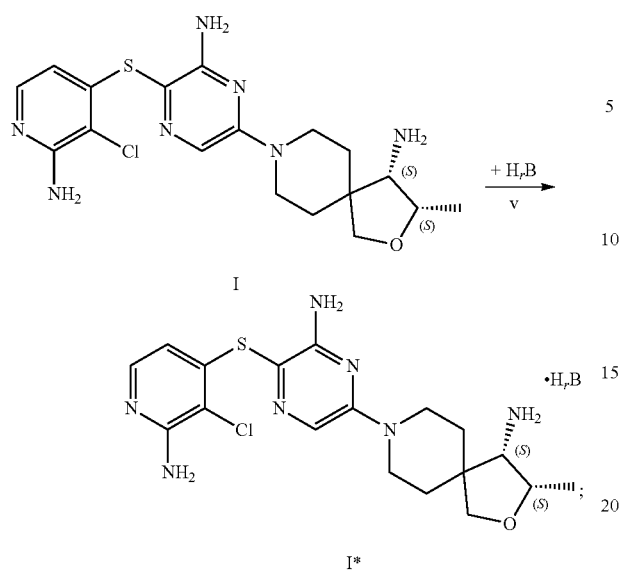

wherein $H_rB$ is an acid in which r is an integer, preferably 1, 2, 3 or 4.

In a sixteenth aspect of the invention, the compound of formula III is preferably obtained by halogenating a compound of the formula XVIII:

(XVIII)

wherein LG is a leaving group, especially halo, such as chloro; with a halogenating agent for example a halosucciniomide, such as bromosuccinimide, preferably in an aprotic solvent, such as a halogenated hydrocarbon, a nitrile, an ether or an $C_1$-$C_6$alkanoyl-di($C_1$-$C_6$alkyl) amide, such as acetonitrile, dichloromethane, tetrahydrofurane or N,N-dimethalacetamide, or a mixture of 2 or more of these solvents, preferably at temperatures in the range from 10° C. to the boiling point of the reaction mixture, for example from 10 to 100° C., to yield compound of the formula XIX:

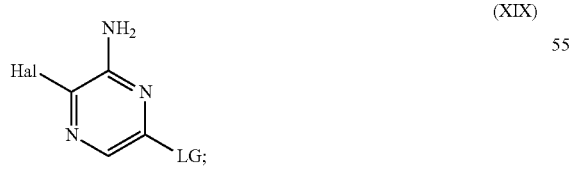

(XIX)

wherein LG is a leaving group, especially as defined above, and Hal is halogen, especially bromo, which is then substituted with a mercapto compound of the formula XX;

$R_6O—C(=O)—CH_2—CH_2—SH$ (XX);

wherein $R_6$ is unsubstituted or substituted alkyl or unsubstituted or substituted aryl, especially $C_1$-$C_6$alkyl, such as ethyl, to give a compound of the formula XXI;

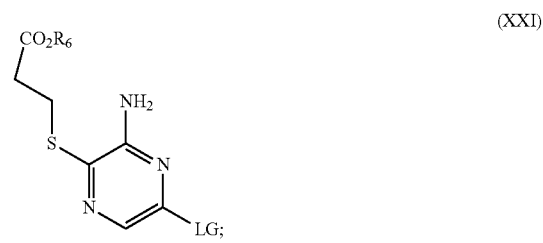

(XXI)

wherein LG is a leaving group and $R_6$ is unsubstituted or substituted alkyl or unsubstituted or substituted aryl (both preferably as defined above). The reaction preferably takes place in the presence of a noble metal complex comprising a noble metal, especially Palladium, and a ligand, such as Xantphos, in the presence of a tertiary amine, such as diisopropylethylamine, in an aprotic solvent, fro example an ester, preferably a cyclic ester, such as dioxane. The reaction proceeds at preferably elevated temperatures, for example from about 30° C. to about the boiling point of the reaction mixture. The compound of formula XXI is then treated with an alkoxylate, especially a methoxylate or an ethoxylate, of an alkaline metal, especially lithium, potassium or most especially sodium, to yield a compound of the formula XXII:

(XXII)

wherein Mt is an alkaline metal, especially as just defined, which compound of the formula XXII is then reacted with a compound of the formula XXIII. The reaction preferably takes place in a solvent, such as a mixture of an alcohol, for example methanol or ethanol (especially an alcohol matching with the alkoxylate so that the alkoxygroup is identical to the organic rest in the alcohol, and an ether, for example a cyclic ether, such as tetrahydrofurane, preferably at a temperature in the range from about 0 to about 50° C.:

(XXIII)

to yield the compound of the formula III:

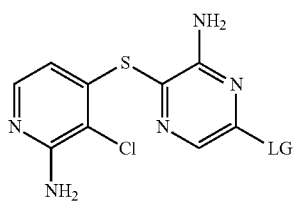

wherein LG is a leaving group, especially as defined above for a compound of the formula III.

The compound of formula XXIII can preferably be obtained by reacting a compound of the formula XXIV:

(XXIV)

with iodine in the presence of a strong base, especially an alkyl-alkaline metal, such as n-butyllithium, and a nitrogen base, especially di-isopropylamine or diethylamine, in a solvent, such as an acyclic or especially cyclic ether, preferably tetrahyrofurane, at preferably low temperatures, for example in the range from about −80 to about −5° C.

The resultant compound of the formula XXV:

(XXV)

is treated with ammonia to yield the compound of the formula XXIII. This reaction then preferably takes place in the presence of gaseous ammonia and an inert polar solvent, such as DMSO, especially at elevated temperatures, preferably in the range from about 30° C. to about the boiling point of the reaction mixture, for example at about 85 to about 95° C.

As an alternative to the synthesis from a compound of the formula XVIII, a compound of the formula XIX in which Hal is chloro and LG is chloro can also be obtained by treating a compound of the formula XXVI;

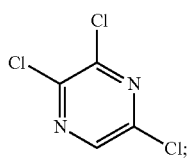

(XXVI)

with ammonia to yield the compound of the formula XIX in which Hal is chloro (the reaction conditions are preferably as just described for the reaction of the compound of the formula XXV), and is then, by the further reactions via compounds of the formula XXI, XXII and then reacting as above with the compound of formula XXIII (which is preferably obtained as described above) reacted to yield the compound of the formula III, each of the compounds and reaction conditions preferably being as defined as preferred above.

In a seventeenth aspect, the compound of the formula XXVI just described can be reacted with ammonia (preferably in an aqueous medium and at temperatures in the range from about 0 to about 80° C.) to yield the compound of the formula XIX in which Hal is chloro and LG is chloro, which is then reacted with a (preferably anhydrous)alkaline metal sulfide of the formula $Mt_2S$, in which Mt is an alkaline metal, especially sodium, and then working up with a quaternary ammonium halogenide of the formula $(alk)_4NZ$, in which each alk is independently of the others alkyl, especially n-alkyl, such as $C_1$-$C_6$-alkyl and Z is halo, especially chloro or more especially bromo, to yield a compound of the formula XXVII:

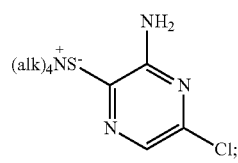

(XXVII)

in which alk is as just defined, which can then be reacted with a compound of the formula XXIII (which can preferably be prepared as described above), preferably in the presence of a copper (I) iodide complex, such as CuI/phenanthroline, in an appropriate solvent, for example in water or an alcohol or a mixture thereof, preferably in water and/or methanol, ethanol or especially isopropanol, preferably at temperatures in the range from about −20 to about 80° C., for example from about 0 to about 40° C., to yield the compound of the formula III.

DEFINITIONS

Figure 1:
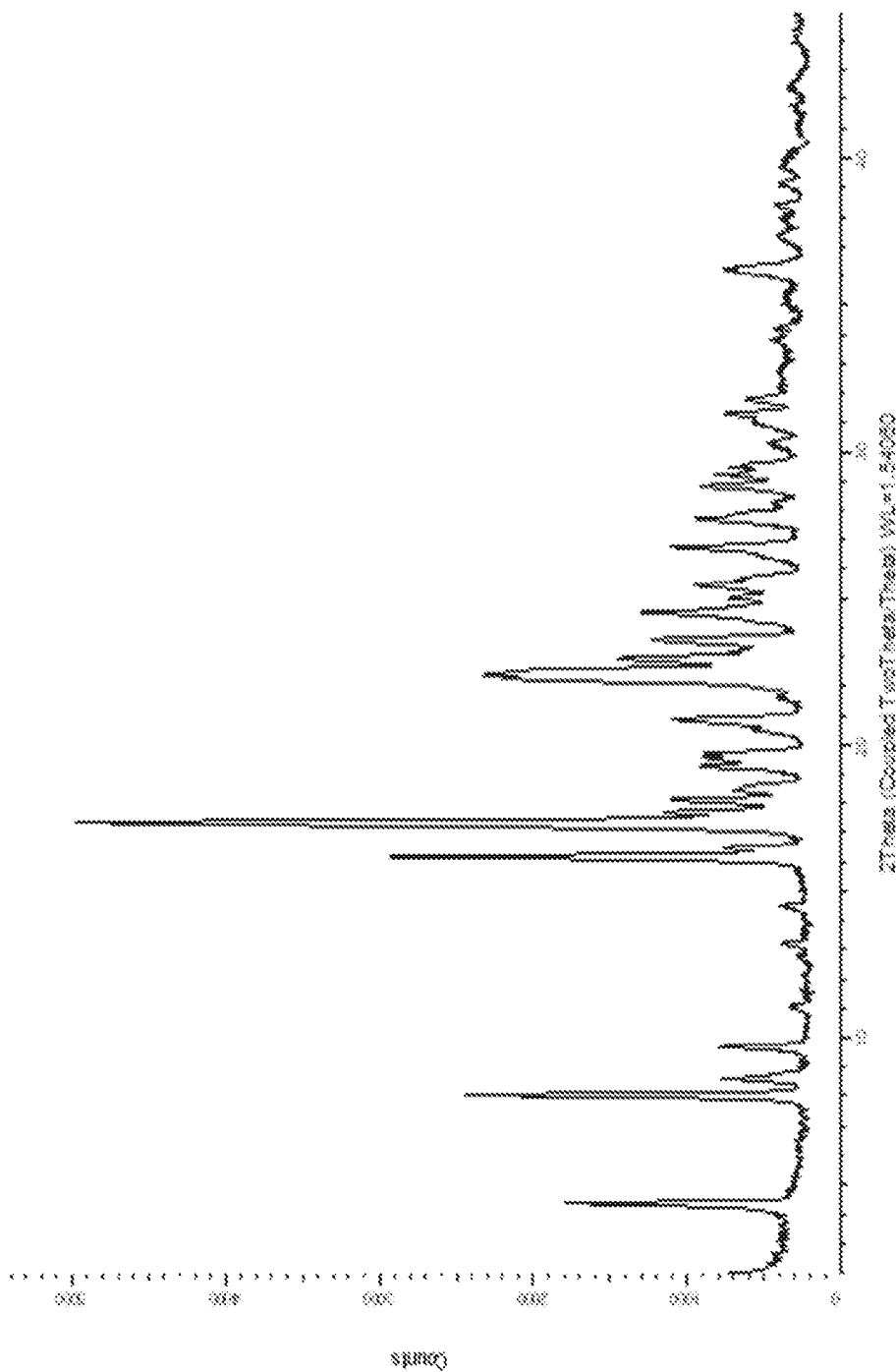
FIG. 1: shows an XRPD of (3S,4S)-8-(6-amino-5-((2-amino-3-chloropyridin-4-yl)thio)pyrazin-2-yl)-3-methyl-2-oxa-8-azaspiro[4.5]decan-4-amine, succinate (1:1) hemihydrate, modification (form) $H_A$.

"SHP2" means "Src Homolgy-2 phosphatase" and is also known as SH-PTP2, SH-PTP3, Syp, PTPID, PTP2C, SAP-2 or PTPN11. Cancers harboring "PTPN11 mutations" include but are not limited to: N58Y; D61Y, V; E69K; A72V, T, D; E76G, Q, K (ALL); G60A; D61Y; E69V; F71K; A72V; T73I; E76G, K; R289G; G503V (AML); G60®, D61Y, V, N; Y62D; E69K; A72T, V; T73I; E76K, V, G, A, Q; E139D; G503A, R; Q506P (JMML); G60V; D61V; E69K; F71L; A72V; E76A (MDS); Y63C (CMML); Y62C; E69K; T507K (neuroblastoma); V46L; N58S; E76V (Lung cancer); R138Q (melanoma); E76G (colon cancer).

The present invention also includes all suitable isotopic variations of the compounds mentioned in the processes and especially in Embodiment A to K above. An isotopic variation is defined as one in which at least one atom is replaced by an atom having the same atomic number but an atomic mass different from the atomic mass usually found in nature. Examples of isotopes that may be incorporated include, but are not limited to, isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations, for example, those in which a radioactive isotope such as $^3H$ or $^{14}C$ is incorporated, are useful in drug and/or substrate tissue distribution studies. In particular examples, 3H and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations can generally be prepared by conventional procedures using appropriate isotopic variations of suitable reagents.

DESCRIPTION OF PREFERRED EMBODIMENTS

The following definitions define more general features in a preferred more specific way, and it is possible to replace one, more than one or all of the more general features in the invention variants embodiments by a more specific definition, which defines more specific invention embodiments. The same is also true for reaction embodiments described above and their preferred versions as mentioned above.

The mentioned compounds can be present in free form or as salts thereof where salt-forming groups (such as imino or amino) are present, especially the acid addition salts, such as salts with an inorganic acid, such as a hydrogenhalide, for example HCl, sulfuric acid or phosphoric acid, and/or with an organic acid, such as a sulfonic acid, such as methylsulfonic acid, ethylsulfonic acid or toluenesulfonic acid, a phosphonic acid or a carboxylic acid, for example an alkanoic acid, such as acetic acid or citric acid.

In the following, preferred conditions for the reactions described above are defined;

The reaction of a compound II with a compound of the formula III (reaction h), wherein LG is a leaving group, preferably halo, especially chloro or bromo, preferably takes place in the presence of a weak base, such as an alkali metal carbonate or hydrogencarbonate, preferably in an aprotic solvent, such as an N,N-Dialkylamide of an alkanoic acid, for example dimethyl acetamide or dimethyl formamide, at preferably elevated temperatures, for example in the range from about 30° C. to about the boiling point of the reaction mixtures, for example from about 50 to about 100° C.

The reaction of a compound of the formula IV to a compound of the formula II (reaction i) preferably takes place in the presence of an (achiral) organic or preferably inorganic acid of the formula $H_nA$ as defined above and below, preferably trifluoroacetic acid, trifluoromethane sulfonic acid or preferably an inorganic acid, for example sulfuric acid, phosphoric acid or especially a hydrogen halide, most especially hydrogen chloride, preferably in a solvent, for example an alcohol or a mixture of alcohols, such as isopropylalcohol and/or methanol, and/or in the presence of water (especially if $R_2$ is an acyl, especially lower alkanoyl, for example acetyl) at preferred temperatures in the range from about 0° C. to about the boiling temperature of the solvent, for example from about 10° C. to (especially where $R_2$ is acyl) about 40° C.

The reaction of a compound of the formula V with a chiral acid HY to a compound of the formula IV (reaction j) preferably takes place in the presence of an apolar, especially aprotic, solvent, such as a nitrile, for example acetonitrile, preferably at temperatures on the range from about 10° C. to about the boiling temperature of the reaction mixture, for example from about 15 to about 75° C. The chiral acid HY is preferably a chiral carboxylic or sulfonic or phosphonic acid, especially a chiral carboxylic acid with one carboxylic (—COOH) group, such as (-)—O-acetyl-D-mandelic acid, dibenzyl-D-tartaric acid, or di-para-toluoyl-D-tartaric acid. $R_1$ is preferably a $C_1$-$C_6$alkyloxycarbony, such as tert-butoxycarbonyl, and A is preferably the anion of an acid, especially of an acid as mentioned in the paragraph immediately preceding this paragraph.

The reaction of a compound of the formula VI to yield the compound of the formula V (reaction k) preferably takes place in the presence of an acid, especially a strong acid, for example an inorganic acid, such as sulfuric acid, phosphoric acid or especially a hydrohalic acid, preferably hydrochloric acid, preferably in a solvent, for example an alcohol, such as an alkanol, for example methanol, ethanol or especially isopropanol, or an estger, such as an alkylalkanoate, for example isopropylacetate, or a mixture thereof, in the presence or absence of water, at preferred temperatures in the range from −50 to 30° C., for example from −30 to 10° C., and yields a compound of the formula V in the form of a salt of the mentioned acid, which is then preferably reacted with, especially by continuously adding it, a base, for example an alkalimetal hydroxide, such as LiOH, KOH or especially NaOH, preferably in an organic solvent, for example an ether, such as methyl tert-butyl ether, preferably at low temperatures, for example in the range from −50 to 10° C., especially from −20 to 0° C., transferred into the free base of the compound of the formula V. $R_1$ is preferably a $C_1$-$C_6$alkyloxycarbony, such as tert-butoxycarbonyl, and $R_2$ is preferably tertiary-$C_4$-$C_6$alkyl, such as tert-butyl.

The reduction of a compound of the formula VII to yield the compound of the formula VI (reaction I) preferably takes place with a complex hydride capable of reducing the imino group, such as lithium borohydride, preferably in an organic solvent, for example a mixture of an alcohol, for example propanol, ethanol or especially methanol, and/or an ether, especially a cyclic ether, such as tetrahydrofurane, preferably at low temperatures, for example in the range from about-78 to about 0° C., especially from about −50 to about −20° C. $R_1$ and $R_2$ are preferably as defined in the paragraph immediately preceding this paragraph.

The reaction of a compound of the formula VIII with a compound of the formula IX to yield the compound of the formula VII (reaction m) preferably takes place in the presence of a Lewis Acid activating the carbonyl for condensation, such as titanium-tetraisoproponate or especially titanium tetraethanolate, preferably in an aprotic solvent, for example an ether, such as a cyclic ether, especially tehtrahydrofurane, at preferred temperatures in the range from about 20° C. to about the boiling point of the reaction mixture, for example from about 40 to about 80° C. $R_1$ and $R_2$ are preferably as defined in the two last paragraphs immediately preceding this paragraph.

The oxidation of a compound of the formula X to yield the compound of the formula VIII (reaction n) preferably takes place in the presence of an oxidant such as a mixture of TEMPO ((2,2,6,6-Tetramethylpiperidin-1-yl)oxyl) and bleach (especially sodium or potassiume hypochlorite), TEMPO and (diacetoxy) iodobenzene or preferably Dess-Martin periodinane, preferably in an aprotic solvent, for example a halogenated hydrocarbon, such as dichloromethane, preferably at temperatures in the range from about −40 to about 40° C., for example from about −10 to about 30° C. $R_1$ is preferably a $C_1$-$C_6$ alkyloxycarbony, such as tert-butoxycarbonyl.

The cyclization of a compound of the formula XI to yield the compound of the formula X (reaction o) preferably takes place in the presence of a phase transfer catalyst, for example a tetraalkylammonium halogenide, such as tetra-n-butylammoniumbromide, preferably in an aprotic solvent, such as an ether, especially a cyclic ether, for example tetrahydrofurane, at preferred temperatures in the range fom about −20 to about 50° C., for example from about −5 to about 30° C. $R_1$ is preferably a $C_1$-$C_6$alkyloxycarbony, such as tert-butoxycarbonyl, $R_2$ is preferably tertiary-$C_4$-$C_6$alkyl, such as tert-butyl, $Pr_1O$ is preferably alkyloxy or preferably perfluoroalkylsulfonyloxy, tosyloxy or mesyloxy and $Pr_2$ is preferably a trialkyl- or a diphenylalkyl-silyl group, preferably a trialkylsilyl group, more preferably trimethylsilyl, tert-butyldiphenylsilyl, triisopropylsilyl or especially tert-butyldimethylsilyl.

The protection of a compound of the formula XII with a compound of the formula $Pr_1H$ to yield the compound of the formula XI (reaction p) preferably takes place in the presence of a base, such as an alkalimetal-bis(trialkylsubstituted silyl)amide, such as Lithium bis(trimethylsilyl)amide, preferably in an aprotic solvent, such as an ether, for example a cyclic ether, such as tetrahydrofurane, at preferred temperatures in the range from about −50 to about 50° C., for example from about −10 to about 10° C. $R_1$ is preferably a $C_1$-$C_6$alkyloxycarbony, such as tert-butoxycarbonyl, $Pr_1$ is preferably alkyl or preferably perfluoroalkylsulfonyl, tosyl or mesyl and $Pr_2$ is preferably a trialkyl- or a diphenylalkyl-silyl group, preferably a trialkylsilyl group, more preferably trimethylsilyl, tert-butyldiphenylsilyl, triisopropylsilyl or especially tert-butyldimethylsilyl.

The reduction of a compound of the formula XIII to a compound of the formula XII (reaction q) preferably takes place with a complex hydride capable of reducing an esterified carboxylic group to a hydroxymethyl group, such as lithium aluminium hydride, Red-A1 (sodium-bis(2-methoxyethoxy)aluminium hydride), sodium borohydride in the presence of calcium chloride or especially lithium borohydride, preferably in an aprotic solvent, such as an ether, for example a cyclic ether, for example tetrahydrofuran, prefereably at temperatures in the range from about −50 to about 50° C., for example from about 10 to about 40° C. $R_1$ is preferably a $C_1$-$C_6$alkyloxycarbony, such as tert-butoxycarbonyl, Ra is preferably alkyl, more preferably $C_1$-$C_6$alky, for example ethyl, and $Pr_2$ is preferably a trialkyl- or a diphenylalkyl-silyl group, preferably a trialkylsilyl group, more preferably trimethylsilyl, tert-butyldiphenylsilyl, triisopropylsilyl or especially tert-butyldimethylsilyl.

The reaction of a compound of the formula XIV with a compound of the formula XV to a compound of the formula XIII (reaction r) preferably takes place in the presence of a strong base, such as lithium-bis(trimethylsilyl)amide, lithium 2,2,6,6-tetramethylpiperidide or especially lithium diisopropylamide, preferably in an aprotic solvent, preferably an ether, such as a cyclic ether, especially tetrahydrofuran, preferably at low temperatures, for example in the range from about −78 to about 0° C., for example from about −60 to about −18° C. $R_1$ is preferably a $C_1$-$C_6$alkyloxycarbony, such as tert-butoxycarbonyl, Ra is preferably alkyl, more preferably $C_1$-$C_6$alkyl, for example ethyl, and $Pr_2$ is preferably a trialkyl- or a diphenylalkyl-silyl group, preferably a trialkylsilyl group, more preferably trimethylsilyl, tert-butyldiphenylsilyl, triisopropylsilyl or especially tert-butyldimethylsilyl.

The reaction of a compound of the formula XVI to yield a compound of the formula XIV (reaction s) preferably takes place in the prescence of a reductant capable of reducing a hydroxylamide group to a carbonyl group, for example Red-A1 or especially lithium aluminium hydride, preferably in an aprotic solvent, such as an ether and/or a halogenated hydrocarbon, for example a cyclic ether and/or a halogenated alkane, such as tetrahydrofuran and/or dichloromethane, preferably at low temperatures, for example from about −100 to about 0° C., such as from about −78 to about −50° C. $Pr_2$ is preferably a trialkylsilyl group, more preferably trimethylsilyl, tert-butyldiphenylsilyl, triisopropylsilyl or especially tert-butyldimethylsilyl, and each of $R_3$ and $R_4$ is preferably alkyl, more especially methyl or ethyl, and $Pr_2$ is preferably a trialkyl- or a diphenylalkyl-silyl group, preferably a trialkylsilyl group, more preferably trimethylsilyl, tert-butyldiphenylsilyl, triisopropylsilyl or especially tert-butyldimethylsilyl.

The reaction of a compound of the formula XVII to a compound of the formula XVI (reaction t) preferably takes place with a hydroxylamine compound of the formula $R_3$—O—NH—$R_4$, wherein $R^3$ and $R_4$ are as defined above for a compound of the formula XVI;

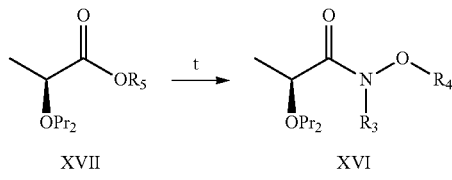

wherein $Pr_2$ is a substituted silyl protecting group, $R_3$ is an alkyl group, $R_4$ is an alkyl group and $R_5$ is an unsubstituted or substituted alkyl group or an unsubstituted or substituted aryl group. The reaction preferably takes place in the presence of a Grignard reagent, preferably of the formula Org-MgX, in which Org is a hydrocarbon radical, especially with up to 10 carbon atoms, especially isopropylmagnesium chloride. Preferably, the reaction takes place at temperatures in the range of about −50 to about 50° C., for example in the range from about −20 to about 20° C. Each of $R_3$ and $R_4$ is, independently of the other, preferably $C_1$-$C_6$alkyl, for example ethyl or especially methyl, and $Pr_2$ is preferably a trialkylsilyl group, more preferably trimethylsilyl, tert-butyldiphenylsilyl, triisopropylsilyl or especially tert-butyldimethylsilyl.

The protecting of a compound of the formula XVIII with a compound of the formula $Pr_2HAL$ to yield the compound of the formula XVII (reaction u) preferably takes place in the presence of a tertiary nitrogen base, such as imidazole, preferably in an aprotic solvent, such as a halogenated hydrocarbons, especially dichloromethane, at preferred temperatures in the range from about −50 to about 50° C., especially from about −20 to about 20° C.

Preferably, $R_5$ is phenyl-$C_1$-$C_6$alkyl or especially $C_1$-$C_6$alkyl; $Pr_2$ is trimethylsilyl, tert-butyl-diphenylsilyl, triisopropylsilyl or especially tert-butyldimethylsilyl. HAL is preferably bromo or especially chloro.

The reaction of a compound of the formula I to a compound (actually a salt) of the formula I* with an acid $H_rB$, which is preferably an inorganic acid, for example a hydrohalic acid (r=2), such as hydrochloric acid, sulfuric acid (r=2) or phosphoric acid (r=3) or in particular organic acid, for example methylsulfonic acid or adipic acid (r=1), or especially a dicarbonic acid (r=2), preferably fumaric acid, most preferably succinic acid, preferably takes place in acetonitrile, water and/or one or more alcohols, such as (in each case optionally aqueous) methanol, ethanol or isopropyl alcohol (or a mixture of 2 or 3 thereof) or acetonitrile. The reaction proceeds at preferred temperatures from about −40° C. to about the boiling point of the reaction mixture, preferably from 30 to 80° C., preferably followed by cooling, for example to about −30 to about 30° C. Alternatively, the salt may be obtained from a suspension of the compound of the formula I in the presence of the acid $H_rB$ at a temperature in the range from about 20 to about 70° C., preferably in an organic solvent, such as an ether, for example tetrahydrofurane. $H_rB$ is preferably an acid as defined above and below for an acid of the formula $H_nA$ or more especially selected from the group consisting of succinic acid, hydrochloric acid, methylsulfonic acid, fumaric acid, and adipic acid. Preferred is succinic acid.

Preferably, each salt of the formula I* can be obtained by seeding with the corresponding salt obtainable as described below in Examples 6 to 14.

The present invention also relates to the following invention embodiments;

Embodiment A: The invention also relates to a compound or rather salt, especially in crystalline form, of the formula I*;

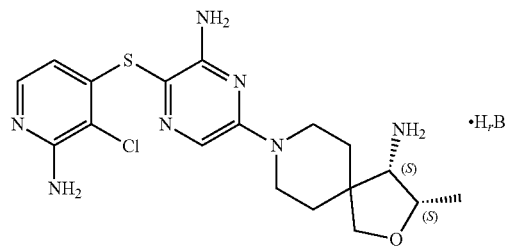

in which $H_rB$ is an acid selected from the group consisting of succinic acid, hydrochloric acid, methylsulfonic acid, fumaric acid, and adipic acid. Preferably succinic acid.

The ratio of free base for bivalent acids is preferably in the range (3S,4S)-8-(6-amino-5-((2-amino-3-chloropyridin-4-yl)thio)pyrazin-2-yl)-3-methyl-2-oxa-8-azaspiro[4.5]decan-4-amine: Acid (mol: mol)=1:1 to 1:1.5, or can be 2:1. In the following, the compounds of formula I* are named essentially by naming the anion of the acid (for example succinate), denoting the (approximate, for example+40%, more preferably +35% of the respective second values) stochiometry in parenthesis, for example (1:1), meaning 1 molecule of acid (for example succinic acid) per 1 (+40%, preferably +35%) molecule of (3S,4S)-8-(6-amino-5-((2-amino-3-chloropyridin-4-yl)thio)pyrazin-2-yl)-3-methyl-2-oxa-8-azaspiro[4.5]decan-4-amine ("free base"), or for example (2:1) meaning 2 molecules of acid per 1 (+40%, preferably +35%) molecule of the "free base", for example in the case of, for example, the hemisuccinate.

Where compounds of the formula I* are mentioned, this may relate to salts or co-crystal forms which may occasionally not be differentiated over the true salts with some of the characterization methods represented below, but for example by NMR spectroscopy. Preferably salts are mentioned.

Embodiment B: More preferably, said compound of the formula I* is the (3S,4S)-8-(6-amino-5-((2-amino-3-chloro-pyridin-4-yl)thio)pyrazin-2-yl)-3-methyl-2-oxa-8-azaspiro [4.5]decan-4-amine (which in free form is the compound of formula I) succinat Embodiment C: Most preferably, the invention relates to (3S,4S)-8-(6-amino-5-((2-amino-3-chloropyridin-4-yl)thio) pyrazin-2-yl)-3-methyl-2-oxa-8-azaspiro[4.5]decan-4-amine succinate (1:1) hemihydrate form $H_A$. (falling under formula I*), especially characterized by an XRPD (X-ray powder diffration pattern) with at least one, two, three or all of the following 2-theta values; 8.1, 16.3, 17.5, 22.5 and 26.8.

More preferably, the XRPD shows the 2-theta peaks indicated in the 2-theta value table in Example 6, and yet more preferably the XRPD is as shown in FIG. 1.

Preferred is also (3S,4S)-8-(6-amino-5-((2-amino-3-chloropyridin-4-yl)thio)pyrazin-2-yl)-3-methyl-2-oxa-8-azaspiro[4.5]decan-4-amine succinate (1:1), hemihydrate Form $H_A$ (falling under formula (*) with a melting point onset in Differential Scanning calorimetry (DSC) at 186° C., which feature can be used alone or on combination with the XRPD data just mentioned.

Figure 2:
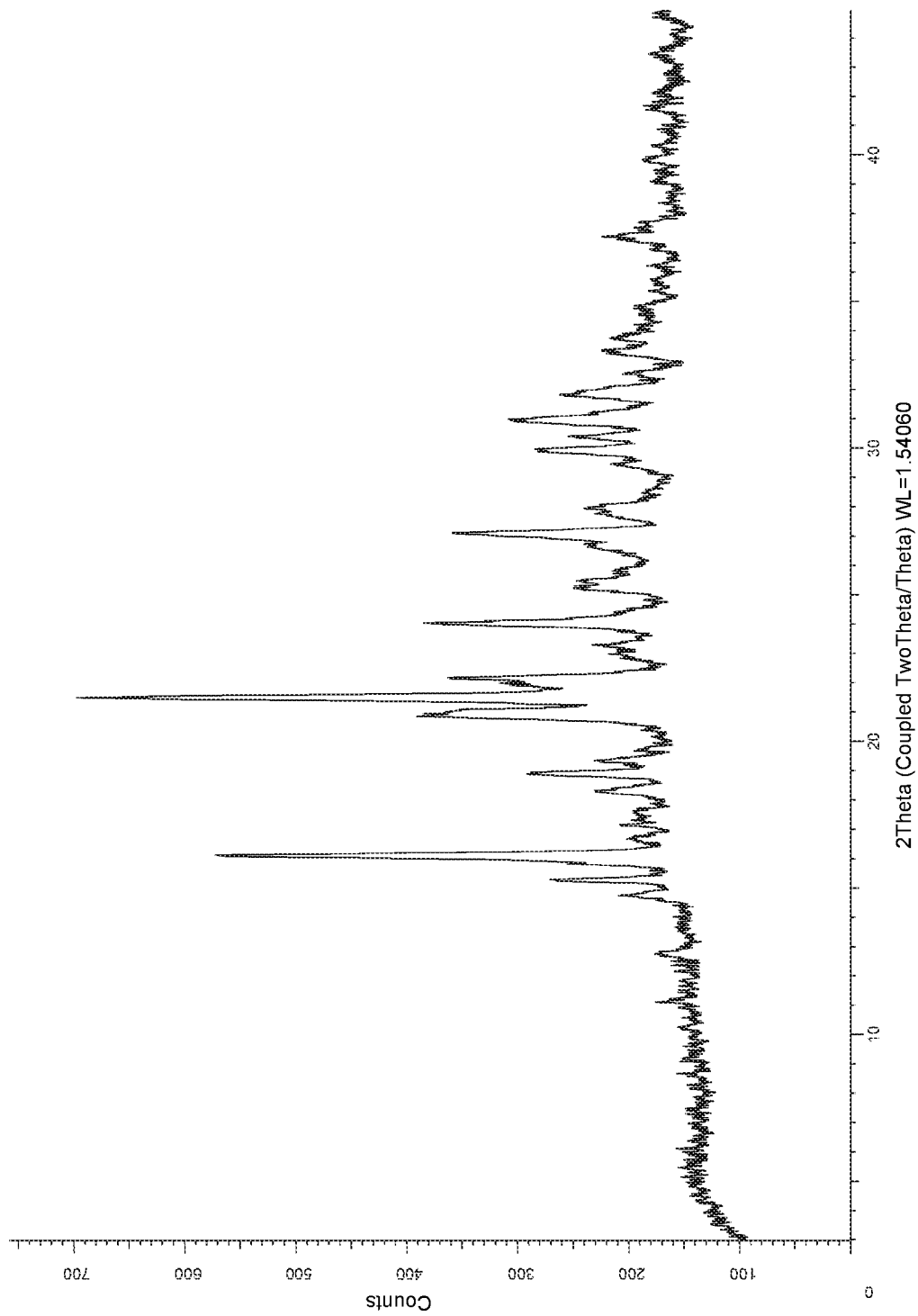
FIG. 2: shows an XRPD of (3S,4S)-8-(6-amino-5-((2-amino-3-chloropyridin-4-yl)thio)pyrazin-2-yl)-3-methyl-2-oxa-8-azaspiro[4.5]decan-4-amine hydrochloride.

Embodiment D: The invention also relates to a (3S,4S)-8-(6-amino-5-((2-amino-3-chloropyridin-4-yl)thio)pyrazin-2-yl)-3-methyl-2-oxa-8-azaspiro[4.5]decan-4-amine hydrochloride (falling under formula I*), especially with one, two, three, four or more or all XRPD peaks shown in the 2-theta table in Example 7, especially having an XRPD diagram as shown in FIG. 2.

Figure 3:
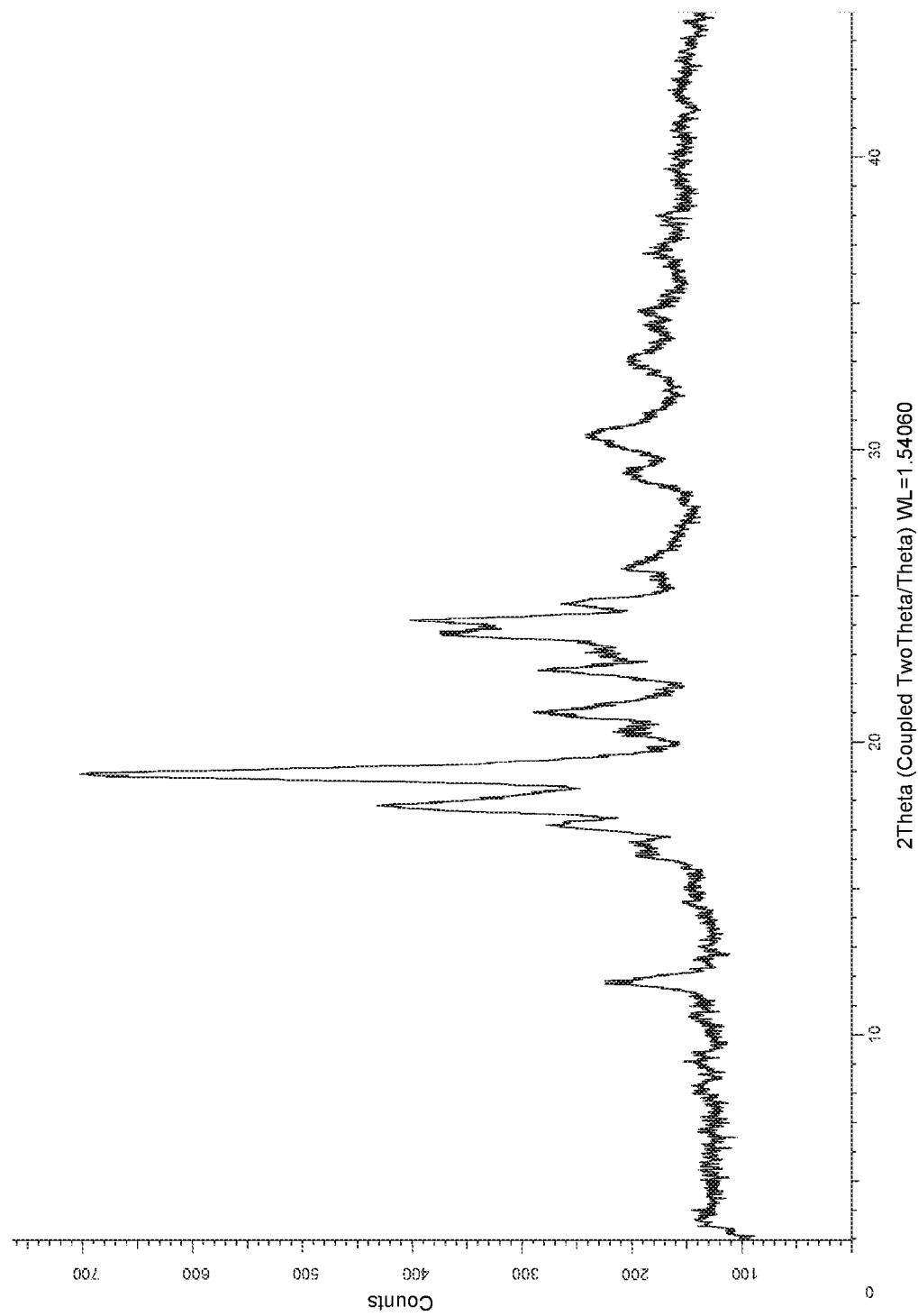
FIG. 3: shows an XRPD of (3S,4S)-8-(6-amino-5-((2-amino-3-chloropyridin-4-yl)thio)pyrazin-2-yl)-3-methyl-2-oxa-8-azaspiro[4.5]decan-4-amine mesylate.

Embodiment E: The invention also relates to a (3S,4S)-8-(6-amino-5-((2-amino-3-chloropyridin-4-yl)thio)pyrazin-2-yl)-3-methyl-2-oxa-8-azaspiro[4.5]decan-4-amine mesylate (falling under formula I*), especially with one, two, three, four or more or all XRPD peaks shown in the 2-theta table in Example 8, especially having an XRPD diagram as shown in FIG. 3.

Figure 4:
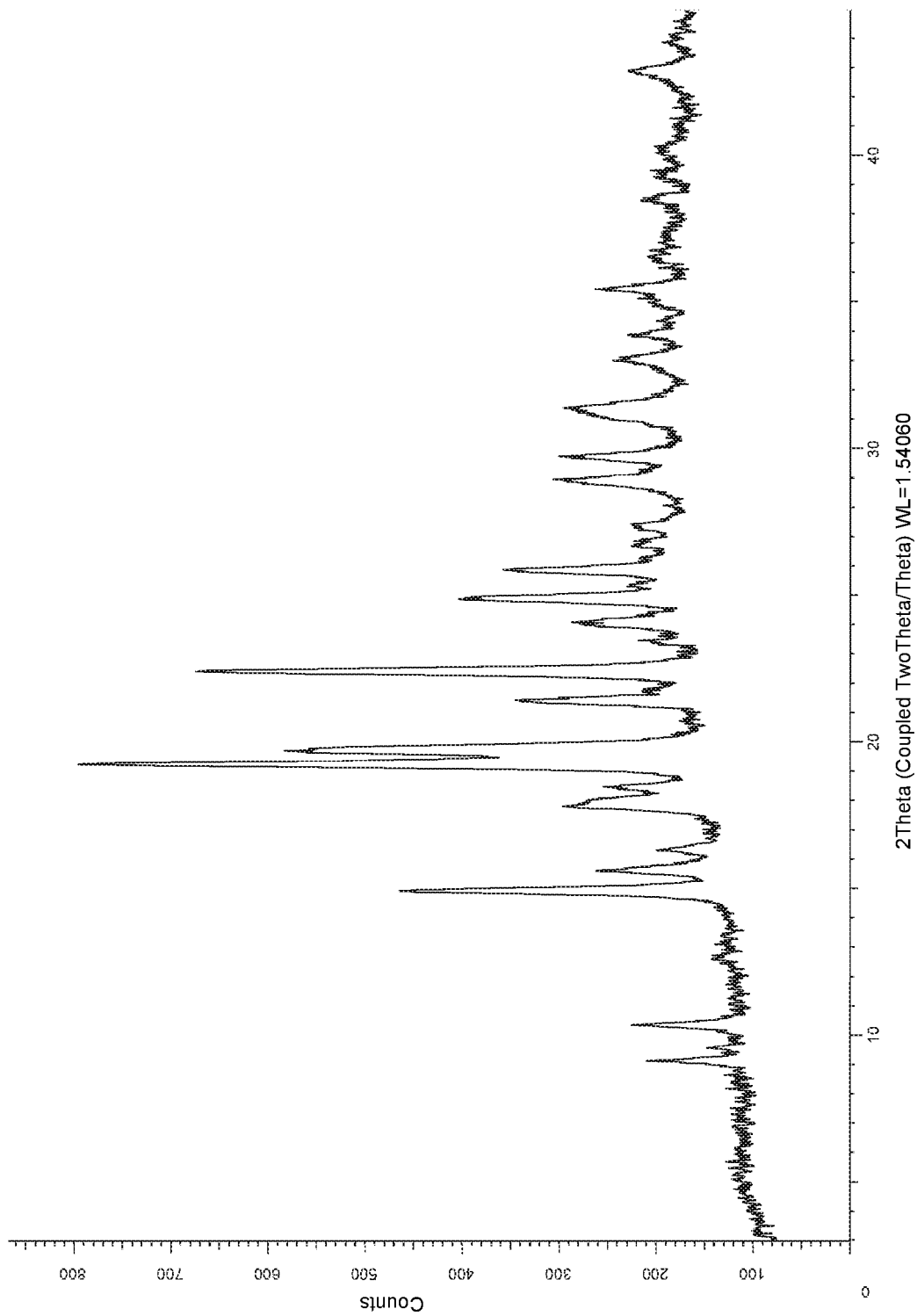
FIG. 4: shows an XRPD of (3S,4S)-8-(6-amino-5-((2-amino-3-chloropyridin-4-yl)thio)pyrazin-2-yl)-3-methyl-2-oxa-8-azaspiro[4.5]decan-4-amine, fumarate.

Embodiment F: The invention also relates to a (3S,4S)-8-(6-amino-5-((2-amino-3-chloropyridin-4-yl)thio)pyrazin-2-yl)-3-methyl-2-oxa-8-azaspiro[4.5]decan-4-amine, fumarate (falling under formula I*), especially with one, two, three, four or more or all XRPD peaks shown in the 2-theta table in Example 9, especially having an XRPD diagram as shown in FIG. 4.

Figure 5:
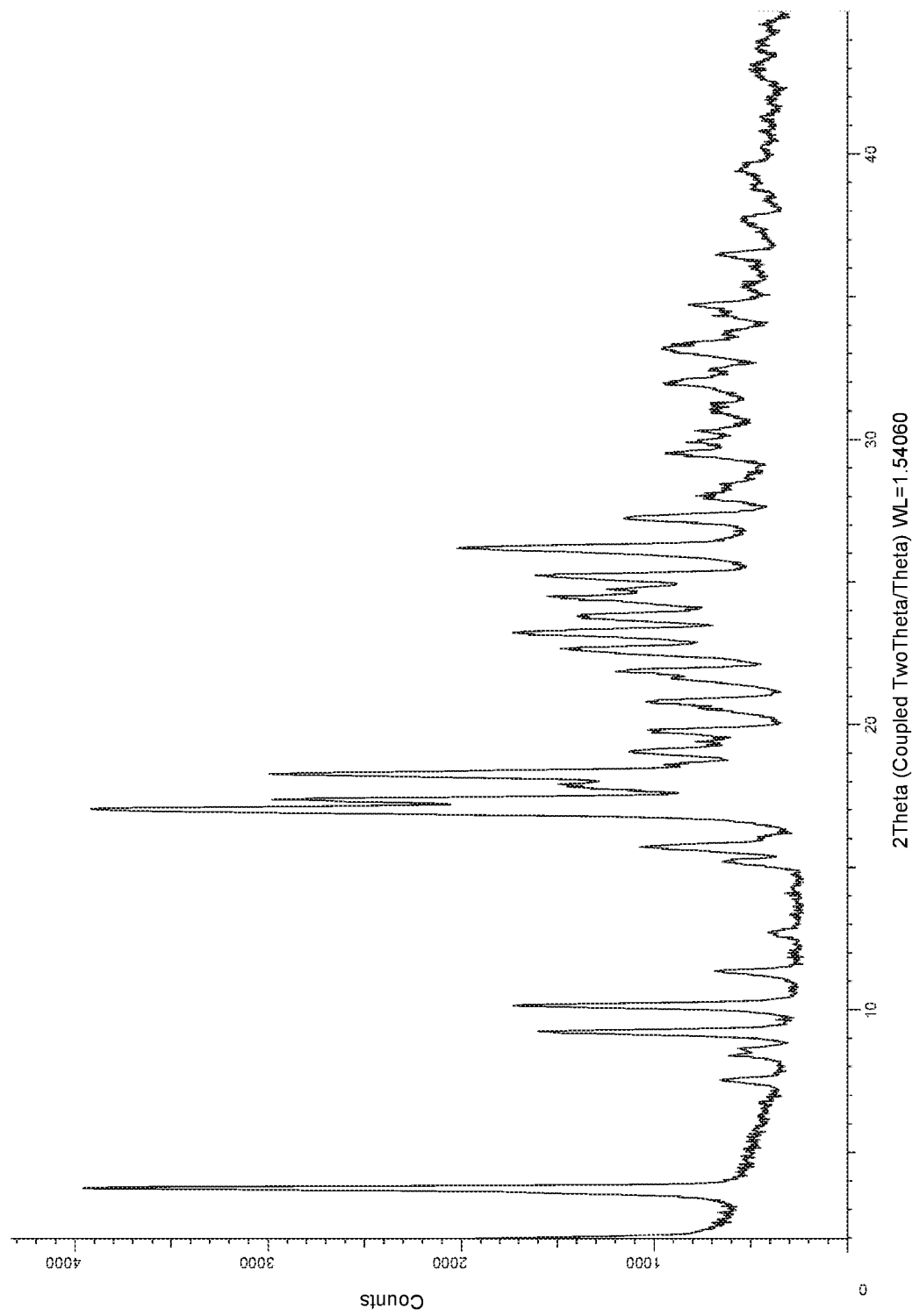
FIG. 5: shows an XRPD of (3S,4S)-8-(6-amino-5-((2-amino-3-chloropyridin-4-yl)thio)pyrazin-2-yl)-3-methyl-2-oxa-8-azaspiro[4.5]decan-4-amine adipate (1:1), Modification A.

Embodiment G: The invention also relates to a (3S,4S)-8-(6-amino-5-((2-amino-3-chloropyridin-4-yl)thio)pyrazin-2-yl)-3-methyl-2-oxa-8-azaspiro[4.5]decan-4-amine adipate (falling under formula I*) which latter can preferably be characterized by 1, 2, 3 or more or preferably all XRPD peaks having 2-theta values as shown in the 2-theta table in Example 10, especially by an XRPD-pattern as shown in FIG. 5 or by a melting onset temperature in DSC at 145.3° C., or by any combination of these features.

Figure 6:
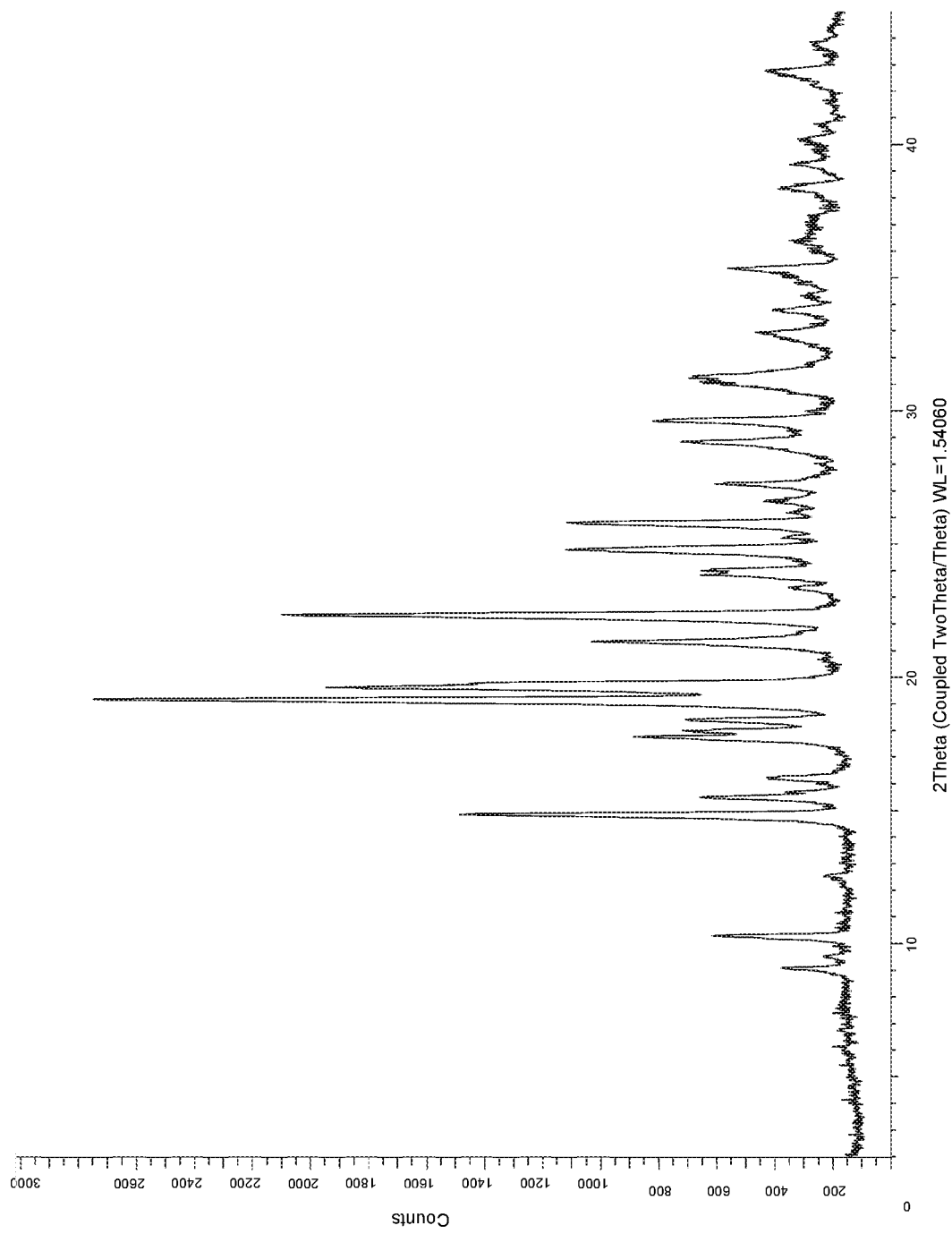
FIG. 6: shows an XRPD of (3S,4S)-8-(6-amino-5-((2-amino-3-chloropyridin-4-yl)thio)pyrazin-2-yl)-3-methyl-2-oxa-8-azaspiro[4.5]decan-4-amine, succinate (1:1), anhydrous form, Modification A.

Embodiment H: The invention also relates to (3S,4 S)-8-(6-amino-5-((2-amino-3-chloropyridin-4-yl)thio)pyrazin-2-yl)-3-methyl-2-oxa-8-azaspiro[4.5]decan-4-amine succinate (1:1), anhydrate, modification A, (falling under formula I*) which is preferably characterized by 1, 2, 3 or more XRPD or preferably all peaks having 2-theta values of 14.8, 19.2, 19.7, 22.3, 24.8, 25.8, or as shown in the 2-theta table in Example 11, especially by an XRPD pattern as shown in FIG. 6 or by a melting onset in DSC at 175.5° C., or by any combination of these features.

Figure 7:
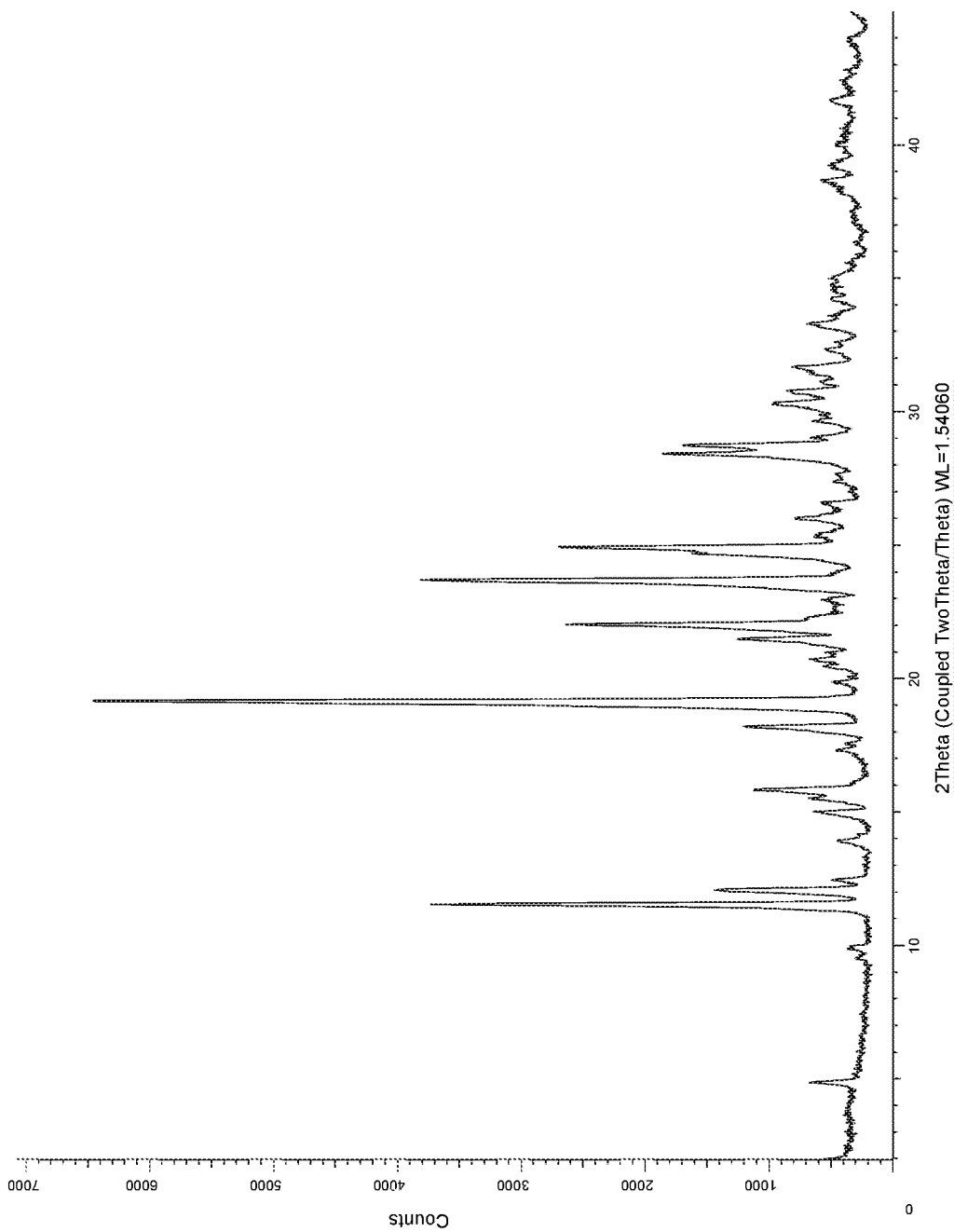
FIG. 7: shows an XRPD of (3S,4S)-8-(6-amino-5-((2-amino-3-chloropyridin-4-yl)thio)pyrazin-2-yl)-3-methyl-2-oxa-8-azaspiro[4.5]decan-4-amine, succinate (2:1), hydrate, Modification $H_A$.

Embodiment I: The invention also relates to (3S,4S)-8-(6-amino-5-((2-amino-3-chloropyridin-4-yl)thio)pyrazin-2-yl)-3-methyl-2-oxa-8-azaspiro[4.5]decan-4-amine succinate (2:1), hydrate, modification $H_A$, (falling under formula I*) which is preferably characterized by 1, 2, 3 or preferably all XRPD peaks having 2-theta values of. 11.5, 19.1, 22.0, 23.7, 24.9 degrees, or as shown in the 2-theta table in Example 12, especially an XRPD pattern as shown in FIG. 7, or by a melting onset temperature in DSC at 167.9° C., or by any combination of these features.

Figure 8:
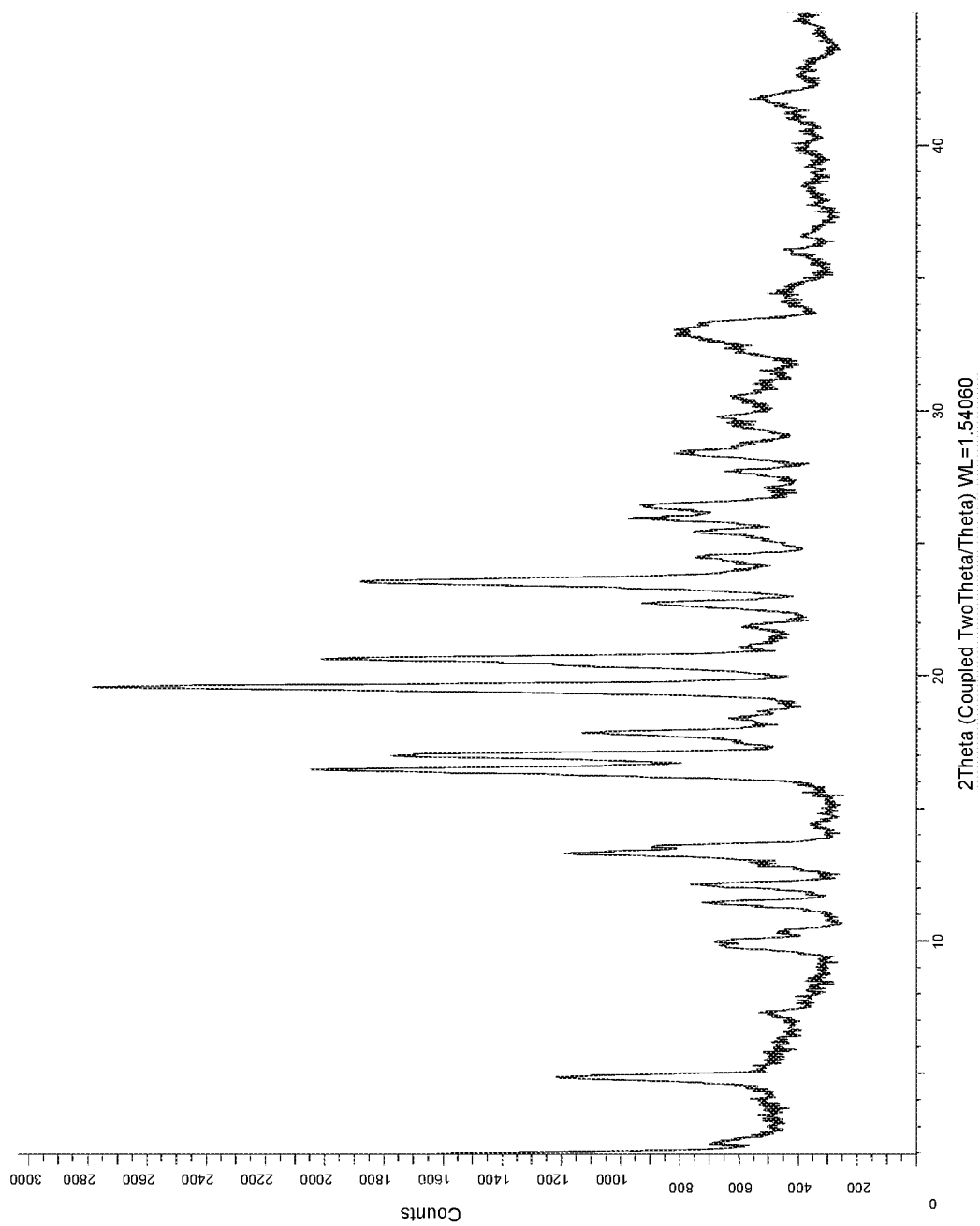
FIG. 8: shows an XRPD of. (3S,4S)-8-(6-amino-5-((2-amino-3-chloropyridin-4-yl)thio)pyrazin-2-yl)-3-methyl-2-oxa-8-azaspiro[4.5]decan-4-amine, succinate (2:1), anhydrate, Modification A.

Embodiment J: The invention also relates to (3S,4 S)-8-(6-amino-5-((2-amino-3-chloropyridin-4-yl)thio)pyrazin-2-yl)-3-methyl-2-oxa-8-azaspiro[4.5]decan-4-amine succinate (2:1), anhydrate, modification A, (falling under formula I*) which is preferably characterized by 1, 2, 3 or preferably all peaks having 2-theta values of 4.9, 13.3, 16.4, 17.0, 19.6, 20.6, 23.5 degrees or as shown in the 2-theta table in Example 14, especially by an XRPD pattern as shown in FIG. 8, or by a melting onset in DSC at 174.0° C., or by any combination of these features.

Figure 9:
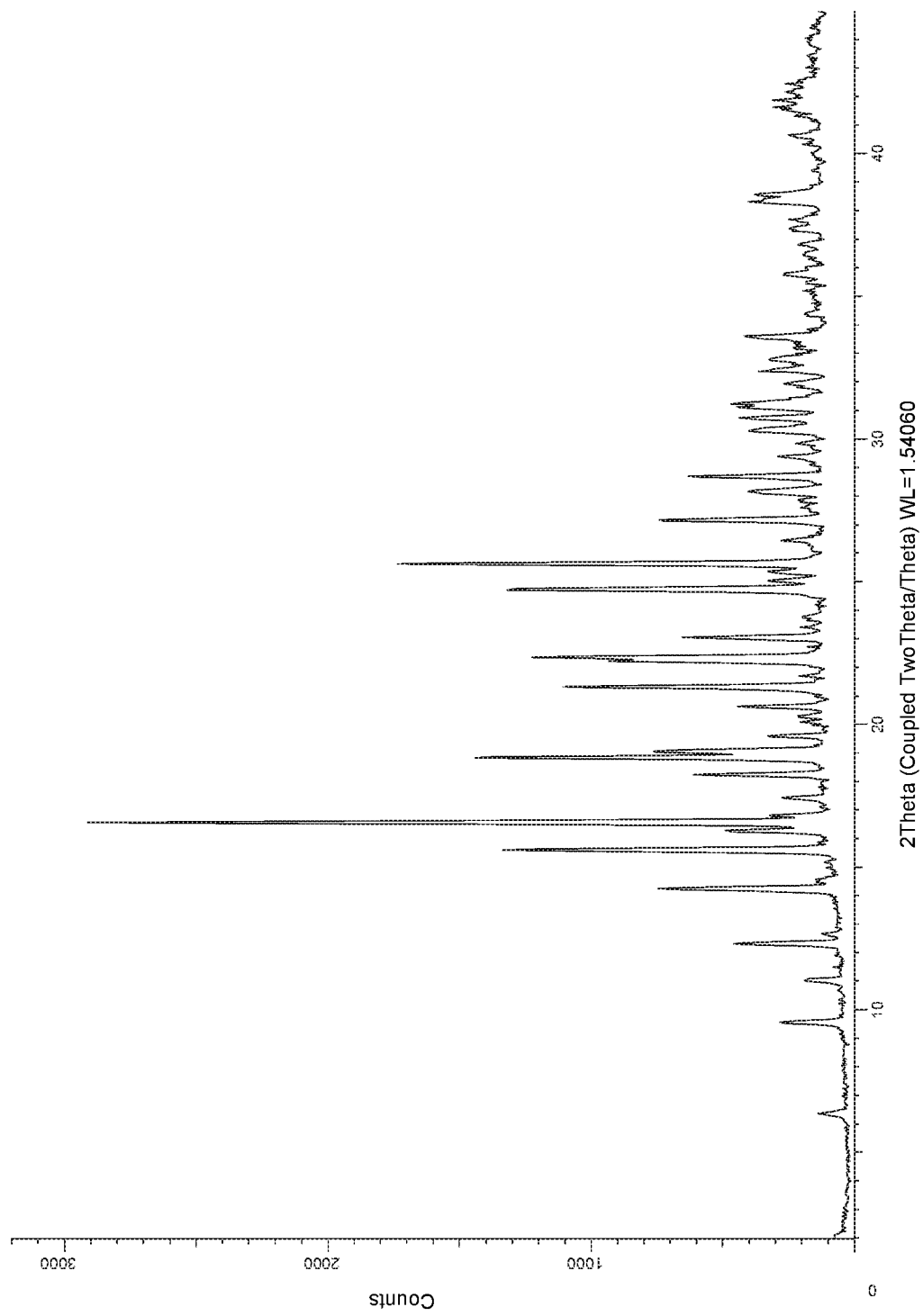
FIG. 9: shows an XRPD of (3S,4S)-8-(6-amino-5-((2-amino-3-chloropyridin-4-yl)thio)pyrazin-2-yl)-3-methyl-2-oxa-8-azaspiro[4.5]decan-4-amine free base Modification A.

Embodiment K: The invention also relates to (3S,4S)-8-(6-amino-5-((2-amino-3-chloropyridin-4-yl)thio)pyrazin-2-yl)-3-methyl-2-oxa-8-azaspiro[4.5]decan-4-amine free base, especially to Modification A thereof, which latter can preferably be characterized by 1, 2, 3 or more or preferably all XRPD peaks having 2-theta values as shown in the 2-theta table in Example 13, especially by an XRPD-pattern as shown in FIG. 9, or or by a melting onset temperature in DSC at 145.3° C., or by any combination of these features.

Figure 10:
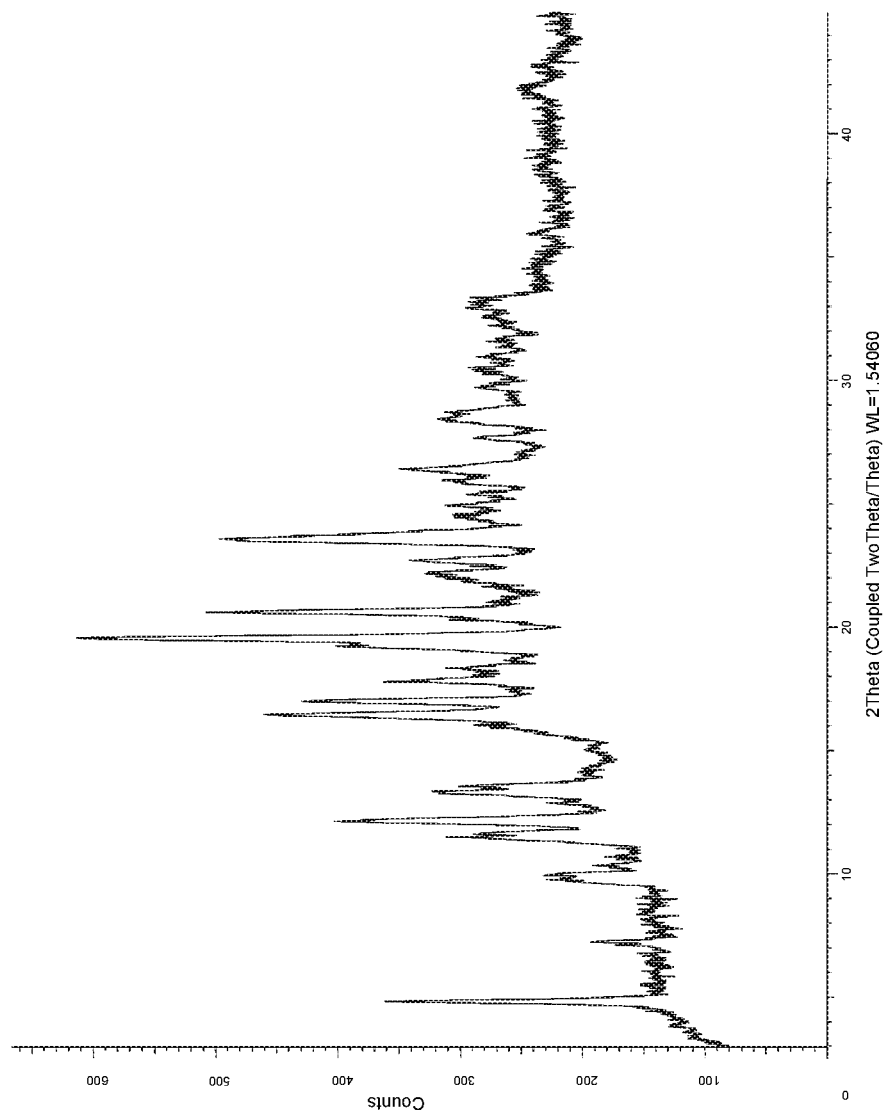
FIG. 10: shows an XRPD of (3S,4S)-8-(6-amino-5-((2-amino-3-chloropyridin-4-yl)thio)pyrazin-2-yl)-3-methyl-2-oxa-8-azaspiro[4.5]decan-4-amine succinate (2:1), hydrate, modification $H_B$.

Embodiment L: The inventions also relates to (3S,4S)-8-(6-amino-5-((2-amino-3-chloropyridin-4-yl)thio)pyrazin-2-yl)-3-methyl-2-oxa-8-azaspiro[4.5]decan-4-amine succinate (2:1), hydrate, modification $H_B$, (falling under formula I*) which is preferably characterized by 1, 2, 3 or more XRPD peaks having 2-theta values of 4.8, 12.1, 16.4, 17.0, 19.6, 20.6, 23.6 or as shown in the 2-theta table in Example 15. degrees, especially having an XRPD pattern as shown in FIG. 10, or by a DSC onset temperature at 171.7° C., or by any combination of these features.

Note in each case where 2-theta values are given (also in the Examples), they (in order to compensate for measurement errors) mean the respective values in degree 2 theta±0.5 degree 2-theta, more preferably ±0.2 degree 2-theta. Where 1, 2, 3 or more XRPD peaks are mentioned, the version with all peaks mentioned is most preferred.

The invention also relates to a pharmaceutical composition comprising a compound of the formula I*:

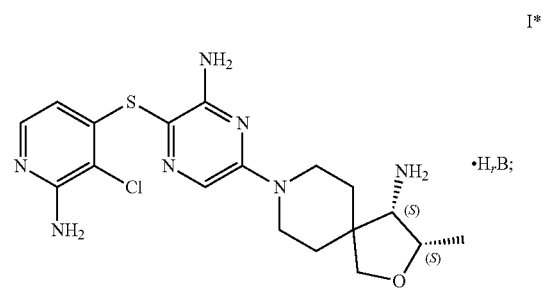

in which $H_rB$ is an acid selected from the group consisting of succinic acid (most preferred), hydrochloric acid, methylsulfonic acid, fumaric acid, and adipic acid, more preferably a salt or salt form mentioned in any one of embodiments A to K above, most preferably (3S,4S)-8-(6-amino-5-((2-amino-3-chloropyridin-4-yl)thio)pyrazin-2-yl)-3-methyl-2-oxa-8-azaspiro[4.5]decan-4-amine monosuccinate hydrated form $H_A$ as especially defined in Embodiment C above, together with at least pharmaceutically acceptable excipient.

The invention also relates to a method of treating a disease in an animal, especially human, in which modulation of SHP2 activity can prevent, inhibit or ameliorate the pathology and/or symptomology of the diseases, which method comprises administering to the animal (especially in need thereof) a therapeutically effective amount of a salt as mentioned in the preceding paragraph, alone or in simultaneous or sequential combination with another anti-cancer therapeutic.

The invention also relates to a salt or salt form as mentioned in any one of Embodiments A to K above for use in a method of treating a disease in an animal in which SHP2 activity can prevent, inhibit or ameliorate the pathology and/or symptomology of the disease, said method comprising administering said salt or salt form to a warm-blooded animal, especially a human patient.

The invention also relates to the use of a salt or salt form as mentioned in any one of Embodiments A to K above in the manufacture of a medicament for treating a disease in an animal, especially a human patient, in which SHP" activity contributes to the pathology and/or symptomology of the disease.

In all embodiments, succinate hydrated form $H_A$ is the most preferred salt form to implement.

In one embodiment, is a method for the manufacture of a compound of Formula I, or a pharmaceutically acceptable salt, acid co-crystal, hydrate or other solvate thereof, said method comprising reacting a compound of the formula II with a compound of the formula III according to the following reaction scheme;

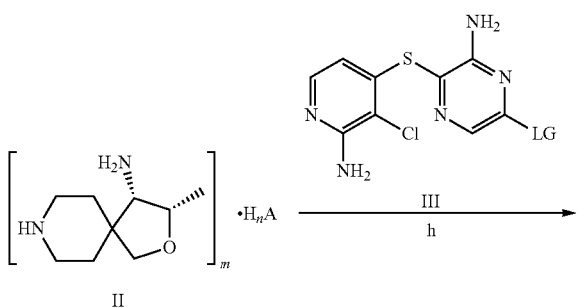

wherein A is the anion of an acid, LG is a leaving group, and n and m are integers selected from 1, 2 and 3 so that the compound of the formula II is electrically uncharged.

In a further embodiment, the method further comprises reacting a compound of formula IV with an acid of the formula $H_nA$ to yield the compound of the formula II according to the following reaction scheme:

wherein $R_1$ is a protecting group, HY is a chiral acid, A is the anion of an acid, and n and m are integers selected from 1, 2 and 3 so that the compound of the formula II is electrically uncharged.

In a further embodiment, the method further comprises reacting a compound of formula V, or a salt thereof, with a chiral acid of the formula HY to yield the compound of the formula IV according to the following reaction scheme:

wherein $R_1$ is a protecting group and HY is a chiral acid.

In a further embodiment, the method further comprises reacting a compound of formula VI to yield the compound of formula V according to the following reaction scheme;

wherein $R_1$ is a protecting group and $R_2$ is alkyl.

In a further embodiment, the method comprises reducing a compound of formula VII to yield the compound of formula VI according to the following reaction scheme:

wherein $R_1$ is a protecting group and $R_2$ is alkyl.

In a further embodiment, the method comprises reacting a compound of formula VIII with a compound of formula IX to yield the compound of formula VII according to the following reaction scheme:

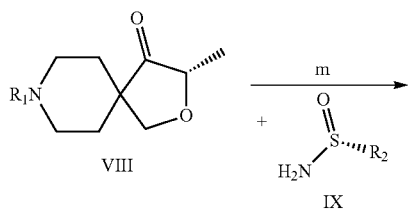 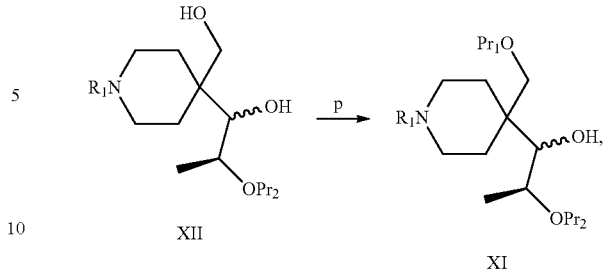

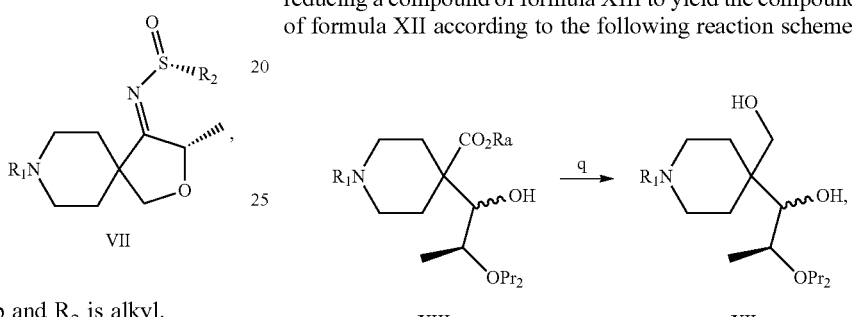

wherein $R_1$ is a protecting group, $PR_1O$ is a leaving group and $Pr_2$ is a substituted silyl protecting group.

In a further embodiment, the method further comprises reducing a compound of formula XIII to yield the compound of formula XII according to the following reaction scheme:

wherein $R_1$ is a protecting group and $R_2$ is alkyl.

In a further embodiment, the method further comprises oxidising a compound of formula X to yield a compound of formula VIII according to the following reaction scheme:

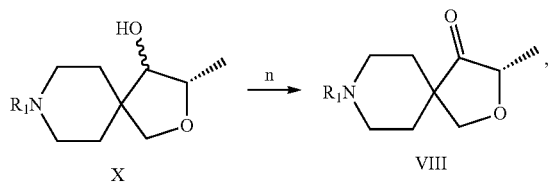

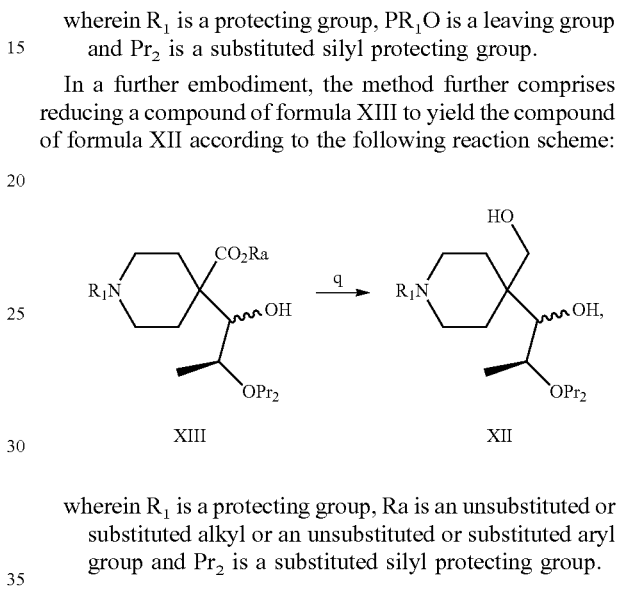

wherein $R_1$ is a protecting group.

In a further embodiment, the method further comprises cyclizing a compound of formula XI to yield a compound of formula X according to the following reaction scheme:

wherein $R_1$ is a protecting group, Ra is an unsubstituted or substituted alkyl or an unsubstituted or substituted aryl group and $Pr_2$ is a substituted silyl protecting group.

In a further embodiment, the method further comprises reacting a compound of formula XIV with a compound of formula XV to yield a compound of formula XIII according to the following reaction scheme:

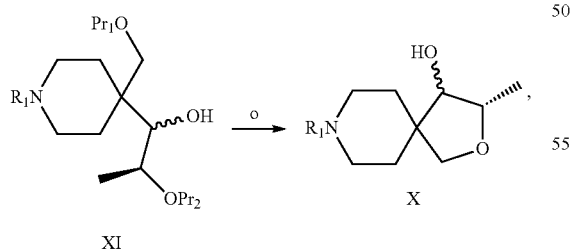

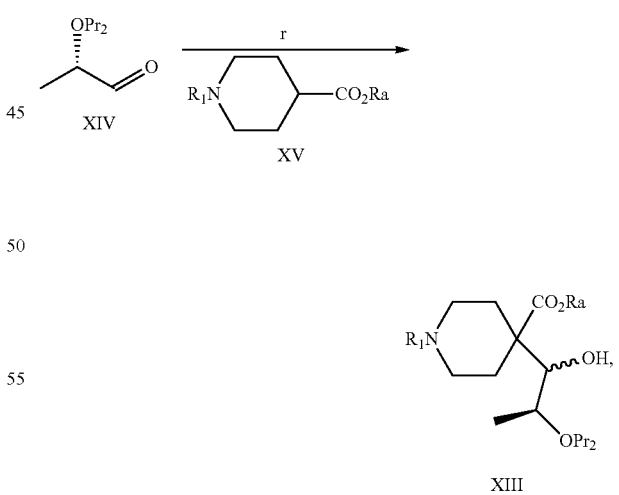

wherein $R^1$ is protecting group, $Pr_1O$ is a leaving group and $Pr_2$ is a substituted silyl protecting group.

In a further embodiment, the method comprises protecting a compound of formula XII with a compound of formula $Pr_1H$ to yield the compound of formula XI according to the following reaction scheme:

wherein $R_1$ is a protecting group, Ra is an unsubstituted or substituted alkyl or an unsubstituted or substituted aryl group and $Pr_2$ is a substituted silyl protecting group.

In a further embodiment, the method further comprises reducing a compound of formula XVI to yield the compound of formula XIV according to the following reaction scheme:

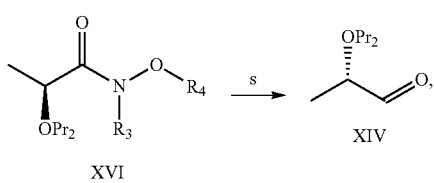

wherein $Pr_2$ is a substituted silyl protecting group, $R_5$ is an alkyl group and $R_4$ is an alkyl group.

In a further embodiment, the method further comprises reacting an ester compound of formula XVII with a compound of formula $R_4ONHR_3$ to yield the compound of formula XVI according to the following reaction scheme:

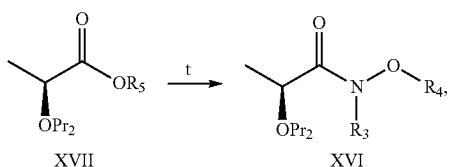

wherein $Pr_2$ is a substituted silyl protecting group, $R_3$ is an alkyl group, $R_4$ is an alkyl group and $R_5$ is an unsubstituted or substituted alkyl group or an unsubstituted or substituted aryl group.

In a further embodiment, the method further comprises protecting a compound of formula XVIII with a compound of formula $Pr_2HAL$ to yield the compound of formula XVII according to the following reaction scheme:

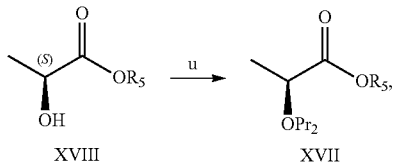

wherein $Pr_2$ is a substituted silyl protecting group, HAL is halo and $R_5$ is an unsubstituted or substituted alkyl group or an unsubstituted or substituted aryl group.

In another embodiment is a method comprising converting a compound of formula I in salt form or in free base form to an acid addition salt of formula I* with an inorganic or organic acid of formula $H_rB$ according to the following reaction scheme:

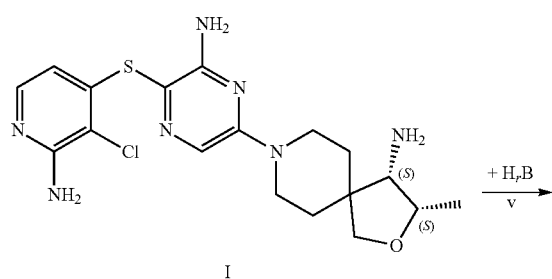

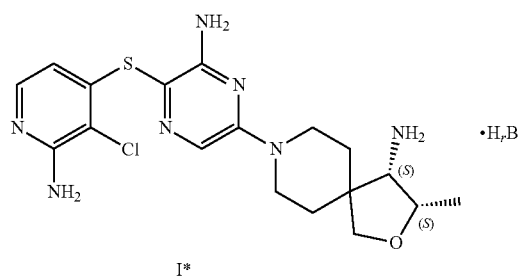

In another embodiment is a method of manufacturing a compound of formula III as defined in claim 1 comprising halogenating a compound of formula XVIII with a halogenating agent:

in which LG is a leaving group, to yield compound of formula XIX:

in which LG is a leaving group and Hal is halogen, which is then substituted with a mercapto compound of formula XX, $$R_6O-C(=O)-CH_2-CH_2-SH \quad (XX)$$

wherein $R_6$ is unsubstituted or substituted alkyl or unsubstituted or substituted aryl, to give a compound of formula XXI,

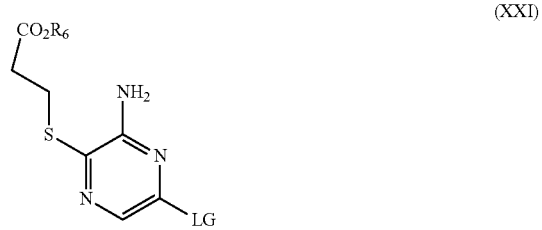

wherein LG is a leaving group and $R_6$ is unsubstituted or substituted alkyl or unsubstituted or substituted aryl; then treating the compound of formula XXI with an alkoxylate of an alkaline metal, to yield a compound of formula XXII,

(XXII)

wherein Mt is an alkaline metal, which compound of the formula XXII is then reacted with a compound of the formula XXIII:

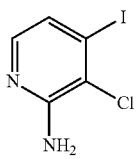

(XXIII)

to yield the compound of the formula III:

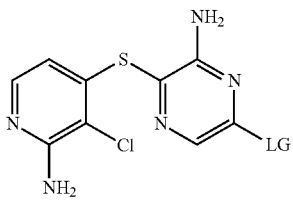

III wherein LG is a leaving group.

In another embodiment is a method of manufacturing a compound of formula XXIII;

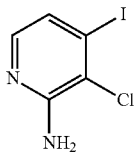

(XXIII)

comprising reacting a compound of formula XXIV:

(XXIV)

with iodine in the presence of a strong base; and treating the resulting compound of formula XXV:

(XXV)

with ammonia to yield the compound of formula XXIII.

In another embodiment is a compound of formula I*:

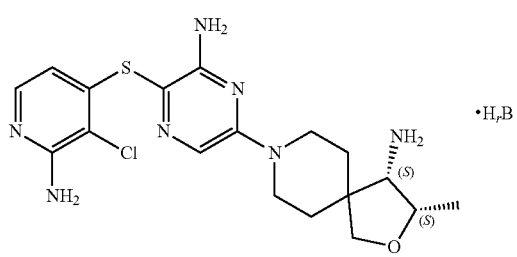

I*

·H$_r$B in which H$_r$B is an acid selected from the group consisting of succinic acid, hydrochloric acid, methylsulfonic acid, fumaric acid, and adipic acid, and at least one pharmaceutically acceptable carrier.

In a further embodiment, the compound is in crystalline form.

In another embodiment is (3S,4S)-8-(6-amino-5-((2-amino-3-chloropyridin-4-yl)thio)pyrazin-2-yl)-3-methyl-2-oxa-8-azaspiro[4.5]decan-4-amine monosuccinate free base in crystalline form.

In another embodiment is (3S,4S)-8-(6-amino-5-((2-amino-3-chloropyridin-4-yl)thio)pyrazin-2-yl)-3-methyl-2-oxa-8-azaspiro[4.5]decan-4-amine succinate (1:1) hydrated form H$_A$.

In another embodiment is (3S,4S)-8-(6-amino-5-((2-amino-3-chloropyridin-4-yl)thio)pyrazin-2-yl)-3-methyl-2-oxa-8-azaspiro[4.5]decan-4-amine hydrochloride. In a further embodiment, the compound is in crystalline form.

In a further embodiment is (3S,4S)-8-(6-amino-5-((2-amino-3-chloropyridin-4-yl)thio)pyrazin-2-yl)-3-methyl-2-oxa-8-azaspiro[4.5]decan-4-amine mesylate. In a further embodiment, the compound is in crystalline form.

In another embodiment is (3S,4S)-8-(6-amino-5-((2-amino-3-chloropyridin-4-yl)thio)pyrazin-2-yl)-3-methyl-2-oxa-8-azaspiro[4.5]decan-4-amine fumarate. In a further embodiment, the compound is in crystalline form.

In another embodiment is (3S,4S)-8-(6-amino-5-((2-amino-3-chloropyridin-4-yl)thio)pyrazin-2-yl)-3-methyl-2-oxa-8-azaspiro[4.5]decan-4-amine adipate. In a further embodiment, the compound is in crystalline form.

In another embodiment is (3S,4S)-8-(6-amino-5-((2-amino-3-chloropyridin-4-yl)thio)pyrazin-2-yl)-3-methyl-2-oxa-8-azaspiro[4.5]decan-4-amine, succinate (1:1) in anhydrous form.

In another embodiment is (3S,4S)-8-(6-amino-5-((2-amino-3-chloropyridin-4-yl)thio)pyrazin-2-yl)-3-methyl-2-oxa-8-azaspiro[4.5]decan-4-amine, succinate (2:1) hydrate.

In another embodiment is (3S,4S)-8-(6-amino-5-((2-amino-3-chloropyridin-4-yl)thio)pyrazin-2-yl)-3-methyl-2-oxa-8-azaspiro[4.5]decan-4-amine, succinate (2:1) anhydrate.

In another embodiment is a pharmaceutical composition comprising a compound of the formula I* according to any one of the above embodiments.

In a further embodiment, the compound of the formula I* is (3S,4S)-8-(6-amino-5-((2-amino-3-chloropyridin-4-yl)thio)pyrazin-2-yl)-3-methyl-2-oxa-8-azaspiro[4.5]decan-4-amine succinate (1:1) hydrated form $H_A$.

In another embodiment is a method of treatment comprising administering a compound of formula I* to a patient in need of such treatment in an effective amount for the prophylactic or therapeutic treatment of a disease or disorder which is mediated by the activity of SHP2.

In a further embodiment is a method of treatment comprising administering a compound of formula I* to a patient in need of such treatment in an effective amount for the prophylactic or therapeutic treatment of a disease or disorder which is mediated by the activity of SHF2, wherein the disease or disorder mediated by the activity of SHP2 is selected from Noonan Syndrome, Leopard Syndrome, juvenile myelomonocytic leukemias, neuroblastoma, melanoma, acute myeloid leukemia, breast cancer, esophageal cancer, lung cancer, colon cancer, head cancer, neuroblastoma, squamous-cell carcinoma of the head and neck, gastric carcinoma, anaplastic large-cell lymphoma and glioblastoma.

In another embodiment is a combination comprising a compound of the formula I* as defined in any one of the above embodiments, and one or more other pharmacologically active compounds, especially antiproliferative agents, for simultaneous, sequential or separate administration.

Pharmacology and Utility

The Src Homolgy-2 phosphatase (SHP2) is a protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 mediates activation of Erk1 and Erk2 (Erk1/2, Erk) MAP kinases by receptor tyrosine kinases such as ErbB1, ErbB2 and c-Met.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive conformation, inhibiting its own activity via a binding network involving residues from both the N-SH2 and PTP domains. In response to growth factor stimulation, SHP2 binds to specific tyrosine-phosphorylated sites on docking proteins such as Gab1 and Gab2 via its SH2 domains. This induces a conformational change that results in SHP2 activation.

Mutations in PTPN11 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-®), fibroblast growth factor (FGF-®) and epidermal growth factor (EGF-®). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

Noonan Syndrome (NS) and Leopard Syndrome (LS)-PTPN11 mutations cause LS (multiple lentigenes, electro-cardiogramduction abnormalities, ocular hypertelorism, pulmonic stenosis, abnormal genitalia, retardation of growth, sensorineural deafness) and NS (congenital anomalies including cardiac defects, craniofacial abnormalities and short stature). Both disorders are part of a family of autosomal dominant syndromes caused by germline mutations in components of the RAS/RAF/MEK/ERK mitogen activating protein kinase pathway, required for normal cell growth and differentiation. Aberrant regulation of this pathway has profound effects, particularly on cardiac development, resulting in various abnormalities, including valvuloseptal defects and/or hypertrophic cardiomyopathy (HCM). Perturbations of the MAPK signaling pathway have been established as central to these disorders and several candidate genes along this pathway have been identified in humans, including mutations in KRAS, NRAS, SOS1, RAF1, BRAF, MEK1, MEK2, SHOC2, and CBL. The gene most commonly mutated in NS and LS is PTPN11. Germline mutations in PTPN11 (SHP2) are found in ~50% of the cases with NS and nearly all patients with LS that shares certain features with NS. For NS, Y62D and Y63C substitutions in the protein are largely invariant and are among the most common mutations. Both these mutations affect the catalytically inactive conformation of SHP2 without perturbing the binding of the phosphatase to its phosphorylated signaling partners.

Juvenile Myelomonocytic Leukemias (JMML)-Somatic mutations in PTPN11 (SHP2) occur in about 35% of the patients with JMML, a childhood myeloproliferative disorder (MPD). These gain-of-function mutations are typically point mutations in the N-SH2 domain or in the phosphatase domain, which prevent self-inhibition between the catalytic domain and the N-SH2 domain, resulting in SHP2 activity.

Acute Myeloid Leukemia-PTPN11 mutations have been identified in: ~ 10% of pediatric acute leukemias, such as myelodysplastic syndrome (MDS); ~ 7% of B cell acute lymphoblastic leukemia (B-ALL); and ~4% of acute myeloid leukemia (AML).

NS and leukemia mutations cause changes in amino acids located at the interface formed by the N-SH2 and PTP domains in the self-inhibited SHP2 conformation, disrupting the inhibitory intramolecular interaction, leading to hyperactivity of the catalytic domain.

SHP2 acts as a positive regulator in receptor tyrosine kinase (RTK) signaling. Cancers containing RTK alterations (EGFR$^{amp}$, Her2$^{amp}$, FGFR$^{amp}$, Met$^{amp}$, translocated/activated RTK, i.e. ALK, BCR/ABL) include Esophageal, Breast, Lung, Colon, Gastric, Glioma, Head and Neck cancers.

Esophageal cancer (or oesophageal cancer) is a malignancy of the esophagus. There are various subtypes, primarily squamous cell cancer (<50%) and adenocarcinoma. There is a high rate of RTK expression in esophageal adenocarcinoma and squamous cell cancer. A SHP2 inhibitor of the invention can, therefore, be employed for innovative treatment strategies.

Breast cancer is a major type of cancer and a leading cause of death in women, where patients develop resistance to current drugs. There are four major subtypes of breast cancers including luminal A, luminal B, Her2 like, and triple negative/Basal-like. Triple negative breast cancer (TNBC) is an aggressive breast cancer lacking specific targeted therapy. Epidermal growth factor receptor I (EGFR) has emerged as a promising target in TNBC. Inhibition of Her2 as well as EGFR via SHP2 may be a promising therapy in breast cancer.

Lung Cancer—NSCLC is currently a major cause of cancer-related mortality. accounting for about 85% of lung cancers (predominantly adenocarcinomas and squamous cell carcinomas). Although cytotoxic chemotherapy remains an important part of treatment, targeted therapies based on genetic alterations such as EGFR and ALK in the tumor are more likely to benefit from a targeted therapy.

Colon Cancer—Approximately 30% to 50% of colorectal tumors are known to have a mutated (abnormal) KRAS, and BRAF mutations occur in 10 to 15% of colorectal cancers. For a subset of patients whose colorectal tumors have been demonstrated to over express EGFR, these patients exhibit a favorable clinical response to anti-EGFR therapy.

Gastric Cancer is one of the most prevalent cancer types. Aberrant expression of tyrosine kinases, as reflected by the aberrant tyrosine phosphorylation in gastric cancer cells, is known in the art. Three receptor-tyrosine kinases, c-met (HGF receptor), FGF receptor 2, and erbB2/neu are frequently amplified in gastric carcinomas. Thus, subversion of different signal pathways may contribute to the progression of different types of gastric cancers.

Neuroblastoma is a pediatric tumor of the developing sympathetic nervous system, accounting for about 8% of childhood cancers. Genomic alterations of the anaplastic lymphoma kinase (ALK) gene have been postulated to contribute to neuroblastoma pathogenesis.

Squamous-cell carcinoma of the head and neck (SCCHN). High levels of EGFR expression are correlated with poor prognosis and resistance to radiation therapy in a variety of cancers, mostly in squamous-cell carcinoma of the head and neck (SCCHN). Blocking of the EGFR signaling results in inhibition of the stimulation of the receptor, cell proliferation, and reduced invasiveness and metastases. The EGFR is, therefore, a prime target for new anticancer therapy in SCCHN.

The present invention relates to compound salts and salt forms capable of inhibiting the activity of SHP2.

In certain embodiments, the present invention relates to the aforementioned method and uses, wherein said SHP2-mediated disorders are cancers selected from, but not limited to: JMML; AML; MDS; B-ALL; neuroblastoma; esophageal; breast cancer; lung cancer; colon cancer; Gastric cancer, Head and Neck cancer. Other disorders are selected from: NS; LS; JMML; AML; MDS; B-ALL; neuroblastoma; esophageal; breast cancer; lung cancer; colon cancer; gastric cancer; head and neck cancer.

A SHP2 inhibitor of the present invention (especially of the formula I*, most preferably as described in any one of Embodiment A to K above) may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from antiporliferative agents, for example anti-cancer or chemotherapy agents, for example mitotic inhibitors such as a taxane, a vinca alkaloid, paclitaxel, docetaxel, vincristine, vinblastine, vinorelbine or vinflunine, and other anticancer agents, for example cisplatin, 5-fluorouracil or 5-fluoro-2-4 (1H,3H)-pyrimidinedione (5FU), flutamide or gemcitabine.

Such combinations may offer significant advantages, including synergistic activity, in therapy.

Pharmaceutical Compositions

In another aspect, the present invention provides pharmaceutically acceptable compositions which comprise a therapeutically-effective amount of one or more of the compound salts or forms described above, especially in embodiments A to K above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, for example, those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations (pharmaceutical compositions) of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In general, a suitable daily dose of a compound of the formula I* will be that amount of the compound which is the lowest dose effective to produce a therapeutic effect. Such an effective dose will generally depend upon the factors described above. Generally, oral, intravenous, intracerebroventricular and subcutaneous doses of the compounds of the formula I* for a patient, when used for the indicated analgesic effects, will range from about 0.0001 to about 100 mg per kilogram of body weight per day.

If desired, the effective daily dose of the active compound of the formula I* (or any combination partner) may be administered as two, three, four, five, six or more sub-doses administered separately at appropriate intervals throughout the day, optionally, in unit dosage forms. Preferred dosing is one administration per day.

In certain embodiments, a formulation of the present invention comprises an excipient selected from the group consisting of cyclodextrins, celluloses, liposomes, micelle forming agents, for example, bile acids, and polymeric carriers, for example, polyesters and polyanhydrides; and a compound of the present invention. In certain embodiments, an aforementioned formulation renders orally bioavailable a compound of the formula I*.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the formula I* as an active ingredient. A compound of the formula I* may also be administered as a bolus, electuary or paste.

In solid dosage forms of the invention for oral administration (capsules, tablets, pills, dragees, powders, granules, trouches and the like), the active ingredient (a salt or salt form especially as described in Embodiments A to K above) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The term "treatment" or "treating" is in particular intended to encompass also prophylaxis, therapy and cure.

Pharmaceutical Combinations

The invention especially relates to the use of a compound of the formula I*, especially as defined in Embodiment A to K above, in the treatment of one or more of the diseases mentioned herein; wherein the response to treatment is beneficial as demonstrated, for example, by the partial or complete removal of one or more of the symptoms of the disease up to complete cure or remission.

A compound of formula (I*) can especially also be used in combination with any one or more of the following drug compounds and treatments;

BCR-ABL inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and N-[2-[(1S,4®)-6-[[4-(Cyclobutylamino)-5-(trifluoromethyl)-2-pyrimidinyl]amino]-1,2,3,4-tetrahydronaphthalen-1,4-imin-9-yl]-2-oxoethyl]-acetamide (PF-03814735, CAS 942487-16-3).

ALK inhibitors: PF-2341066 (XALKORI®; crizotinib); 5-chloro-N4-(2-(isopropylsulfonyl)phenyl)-N2-(2-methoxy-4-(4-(4-methylpiperazin-1-yl) piperidin-1-yl) phenyl)pyrimidine-2,4-diamine; GSK1838705A; and CH5424802.

BRAF inhibitors: Vemurafanib (PLX4032); LGX818 and Dabrafenib.

FLT3 inhibitors—sunitinib malate (sold under the tradename Sutent® by Pfizer); PKC412 (midostaurin); tanutinib, sorafenib, sunitinib, midostaurin, lestaurtinib, KW-2449, quizartinib (AC220) and crenolanib.

MEK Inhibitors—trametinib.

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)-(®)-1-(4-(4-Fluoro-2-methyl-1H-indol-5-yloxy)-5-methylpyrrolo[2,1-f][1,2,4]triazin-6-yloxy) propan-2-yl)$_2$-aminopropanoate, also known as BMS-582664), motesanib (N-(2,3-dihydro-3,3-dimethyl-1H-indol-6-yl)-2-[(4-pyridinylmethyl) amino]-3-pyridinecarboxamide, and described in PCT Publication No. WO 02/066470), pasireotide (also known as SOM230, and described in PCT Publication No. WO 02/010192), sorafenib (sold under the tradename Nexavar®);

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl) methoxy]phenyl]amino]-3-cyano-7-ethoxyquinolin-6-yl]-4-(dimethylamino) but-2-enamide, and described PCT Publication No. WO 05/028443), lapatinib or lapatinib ditosylate (sold under the trademark Tykerb® by GlaxoSmithKline); Trastuzumab emtansine (in the United States, ado-trastuzumab emtansine, trade name Kadcyla)—an antibody-drug conjugate consisting of the monoclonal antibody trastuzumab (Herceptin) linked to the cytotoxic agent mertansine (DM1);

CD20 antibodies: Rituximab (sold under the trademarks Riuxan® and MabThera® by Genentech/Roche), tositumomab (sold under the trademarks Bexxar® by GlaxoSmithKline), ofatumumab (sold under the trademark Arzerra® by GlaxoSmithKline);

Tyrosine kinase inhibitors: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl) urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl) propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis);

DNA Synthesis inhibitors: Capecitabine (sold under the trademark Xeloda® by Roche), gemcitabine hydrochloride (sold under the trademark Gemzar® by Eli Lilly and Company), nelarabine ((2S,3S,4R,5R)-2-(2-amino-6-methoxy-purin-9-yl)-5-(hydroxymethyl)oxolane-3,4-diol, sold under the tradenames Arranon® and Atriance® by GlaxoSmithKline);

Antineoplastic agents: oxaliplatin (sold under the tradename Eloxatin® ay Sanofi-Aventis and described in U.S. Pat. No. 4,169,846);

Epidermal growth factor receptor (EGFR) inhibitors: Gefitnib (sold under the tradename Iressa®), N-[4-[(3-Chloro-4-fluorophenyl)amino]-7-[[(3"S")-tetrahydro-3-furanyl]oxy]-6-quinazolinyl]-4 (dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen);

HER dimerization inhibitors: Pertuzumab (sold under the trademark Omnitarg®, by Genentech);

Human Granulocyte colony-stimulating factor (G-CSF) modulators: Filgrastim (sold under the tradename Neupogen® by Amgen);

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C$_6$, available from Seattle Genetics, Inc);

Pro-apoptotic receptor agonists (PARAs): Dulanermin (also known as AMG-951, available from Amgen/Genentech);

Hedgehog antagonists; 2-chloro-N-[4-chloro-3-(2-pyridinyl)phenyl]-4-(methylsulfonyl)-benzamide (also known as GDC-0449, and described in PCT Publication No. WO 06/028958);

PI3K inhibitors; 4-[2-(1H-Indazol-4-yl)-6-[[4-(methylsulfonyl) piperazin-1-yl]methyl]thieno[3,2-d]pyrimidin-4-yl]morpholine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806);

Phospholipase A2 inhibitors: Anagrelide (sold under the tradename Agrylin®);

BCL-2 inhibitors; 4-[4-[[2-(4-chlorophenyl)-5,5-dimethyl-1-cyclohexen-1-yl]methyl]-1-piperazinyl]-N-[[4-[[(1®)-3-(4-morpholinyl)-1-[(phenylthio)methyl]propyl]amino]-3-[(trifluoromethyl) sulfonyl]phenyl] sulfonyl]benzamide (also known as ABT-263 and described in PCT Publication No. WO 09/155386);

Mitogen-activated protein kinase kinase (MEK) inhibitors: XL-518 (Cas No. 1029872-29-4, available from ACC Corp.);

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®);

mTOR inhibitors: Temsirolimus (sold under the tradename Torisel® by Pfizer), ridaforolimus (formally known as deferolimus, (1R,2R,4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis);

Osteoclastic bone resorption inhibitors; 1-Hydroxy-2-imidazol-1-yl-phosphonoethyl)phosphonic acid monohydrate (sold under the tradename Zometa® by Novartis);

CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.)

CD20 Antibody Drug Conjugates: Ibritumomab tiuxetan (sold under the tradename Zevalin®);

Somatostain analogs: octreotide (also known as octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor κ B (RANK) inhibitors: Denosumab (sold under the tradename Prolia® by Amgen);

Thrombopoietin mimetic peptibodies: Romiplostim (sold under the tradename Nplate® by Amgen;

Cell growth stimulators: Palifermin (sold under the tradename Kepivance® by Amgen);

Anti-Insulin-like Growth Factor-1 receptor (IGF-1®) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

CTLA-4 inhibitors: Tremelimumab (IgG2 monoclonal antibody available from Pfizer, formerly known as ticilimumab, CP-675,206), ipilimumab (CTLA-4 antibody, also known as MDX-010, CAS No. 477202-00-9);

PD1 inhibitors: Nivolumab (also referred to herein as MDX-1106, MDX-1106-04, ONO-4538, BMS0936558, CAS Registry No; 946414-94-4) disclosed in, for example, U.S. Pat. No. 8,008,449, and having a sequence disclosed therein (or a sequence substantially identical or similar thereto, for example, a sequence having at least 85%, 90%, 95% identity or greater to the sequence specified in U.S. Pat.

No. 8,008,449); Pembrolizumab (also referred to herein as Lambrolizumab, MK-3475, MK03475, SCH-900475 or KEYTRUDA), disclosed in, for example, U.S. Pat. No. 8,354,509 and WO 2009/114335, and having a sequence disclosed therein (or a sequence substantially identical or similar thereto, for example, a sequence having at least 85%, 90%, 95% identity or greater to the sequence specified in U.S. Pat. No. 8,354,509 and WO2009/114335); an immunoadhesin (for example, an immunoadhesin comprising an extracellular or PD-1 binding portion of PD-L1 or PD-L2 fused to a constant region (for example, an Fc region of an immunoglobulin sequence); Pidilizumab (CT-011; Cure Tech) is a humanized IgG1k monoclonal antibody that binds to PD1 (Pidilizumab and other humanized anti-PD-1 monoclonal antibodies are disclosed in WO2009/101611); and AMP-224 (B7-DCIg; Amplimmune), disclosed in WO2010/027827 and WO2011/066342), is a PD-L2 Fc fusion soluble receptor that blocks the interaction between PD1 and B7-H1; other PD-1 inhibitors, for example, anti-PD1 antibodies disclosed in U.S. Pat. No. 8,609,089, US 2010028330, and/or US20120114649.

PDL1 inhibitors: MSB0010718C (also referred to as A09-246-2; Merck Serono) is a monoclonal antibody that binds to PD-L1 and is disclosed in, for example, WO 2013/0179174, (and having a sequence substantially identical or similar thereto, for example, a sequence having at least 85%, 90%, 95% identity or higher to the sequence specified in WO 2013/0179174); and anti-PD-L1 binding antagonist selected from YW243.55.S70, MPDL3280A (Genetech/Roche) is a human Fc optimized IgG1 monoclonal antibody that binds to PD-L1 (MDPL3280A and other human monoclonal antibodies to PD-L1 are disclosed in U.S. Pat. No. 7,943,743 and U.S Publication No.: 20120039906); MEDI-4736, MSB-0010718C, or MDX-1105 (MDX-1105, also known as BMS-936559, is an anti-PD-L1 antibody described in WO2007/005874; antibody YW243.55.S70 is an anti-PD-L1 described in WO 2010/077634).

LAG-3 inhibitors: BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

GITR agonists: exemplary GITR agonists include, for example, GITR fusion proteins and anti-GITR antibodies (for example, bivalent anti-GITR antibodies), such as, a GITR fusion protein described in U.S. Pat. No. 6,111,090, European Patent No.; 090505B1, U.S. Pat. No. 8,586,023, PCT Publication Nos.: WO 2010/003118 and 2011/090754, or an anti-GITR antibody described, for example, in U.S. Pat. No. 7,025,962, European Patent No.; 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

Histone deacetylase inhibitors (HDI): Voninostat (sold under the tradename Zolinza® by Merck).

anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

anti-TIM-3 antibody or antigen-binding fragment thereof.

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®);

Biologic response modifiers: bacillus calmette-guerin (sold under the tradenames theraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also know as MK-0822, N-(1-cyanocyclopropyl)-4-fluoro-$N^2$—{(1S)-2,2,2-trifluoro-1-[4'-(methylsulfonyl) biphenyl-4-yl]ethyl}-L-leucinamide, available from Lanzhou Chon Chemicals, ACC Corp., and ChemieTek, and described in PCT Publication no. WO 03/075836).

Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989);

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis);

Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

Proteasome inhibitors: Bortezomib (sold under the tradename Velcade®);

CDK1 inhibitors: Alvocidib (also known as flovopirdol or HMR-1275, 2-(2-chlorophenyl)-5,7-dihydroxy-8-[(3S, 4R)-3-hydroxy-1-methyl-4-piperidinyl]-4-chromenone, and described in U.S. Pat. No. 5,621,002);

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-7β,10β-dimethoxy-9-oxo-5β,20-epoxytax-11-ene-2α,4,13α-triyl-4-acetate-2-benzoate-13-[(2S,3S)-3-{[(tert-butoxy)carbonyl]amino}-2-hydroxy-3-phenylpropanoate), larotaxel ((2α,3ξ,4α,5β,7α,10β,13α)-4, 10-bis(acetyloxy)-13-({(2S,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate);

5HT1a receptor agonists: Xaliproden (also known as SR57746, 1-[2-(2-naphthyl)ethyl]-4-[3-(trifluoromethyl)phenyl]-1,2,3,6-tetrahydropyridine, and described in U.S. Pat. No. 5,266,573);

HPC vaccines: Cervarix® sold by GlaxoSmithKline, Gardasil® sold by Merck; Iron Chelating agents: Deferasinox (sold under the tradename Exjade® by Novartis);

Anti-metabolites: Claribine (2-chlorodeoxyadenosine, sold under the tradename leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodim (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®);

Demethylating agents; 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), paclitaxel (sold under the tradenames Taxol and Onxal™);

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®);

Estrogen receptor downregulators: Fulvestrant (sold under the tradename Faslodex®); and LSZ102;

Anti-estrogens: tamoxifen (sold under the tradename Novaldex®);

Toremifene (sold under the tradename Fareston®);

Selective estrogen receptor modulators (SERMs): Raloxifene (sold under the tradename Evista®);

Luteinizing hormone releasing hormone (LHRH) agonists: Goserelin (sold under the tradename Zoladex®);

Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®);

A compound of formula (I*) can also be used in combination with the following adjunct therapies;

Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

Immune checkpoint inhibitors: In one embodiment, the combination therapies disclosed herein include an inhibitor of an inhibitory molecule of an immune checkpoint molecule. The term "immune checkpoints" refers to a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells, immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In embodiments, an inhibitory nucleic acid (for example, a dsRNA, siRNA or shRNA), can be used to inhibit expression of an inhibitory molecule. In other embodiments, the inhibitor of an inhibitory signal is, a polypeptide for example, a soluble ligand, or an antibody or antigen-binding fragment thereof, that binds to the inhibitory molecule.

In certain embodiments, the anti-PD-1 molecules of formula I* described herein are administered in combination with one or more other inhibitors of PD-1, PD-L1 and/or PD-L2 known in the art. The antagonist may be an antibody, an antigen binding fragment thereof, an immunoadhesin, a fusion protein, or oligopeptide.

EXAMPLES

The following examples (which are also specific invention embodiments) serve to illustrate the invention without limiting the scope otherwise defined herein. Abbreviations used: Ac (acetyl or acetate); ACN (acetonitrile); Boc (tert-butoxycarbonyl); Brine (sodium chloride solution saturated at room temperature); Bu (butyl); Dba (dibenzylideneacetone); DCM (dichloromethane); DIPEA (Di(isopropyl)ethylamine); DMAc (N,N-Dimethylacetamide); DMP (Dess-Martin periodinane); DMSO (dimethylsulfoxide); Dppf (diphenylphosphino); EA (ethyl acetate); ee (enantiomeric excess); Ent (enantiomer); Eq or eq (equivalent(s)); Equiv (equivalent(s)); Et (ethyl); GC (gas chromatography); hr(s) (hour(s)); HPLC (High Performance Chromatography); IPA (isopropyl alcohol); IPAc (isopropyl acetate); IT (Internal temperature (in a reaction mixture)); L (liter(s)); LDA (lithium diisopropylamide); LiHMDS (Lithium bis(trimethylsilyl)amide); LOQ (Limit of Qunatification); Me (methyl); Me-THF (2-methyltetrahydrofuran); MTBE (methyl tert-butyl ether); NBS (N-bromosuccinimide); NMR (Nuclear Magnetic Resonance); qnmr (quantitative NM®); $^i$Pr or IP (isopropyl); PSC-1, 2, etc., (Process steering control-1); Rt or RT (room temperature (about 20 to about 23° C.); sat (saturated (at RT)); TBS (tert-butyl-dimethylsilyl); TBSCl (Tert-butyldimethylsilylchloride); THF (tetrahydrofuran); TLC (Thin Layer Chromatography); TsCl (Tosylchloride); V (Volume(s)); and Xantphos (4,5-Bis(diphenylphosphino)-9,9-dimethylxanthene).

Experimental Procedures:

XRPD (X-ray powder diffraction) data were obtained as follows, using the reflection mode: Diffraction pattern were obtained on a Bruker D8 Advance system in reflection mode using zero-background SI-sample holders. Samples were measured at room temperature without sample spinning. Data were acquired between 2° and 40° C. 2theta, with a step width of 0.017° and a step time of 0.3s. Diffraction peak positions were calculated using the system evaluation software.

DSC (Differential Scanning calorimetry)/TGA (Thermogravimetric Analysis) data wee obtained as follows: Thermal analysis was performed using DSC or TGA. The DSC and TGA systems were a TA-Instruments Discovery. For the DSC, approximately 2-4 mg of sample was prepared in an aluminum crucible with pin-hole lid. Using a heating rate of 10° C./min the thermal behavior was determined between 30° C., and 300° C. The same heating rate and temperature range were applied for the TGA, whereby approximately 5-15 mg of sample were filled into a sealed A1-crcible that was pierced automatically by the robotic autosampler before measurement. Melting onset and enthalpies as well as weight losses with respect to temperature were determined using the system evaluation software.

DVS/Dynamic Vapor Sorption) data were obtained as follows: Dynamic vapor sorption was performed using a SMS Advantage system. Approximately 10 mg of sample was subjected to varying humidities between 0% RH and 95% RH at 25° C. Evaluation was performed using the system software.

Example 1

Method of synthesis of the compound of the formula I ((3S,4S)-8-(6-amino-5-((2-amino-3-chloropyridin-4-yl)thio)pyrazin-2-yl)-3-methyl-2-oxa-8-azaspiro[4.5]decan-4-amine);

The overall synthesis can be described by the following Reaction Scheme A:

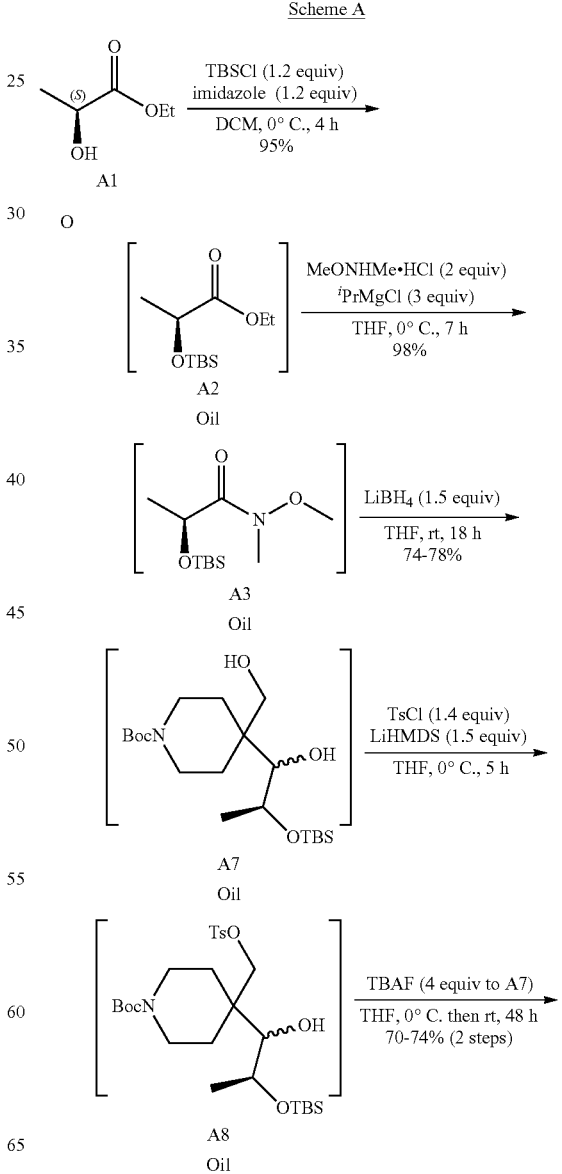

-continued

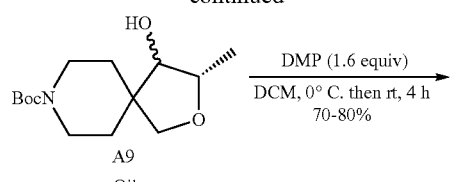

A9
Oil

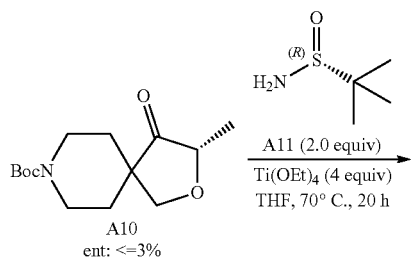

A10
ent: <=3%
solid

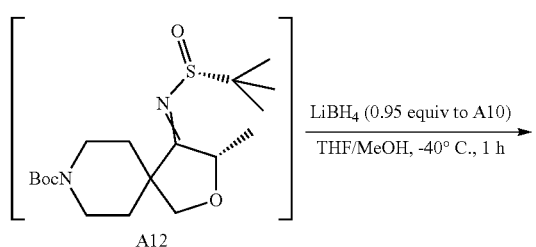

A12

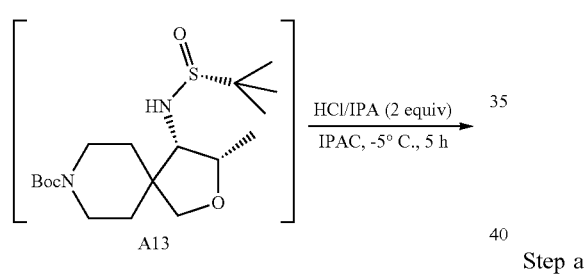

A13

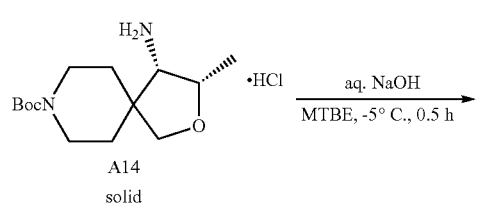

A14
solid

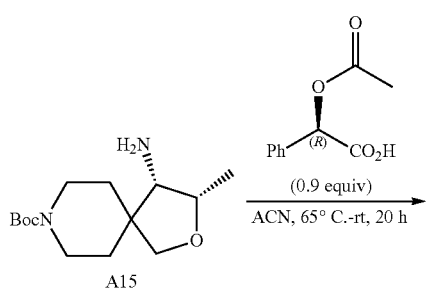

A15

-continued

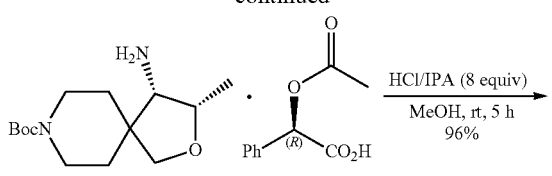

A16
45-47% from A10
ent: <0.1%
diastereoisomers: <=0.74%

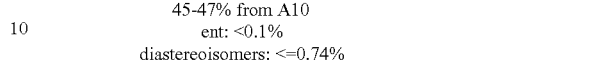

A17
diastereoisomers: <=0.5%
(confirmed at A18 R.X. mixture)
Solid

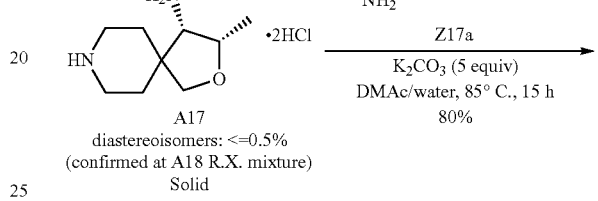

A18
diastereoisomer 1 <LOQ
diastereoisomer 2 <=0.17%
Solid

Step a

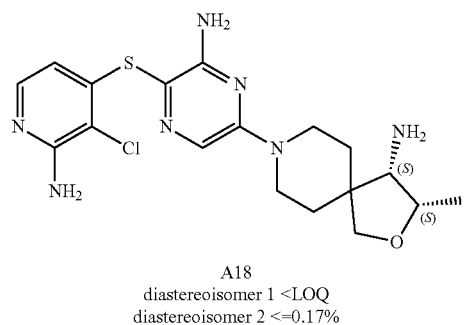

A1
$C_4H_8O_3$
MW: 104.11

A2
$C_{10}H_{22}O_3Si$
MW: 218.37

To a solution of A1 (10.4 kg, 100 mol, 1.0 Eq) in $CH_2Cl_2$ (50 L) was added imidazole (8.16 kg, 120 mol, 1.2 eq) and TBSCl (18 kg, 120 mol, 1.2 Eq) at 0° C. After addition, the mixture was stirred at 0° C. for 4 h. GC showed the reaction was finished. (A1/(A1+A2)<1%). The reaction mixture was quenched with saturated $NaHCO_3$ (14L) at 0-5° C. Phases were separated. The organic phase was washed with brine (14L). The organic layer was dried over $Na_2SO_4$, concentrated under vacuum at 40-45° C. to afford A2 (23.3 kg, assay 88%, yield 94%) which was used for the next step directly. $^1$H NMR (400 MHZ, CDCl3) δ=4.35 (d, J=8.8 Hz, 1H), 3.74 (s, 3H), 2.48 (s, J=8.8 Hz, 3H), 0.93 (s, 9H), 0.09 (s, 6H).

Step b

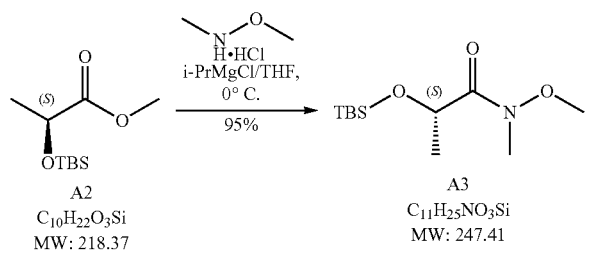

To a solution of A2 (7.5 kg, 34.3 mol, 1.0 Eq) and N,O-dimethylhydroxylamine hydrochloride (6.69 kg, 68.6 mol, 2.0 Eq) in THF (20 L) was added drop-wise a solution of chloro(isopropyl) magnesium (2 M, 51.45 L, 3.5 Eq) at 0° C. under $N_2$ over 5-6 h. After addition, the reaction mixture was stirred at 0° C. for 1 h, GC showed the reaction was finished (A2/(A2+A3)<2%). The mixture was quenched with $NH_4Cl$ (25 L) slowly by keeping the temperature at 0-5° C. After addition, the reaction mixture was stirred for 30 min. Phase was separated. The aqueous layer was extracted with EA (2×20 L). The combined organic phase was washed with brine (25L), dried over $Na_2SO_4$, concentrated to give A3 (9.4 kg, assay 86%, yield 95%) which was used for the next step directly. $^1$H NMR (400 MHZ, $CDCl_3$) δ=4.67 (m, J=6.6 Hz, 1H), 3.70 (s, 3H), 3.21 (s, 3H), 3.17 (d, 3H) 2.48 (s, J=6.6 Hz, 3H), 0.90 (s, 9H), 0.10 (s, 3H), 0.08 (s, 3H), Step c

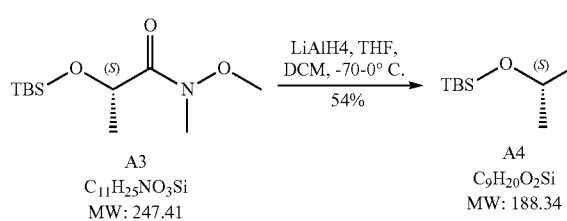

To a solution of A3 (7.1 kg, assay 86%, 24.65 mol, 1.0 Eq) in DCM (30 L) was added dropwise a solution of $LiAlH_4$ (2.4 M, 11.3 L, 1.1 Eq) at −70° C. under $N_2$. Then the reaction mixture was stirred at −70° C. for 3 h, and TLC showed the reaction was finished (PSC-1). The mixture was warmed to 0° C., and then quenched with sat. potassium sodium tartrate (35 L) at 0° C. After addition, DCM (20L) was added and stirred for 2 h at 20-25° C. Phases were separated. The aqueous layer was extracted with DCM (25 L). The combined organic phase was charged with sat. citric acid (45L) and stirred at 0° C. for 8 h. Phase was separated. The organic phase was washed with $NaHCO_3$ (25L), brine (25 L), dried over $Na_2SO_4$, and the solvent was removed under vacuum at 25-30° C., n-Heptane (10 L) was added to the residue and concentrated under vacuum at 30-35° C., n-Heptane (10 L) was added to the residue again and concentrated under vacuum at 30-35° C. to give A4 (4.2 kg, assay 60%, yield 54%) which was used for the next step directly.

Step d

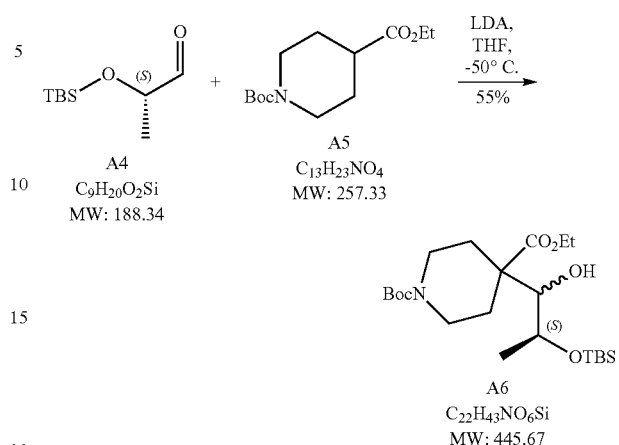

To a solution of diisopropylamine (3.06 kg, 30.3 mol, 1.5 eq) in THF (20 L) cooled to approximately −10° C. was added 2.5 M n-BuLi (12.12 L, 30.3 mol, 1.5 eq) under $N_2$. The resulting mixture was stirred at approximately −10° C. for 30 min, then a solution of A5 (5.2 kg, 20.20 mol, 1.0 eq) in THF (10 L) was added slowly. After addition, the reaction mixture was stirred at −10° C. for 30 min, and then cooled to −50° C. A4 (4.18 kg, 22.22 mol, 1.1 eq) was added dropwise. After addition, the reaction mixture was stirred at −50° C. for 30 min. The mixture was quenched with saturated aqueous $NH_4Cl$ (30L) and water (10L) at −50° C. The reaction mixture was warmed to 20-25° C. Phase was separated. The aqueous phase was extracted with EA (3×20 L). All organic phases were combined and washed with brine (20L), then concentrated to a yellow oil which was purified by column (silica gel, 100-200 mesh, eluted with n-heptane: EA from 50:1 to 10:1) to give A6 (5.5 kg, assay 90%, yield 55%) as pale yellow oil. $^1$H NMR (400 MHz, $CDCl_3$) δ=4.35-4.15 (m, 2H), 3.95-3.74 (m, 3H), 3.52 (m, 2H), 2.67 (m, 2H), 2.12-1.98 (m, 2H), 1.75-1.52 (m, 4H), 1.49 (s, 9H), 1.35-1.10 (m, 6H), 0.98 (s, 9H), 0.02 (s, 6H).

Step e

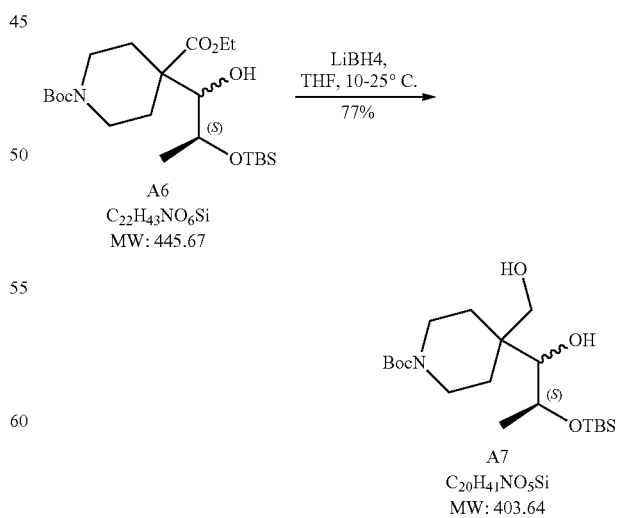

To a solution of A6 (11.4 kg, 25.58 mol, 1.0 eq) in THF (60 L) was added $LiBH_4$ (836 g, 38.37 mol, 1.5 eq) in portions at 5-10° C., and the reaction mixture was stirred at 20-25° C. for 18 h. HPLC showed the reaction was finished (A6/(A6+A7)<2%). The mixture was cooled to 10° C., and slowly quenched with saturated NaHCO₃ solution (15 L) and water (25L) with vigorously stirring. After gas formation stopped, vacuum filtration was applied to remove solids. The solid was washed with EA (2×15 L). Phase was separated; the aqueous phase was extracted with EA (3×15L). All organic phases were combined and washed with brine (15L), and concentrated to obtain crude A7 (13.8 kg, assay 58%, yield 77%) which was used for the next step directly.

Step f

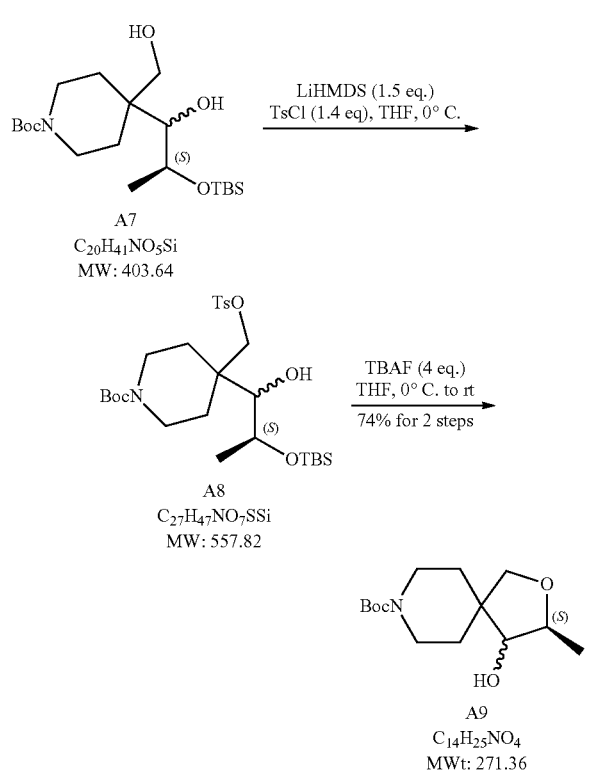

To a solution of A7 (8 kg, 19.82 mol, 1.0 eq) in THF (40 L) under nitrogen atmosphere was added TsCl (5.28 kg, 27.75 mol, 1.4 eq) at 10-15° C. After addition, the mixture was cooled to 0° C., and 1M LiHMDS (29.7 L, 29.73 mol, 1.5 eq) was added dropwise during 2 h. After addition, the mixture was stirred at 0° C. for 3 h. HPLC showed the reaction was finished (PSC-1 A7/(A7+A8)<7%). TBAF (20.72 kg, 65.67 mol, 3.3 eq) was added into the mixture at 0° C., and the reaction mixture was stirred at 25-30° C. for 48 h. HPLC showed the reaction was finished (PSC-2, A9-intermedaite/(A9-intermediate+A9)<2%). The mixture was quenched with saturated aqueous sodium bicarbonate solution (32L) and stirred for 30 min at 0° C. Phase was separated, and the aqueous phase was extracted with EA (3×20 L). The combined organic phase was washed with brine (20 L), dried over Na₂SO₄, and concentrated to a yellow oil which was purified by column (eluted with n-heptane: EA from 10:1 to 1:1) to give A9 (4.42 kg, assay 90%, yield 74%) as pale yellow solid.

Step g

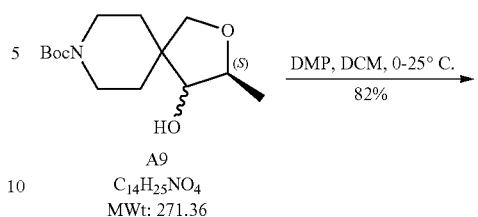

To a solution of A9 (4.0 kg, 14.74 mol, 1.0 eq) in DCM (40 L) cooled on an ice-bath was added DMP (9.36 kg, 23.58 mol, 1.6 eq) in portions, and it resulted in a suspension. After addition, the mixture stirred for 4 hours at 20-25° C. HPLC showed the reaction was finished (A9/(A9+A10)<2%). DCM (30L) was added at 0° C. After addition, the mixture was quenched with saturated aqueous Na₂SO₃ (20 L). The mixture was stirred for 30 min at 0° C., filtered and the white solid was washed with DCM (2×15L). Phase was separated, and the organic phase was cooled to 0° C., to which was added saturated aqueous NaHCO₃ (20L) and stirred for 1 h. Phase was separated, and the organic phase was washed with brine (25L), dried over Na₂SO₄, and concentrated to a yellow oil which was purified by column (eluted with n-heptane: EA from 50:1 to 10:1) to give A10 (3.70 kg, assay 88%, ee value 95.3%, yield 82%) as white solid. ¹H NMR (400 MHZ, DMSO-d6) δ=4.20 (d, J=8.0 Hz, 1H), 3.98-3.67 (m, 4H), 3.08-2.90 (m, 2H), 1.54-1.39 (m, 13H), 1.18 (d, J=8.0 Hz, 3H).

Step h

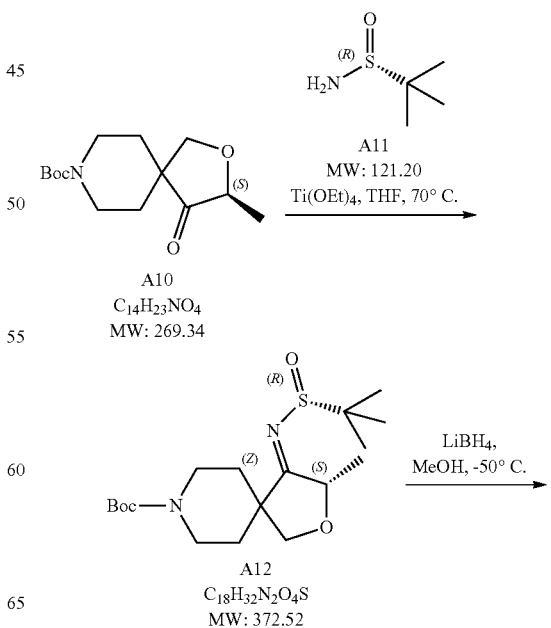

-continued

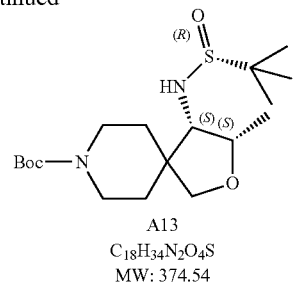

A13
C₁₈H₃₄N₂O₄S
MW: 374.54

To a solution of A10 (4.60 kg, 17.08 mol, 1.0 eq) in THF (40 L) was added Ti(OEt)₄ (15.58 kg, 68.32 mol, 4.0 eq) and (R)-t-Butyl sulfinamide (4.14 kg, 34.16 mol, 2.0 eq) at 25° C. After addition, the mixture was heated to 70° C., and stirred for 20 h. HPLC showed the reaction was finished (PSC-1, A10/(A10+A12)<4%). The mixture was cooled to −30--40° C., and MeOH (4 L) was added dropwise within 30 min and stirred for 1 h. 2M LiBH₄ (8.1 L) solution was added dropwise to the reaction mixture at −40--50° C., and stirred for 1 h. HPLC indicated all of imine was consumed (PSC-2, A12/(A12+A13)<1%). The mixture was warmed to −30° C., and stirred for 1 h, then warmed to 0° C. within 2 h and stirred for 1 h, then warmed to 20-25° C., and stirred for 30 min. IPAC (25L) was added to above mixture, NaHCO₃ (5L) was added dropwise in about 1 h at 25° C., and stirred for 30 min. The mixture was filtered under vacuum and the cake was washed with IPAC (8×15L). The combined organic phase was washed with brine (25L), then evaporated under vacuum to get a solution of A13 (about 28 kg) which was used for next step.

Step i

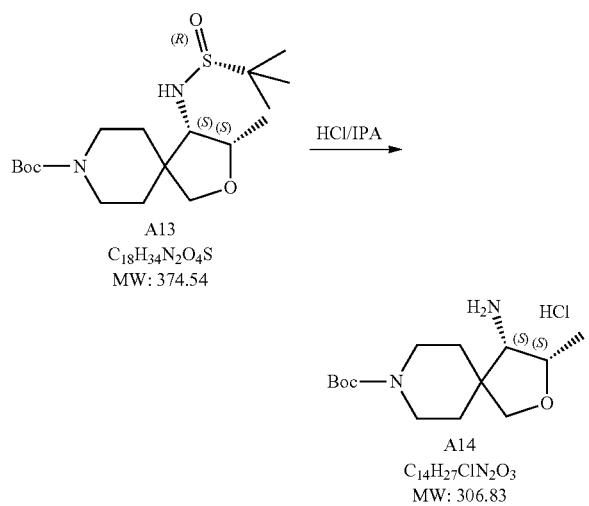

To a mixture of A13 in IPAC (about 28 kg, 17.08 mol, 1.0 eq) was added dropwise 4M HCl/IPA (8.54 L, 34.16 mol, 2.0 eq) at −5° C., and stirred for 5 h at −5° C. HPLC showed that A13 was consumed completely (A13/(A14+A13)<1%). MTBE (25 L) was added to above mixture within 30 min and stirred for 30 min at −5° C. . . . The solid was collected by vacuum filtration. The cake was washed with MTBE (2×2.5 L). The wet cake was used for next step directly.

Step j

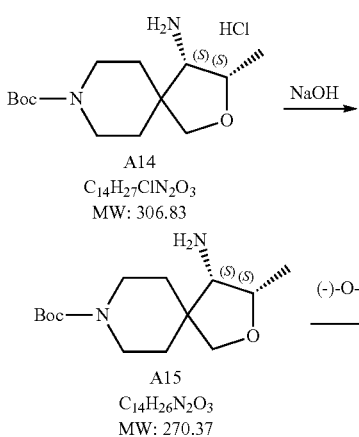

A14
C₁₄H₂₇ClN₂O₃
MW: 306.83

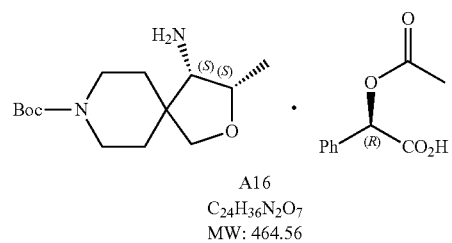

A15
C₁₄H₂₆N₂O₃
MW: 270.37

A16
C₂₄H₃₆N₂O₇
MW: 464.56

The wet solid A14 (from 9.2 kg A10) was stirred in MTBE (76 L) at 25° C., then the 16% NaOH (9.84 kg) solution was added dropwise to the MTBE suspension while maintaining IT<10° C. After addition, the mixture was stirred for 15 min and all solids were dissolved at 0° C. The organic phase was separated, and the aqueous phase was extracted with MTBE (2×20L). The combined organic phase was washed with brine (10 L) and evaporated under vacuum to remove all MTBE. ACN (24 L) was added to above residue, and the mixture was evaporated under vacuum to remove the organic solvents and yielded a crude A15 (5.42 kg, qnmr 90%, 18.04 mol, 1.0 eq). ACN (34.68 kg) was added to above residue and stirred for 10 min at 65° C. A solution of (-)—O-acetyl-D-mandelic acid (3.15 kg, 16.2 mol, 0.9 eq) in ACN (11.6 kg) was added drop-wise to the mixture (firstly added ⅓, stirred for 0.5 h, then added the others) over 3 h. The mixture was stirred for 1 h at 65° C., then cooled to 25° C. over 4 h and stirred for 12 h at 25° C. . . . The solid was collected by vacuum filtration, and the cake was washed with pre-cooled ACN (2×15 kg) (PSC-1) and dried under vacuum to give A16 (7.36 kg, yield 46% from A10 to A16).
¹H NMR (400 MHZ, DMSO-d6) δ=7.43-7.29 (m, 5H), 5.58 (s, 2H), 4.12-4.07 (m, 1H), 3.75-3.65 (m, 3H), 3.51-3.49 (m, 1H), 3.18-3.17 (m, 1H), 2.84 (bs, 2H), 2.05 (s, 3H), 1.60-1.40 (m, 13H), 1.14-1.12 (d, J=8.0 Hz, 3H).

Step k

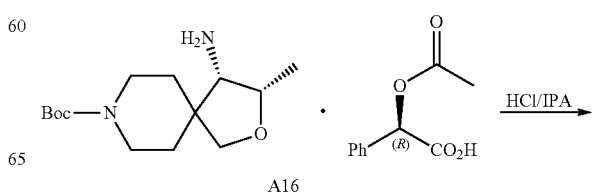

A16

-continued

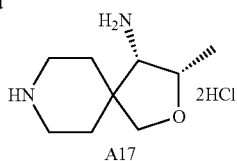

A17

To a solution of A16 (15 g) in MeOH (90 mL) was added dropwise 5N HCl/IPA (45 mL) at room temperature within 15 minutes. After the addition, the mixture was stirred for 6 hours. IPAC (180 mL) was added dropwise to above mixture within 1 h at room temperature. The resulting mixture was stirred for another 30 minutes before it was cooled to 0-5° C. The mixture was stirred at 0-5° C. for another 2 h and the precipitants were collected by filtration. The cake was washed with (45*2 mL) IPAC, dried under vacuum at 60° C. overnight to afford the product as a white solid. $^1$H NMR (400 MHz, DMSO-$d_6$) δ=9.37 (br s, 1H), 9.25 (br s, 1H), 8.42 (br s, 3H), 4.26-4.17 (m, 1H), 3.72 (ABq, J=9.1 Hz, 2H), 3.50-3.41 (m, 1H), 3.28-3.18 (m, 1H), 3.18-3.09 (m, 1H), 2.99-2.74 (m, 2H), 2.07-1.63 (m, 4H), 1.22 (d, J=6.5 Hz, 3H).

Step 1

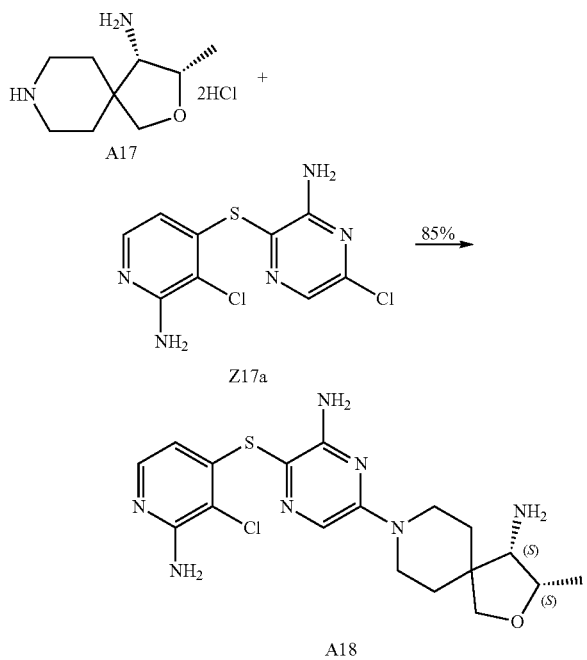

To a mixture of A17 (10 g) and Z17a (9.5 g) in DMAC (60 mL) was added $K_2CO_3$ (22.5 g) and $H_2O$ (40 mL) at room temperature. The mixture was degassed with nitrogen and stirred at 90° C. overnight. The mixture was cooled to room temperature, diluted with Me-THF (500 mL) and $H_2O$ (280 mL). The organic phase was separated and the aqueous phase was extracted with Me-THF (300 mL*2). The combined organic phases were washed with brine (200 mL*3), concentrated under vacuum to remove most of the solvent. The residue was diluted with IPA (60 mL) and $H_2O$ (20 mL), stirred at 50° C. for 1 h, cooled to 5° C. within 3 h, stirred at this temperature for 1 h. The solid was collected by vacuum filtration, dried under vacuum to afford the product as a yellow solid (12 g, 87.4%). $^1$H NMR (400 MHZ, DMSO-$d_6$) δ=7.64 (d, J=6.2 Hz, 1H), 7.62 (s, 1H), 6.26 (s, 2H), 6.13 (s, 2H), 5.74 (d, J=5.3 Hz, 1H), 4.12-4.02 (m, 1H), 3.90-3.78 (m, 2H), 3.67 (d, J=8.4 Hz, 1H), 3.49 (d, J=8.4 Hz, 1H), 3.33 (s, 2H), 2.91 (d, J=5.1 Hz, 1H), 1.78-1.68 (m, 1H), 1.67-1.57 (m, 1H), 1.56-1.41 (m, 2H), 1.08 (d, J=6.5 Hz, 3H).

Example 2

Formation of the Succinate Salt of the Compound of the Formula I

The reaction is summarized by the following Reaction Scheme:

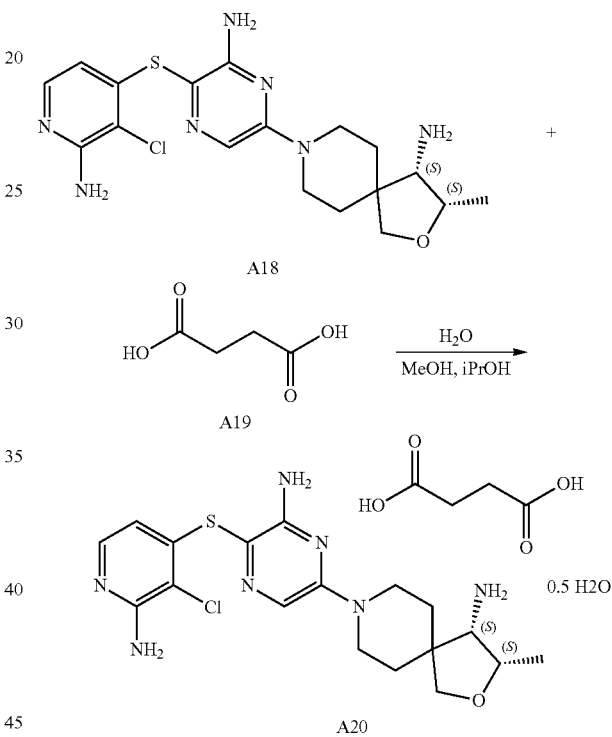

To a mixture of A18 (10 g) in MeOH (76 g) and $H_2O$ (24 g) was added succinic acid (2.94 g) at room temperature. The mixture was heated to 50° C., and stirred for 30 minutes to dissolve all solid. The solution was added to IPA (190 mL) at 60-65° C. The resulting mixture was stirred at 60° C. >5 hours, cooled to −15° C. within 5 hours and stirred at this temperature >4 hours. The solid was collected by vacuum filtration, dried under vacuum to afford the product as an off-white solid (10.8 g, 82.8%). $^1$H NMR (400 MHZ, DMSO-$d_6$) δ=7.64 (d, J=6.2 Hz, 1H), 7.63 (s, 1H), 6.26 (s, 2H), 6.16 (s, 2H), 5.74 (d, J=5.3 Hz, 1H), 4.12-4.02 (m, 1H), 3.90-3.78 (m, 2H), 3.67 (d, J=8.4 Hz, 1H), 3.49 (d, J=8.4 Hz, 1H), 3.33 (s, 2H), 2.91 (d, J=5.1 Hz, 1H), 2.34 (s, 4H), 1.71-1.60 (m, 4H), 1.13 (d, J=6.5 Hz, 3H).

In a special variant, the reaction follows the following Reaction Scheme, also including an optional milling to yield the final product;

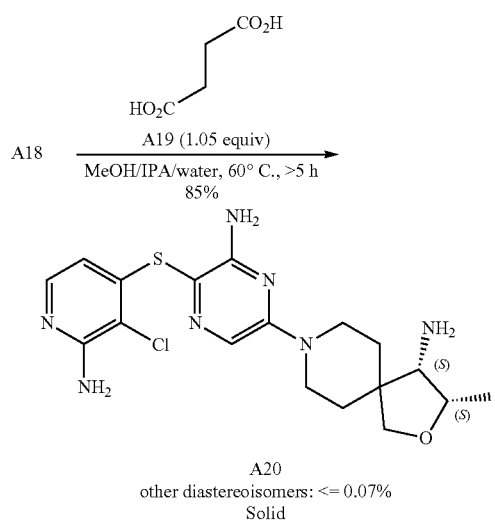
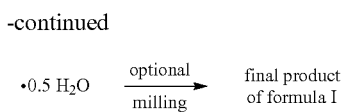
Example 3
Formation of the intermediate Z17a (3-((2-amino-3-chloropyridin-4-yl)thio)-6-chloropyrazin-2-amine), Variant 1
The compound Z17a was obtained by reaction according to the following Reaction Scheme:
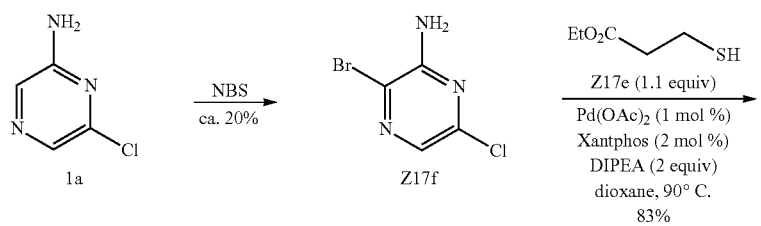
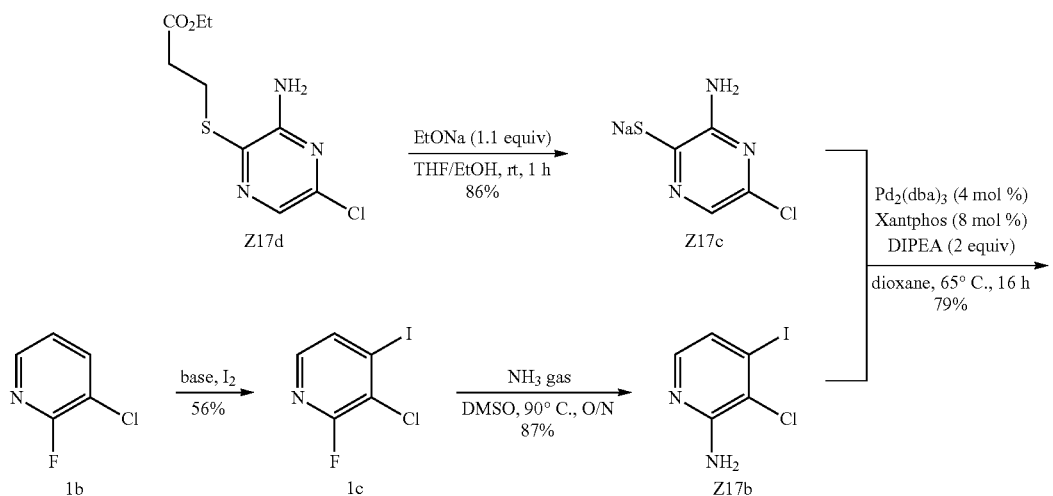
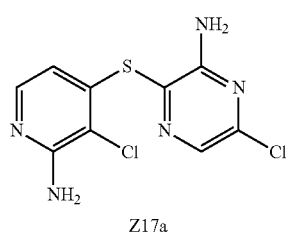

In detail, the synthesis of Compound Z17a was carried out as follows:

Step a

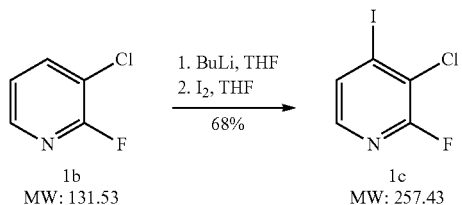 [SMILES: Fc1ncccc1Cl ; Fc1nccc(I)c1Cl]

Under nitrogen atmosphere, n-BuLi (2.5M, 7.6 L) was added dropwise to a solution of 3-chloro-2-fluoropyridine (2 kg) in THF (15 L) at −78° C. Then the resultant mixture was stirred for 1 h. Then a solution of I$_2$ (4.82 kg) in THF (6 L) was added dropwise. After addition, the reaction mixture was stirred for 30 min, and then quenched with sat. Na$_2$SO$_3$ (10 L), and warmed to 20-25° C. Phase was separated. The aqueous phase was extracted with EA (2×10 L). The combined organic phase was washed with sat. Na$_2$SO$_3$ (2×8 L), brine (8 L), and dried over Na$_2$SO$_4$. The organic phase was concentrated under vacuum. The residue was slurried in MeOH (4 L), filtered, and dried to offer 3-chloro-2-fluoro-4-iodopyridine 1c (2.2 kg, yield 68%).

Step c

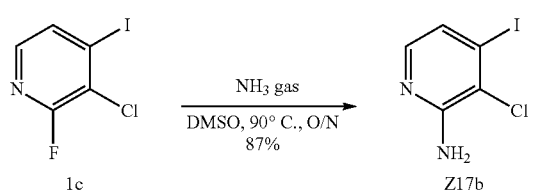 [SMILES: Fc1nccc(I)c1Cl ; Nc1nccc(I)c1Cl]

Into a solution of Compound 1c (8 kg) in DMSO (48 L) was passed through NH$_3$ (gas) at 80° C. overnight. TLC showed the reaction was finished. The reaction mixture was cooled to RT. The reaction mixture was added to water (140 L). The solid was collected and washed with water (25 L), dried to afford Z17b (6.91 kg, yield 87%). $^1$H NMR (400 MHZ, CDCl3) δ=7.61 (d, J=6.8 Hz, 1H), 7.14 (s, J=6.8 Hz, 1H), 5.09 (bs, 2H).

Step c

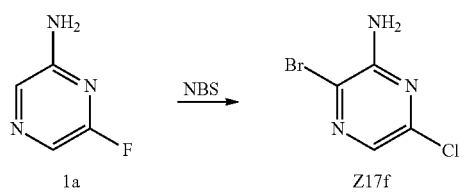 [SMILES: Nc1cncc(F)n1 ; "NBS" ; Nc1nc(Cl)cnc1Br]

A solution of 2-amino-6-chloro-pyrazine 1a (1 kg, 7.69 mol) in DCM (15 L) was heated to reflux, to which was charged NBS (417 g) in portions during 1 h. The reaction was cooled to room temperature. The reaction mixture was washed with water (3 L) and brine (3 L). The organic phase was evaporated, and the residue was purified by column chromatography to give product Z17f (3-bromo-6-chloro-pyrazin-2-amine) (180 g, 11% yield).

Step d

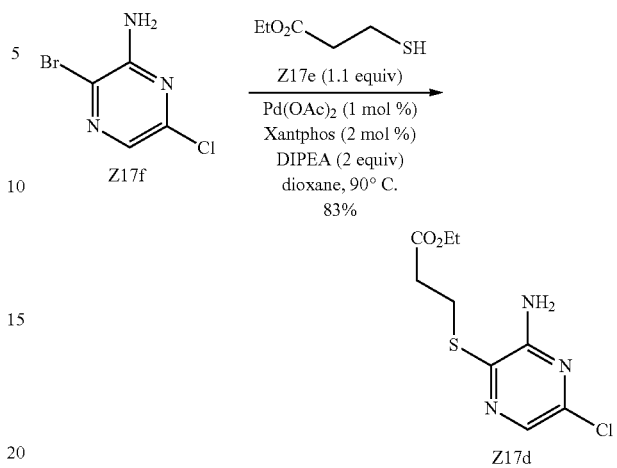

To a solution of 3-bromo-6-chloropyrazin-2-amine Z17f (6.0 kg, 28.78 mol) in 1,4-Dioxane (40 L) was added Pd(OAc)$_2$ (64.56 g, 287.6 mmol), Xantphos (333 g, 575.6 mmol), and DIPEA (7.44 kg, 57.56 mol) at room temperature under nitrogen. After another 30 minutes purging with nitrogen, methyl 3-mercaptopropanoate (3.81 kg, 31.70 mol) was added, resulting in darkening of the orange mixture. The mixture was heated to 90° C. HPLC showed complete conversion of the starting material. The mixture was allowed to cool to about room temperature, then diluted with EtOAc (40L). After aging for 30 min with stirring, the entire mixture was filtered and solids were washed with EtOAc (3×15L). The combined orange filtrate was concentrated to dryness and the solid residue was suspended in DCM (45 L). The mixture was heated to 35-40° C., and stirred for 1 h until all solids were dissolved. Then n-heptane (45L) was added dropwise. Upon complete addition, the mixture was cooled to 15-20° C. with stirring for 1 h. The solids were collected by vacuum filtration and solids were washed with cold 1:1 DCM/heptane (25 L), then heptane (25 L) (PSC-2). The solids were dried over the weekend to give Z17d (5.32 kg, yield 75%). $^1$H NMR (400 MHZ, CDCl3) δ=7.83 (s, 1H), 4.88 (bs, 2H), 3.73 (s, 3H), 3.47 (t, J=9.2 Hz, 2H), 2.79 (t, J=9.2 Hz, 2H).

Step e

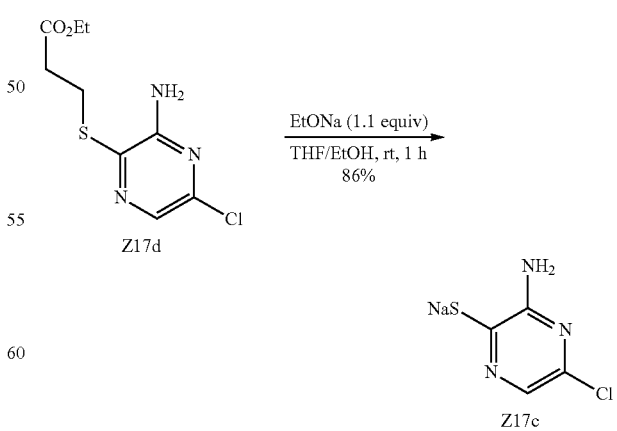

To a solution of Z17d (8.0 kg, assay 95%, 30.68 mol) in THF (70 L) was added EtONa (prepared from 776 g Na and 13.6 L EtOH) at room temperature and the mixture was stirred at ambient temperature for 1 hour. The mixture was then concentrated to a wet yellow solid by rotary evaporation and the residue was suspended in DCM (40L). The mixture stirred under N₂ for 16 h. The solids were collected by vacuum filtration and the cake was washed with DCM (about 15 L) until the filtrate was colorless (PSC-2). The solids were then dried under vacuum to give Z17c (6.93 kg, qNMR 72%, yield 88%). ¹H NMR (400 MHZ, D2O) δ=7.37 (s, 1H).

Step f

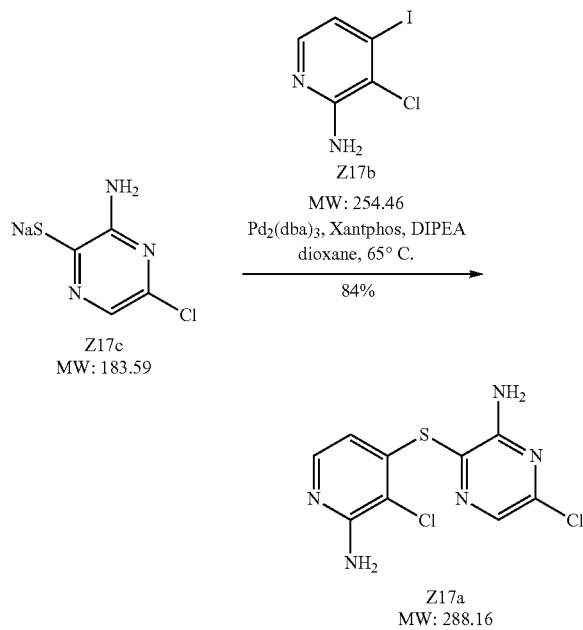

To a mixture of Z17c (6.95 kg, assay 72%, 27.23 mol) in 1,4-dioxane (72 L) was added Xantphos (233 g, 411 mmol, 0.015 eq), Pd$_2$(dba)$_3$ (186 g, 206 mmol, 0.0075 eq), Z17b (7.13 kg, 28.02 mol) and DIPEA (7.02 kg, 54.46 mol). The system was vacuated and purged with nitrogen gas three times. The mixture was stirred at 65° C. for 16 h under N$_2$. The mixture was cooled to RT and water (50 L) was added, filtered. The cake was washed with EA (25 L). The filtrate was extracted with EA (4×20 L). The organic phase was concentrated in vacuum to offer the crude product which was combined with the cake. Then DCM (60 L) was added to the crude product and stirred at 25-30° C. for 18 h and then filtered. The filter cake was slurried with CH$_2$Cl$_2$ (30 L) for 4 hrs and filtered. The filter cake was slurred in CH$_2$Cl$_2$ (30 L) for 16 hrs and filtered. Then the filter cake was dried in vacuum to give Z17a (3-((2-amino-3-chloropyridin-4-yl)thio)-6-chloropyrazin-2-amine; 9.1 kg, 84%) as light yellow solid. ¹H NMR (400 MHZ, DMSO-d$_6$) δ=7.89 (s, 1H), 7.7 (d, J=7.6 Hz, 1H), 7.18 (bs, 2H), 6.40 (bs, 2H), 5.97 (d, J=7.6 Hz, 1H).

Example 4

Alternative Formation of the Intermediate Z17a (Here Also Named Y7a)

By way of alternative and according to a preferred reaction method, the compound of the formula Z17a was obtained according to the following Reaction Scheme:

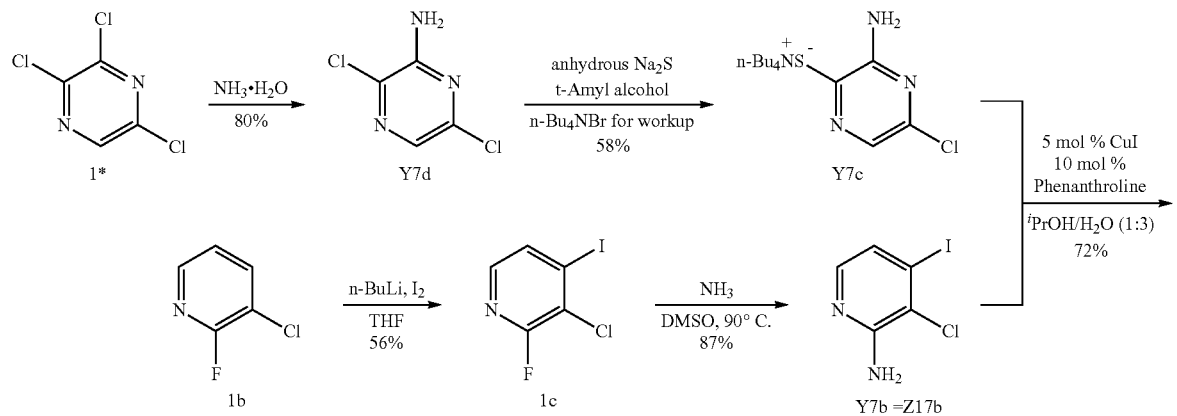

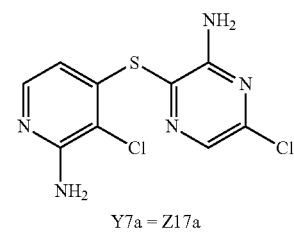

In detail, the synthesis of the compound of the formula Y7a=Z17a was carried out as follows:

Step a

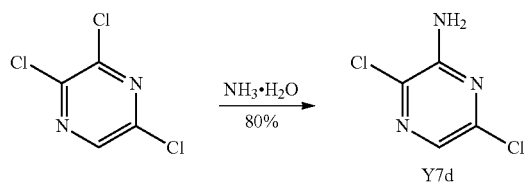

2,3,5-trichloropyrazine (70.50 g, 384.36 mmol, 1 equiv) and ammonia solution (25% wt, 364.00 g, 400 mL, 2.68 mol, 6.14 equiv) were added to a 1-L sealed reactor. The mixture was heated to 80° C., and stirred for 24 h, and the reaction was completed. The reaction mixture was cooled to 30° C., and filtered to give a brown filter cake. The brown filter cake was dissolved in acetone (50 mL), and filtered. To the filtrate was added petroleum ether (300 mL). The suspension was stirred for 4 h, and filtered to give the crude product. The crude product was slurried in combined solvents of petroleum ether and acetone (10/1, 200 mL) and filtered to give the product Y7d (51.00 g, 307.91 mmol, 80% yield) as a light yellow solid. $^1$H NMR (400 MHZ, DMSO-$d_6$) δ=7.63 (s, 1H), Step b

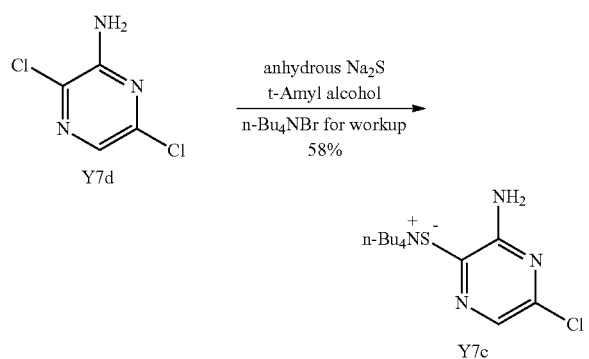

To a 200 mL round bottom flask was added Na$_2$S (10.816 g, 44 wt % containing crystalline water, 60.978 mmol) and toluene (100 mL). The mixture was heated to reflux, and water was removed with a Dean-Stark trap (about 5~6 mL water was distilled out). After cooling, the mixture was concentrated to dryness.

To above round bottom flask was added Y7d (5.000 g, 30.489 mmol) and 2-methylbutan-2-ol (50 mL), the reaction was heated to reflux and stirred for 36 h. After cooling to 25° C., the mixture was filtered. The solvent of the filtrate was exchanged with n-heptane (5 V, 3 times, based on Y7d), and finally concentrated to 1V residue. THF (25 mL) was charged to the residue at 25° C., and stirred. The suspension was filtered and washed with THF/n-heptane (5 mL/5 mL) to give a brown solid (6.200 g).

To another 200 mL round bottom flask was added above brown solid (6.200 g), 10% brine (25 mL), Me-THF (30 mL) and n-Bu4NBr (9.829 g, 30.489 mmol). The mixture was stirred for 0.5 h at room temperature, and the phases were separated. The organic phase was washed with 20% brine (25 mL), and exchanged the solvent with iso-propanol (5 V*3 times, based on Y7d) to give the iso-propanol solution of Y7c (27.000 g, 99.2% purity by HPLC area, 58.08% assay yield). $^1$H NMR (400 MHz, DMSO-$d_6$) δ=6.88 (s, 1H), 2.97-2.92 (m, 14H), 1.38-1.31 (m, 14H), 1.13-1.04 (m, 14H), 0.73-0.69 (t, 21H).

Step c

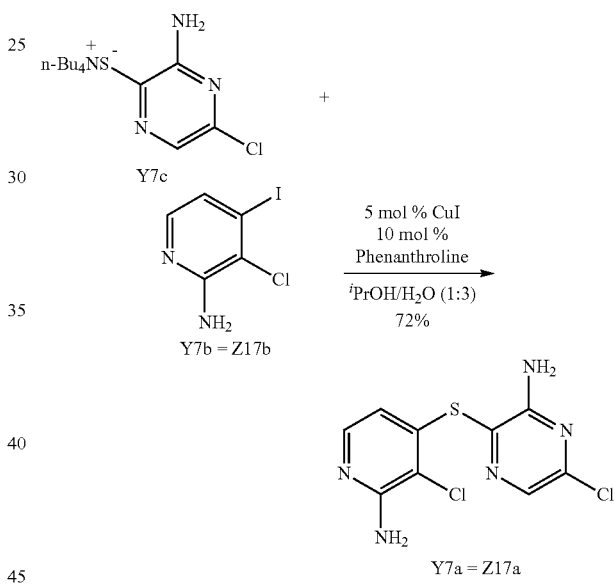

To a 25-mL round-bottom flask was added Y7c (4.7 g, 23.27 wt %, IPA solution from Step b, 2.723 mmol, 1.0 equiv), Y7b (1.052 g, 4.085 mmol, 1.5 equiv), 1,10-Phenanthroline (0.05 g, 0.272 mmol) and water (8 mL). The mixture was purged with nitrogen gas three times, and CuI (0.026 g, 0.136 mmol) was added under nitrogen atmosphere. The mixture was heated up to 65° C., and stirred for 3 h, and the reaction was completed. The reaction was cooled to room temperature and filtered, and the filter cake was washed with water (4 mL*3). The filter cake was slurried in MTBE (6 mL) for 30 min and filtered. The filter cake was washed with MTBE (6 mL) and dried to afford Y7a which is Z17a (565 mg, 72% yield).

Z17b is synthesized as described in Example 3 Step a and Step b.

Example 5

Alternative Synthesis of the Intermediate Z17a

According to another preferred method, the compound of the formula Z17a was obtained in accordance with the following Reaction Scheme:

Step a

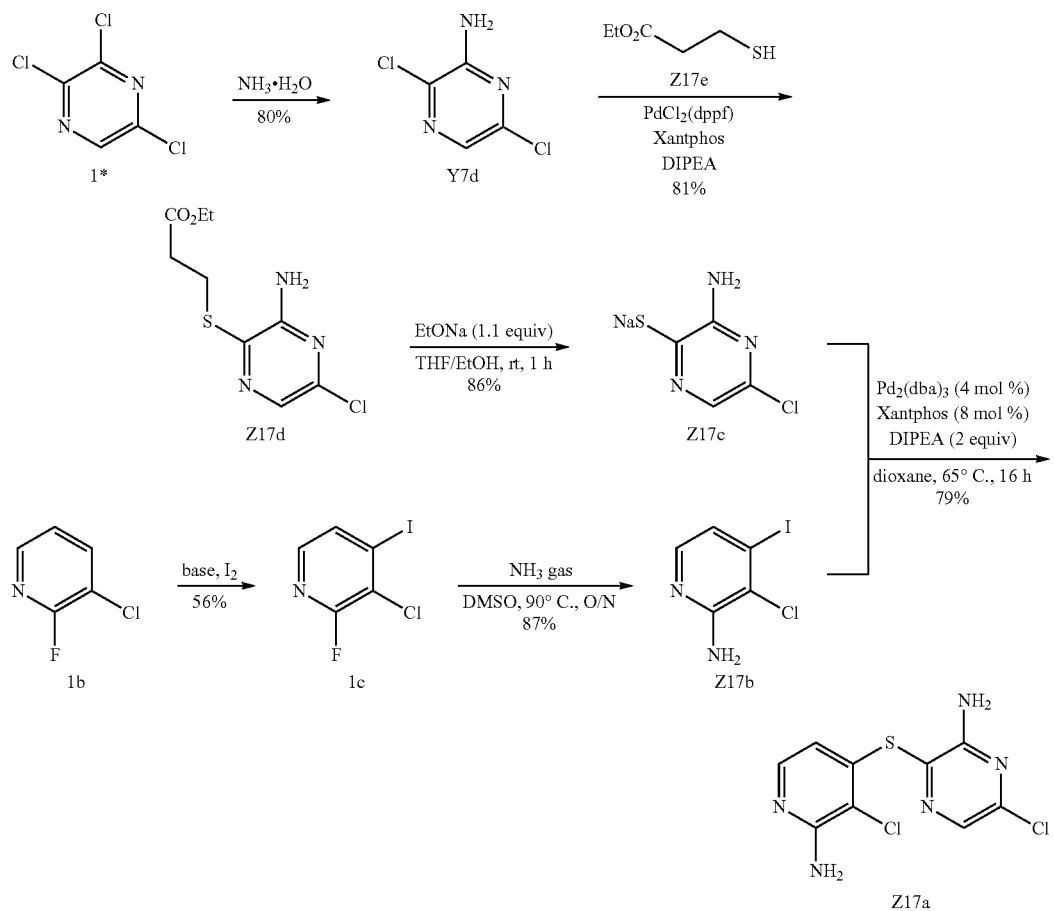

The reactions were carried out as follows;
Y7d was synthesised as described in Example 4 step a.
Step b To a three-necked round-bottle flask was added Y7d (200 mg, 1.22 mmol, 1 equiv), dioxane (4 mL). The solution was vacuated and purged with nitrogen gas three times. Xantphos (14 mg, 0.024 mmol, 0.02 equiv), PdCl$_2$ (dppf) (8.9 mg, 0.012 mmol, 0.1 equiv), and DIPEA (0.32 g, 2.44 mmol, 2.0 equiv) were added under nitrogen atmosphere. The solution was heated to 85° C. for overnight. The reaction was cooled and evaporated. The residue was purified by column chromatography (eluent/ethyl acetate/heptane=1/1) to give Z17d (259 mg, 0.99 mmol, 81%). $^1$H NMR (400 MHZ, CDCl$_3$) δ=7.83 (s, 1H), 4.88 (bs, 2H), 3.73 (s, 3H), 3.47 (t, J=9.2 Hz, 2H), 2.79 (t, J=9.2 Hz, 2H).

The remaining steps were carried out as described in Example 4, Steps e and f, to yield Z17a. Z17b was synthesized as described in Example 3 Step a and Step b.

Example 6

(3S,4S)-8-(6-amino-5-((2-amino-3-chloropyridin-4-yl)thio)pyrazin-2-yl)-3-methyl-2-oxa-8-azaspiro[4.5]decan-4-amine, succinate (1:1) hemihydrate, modification (form) H$_4$: Variant a)

50 ml ethanol and 2.5 ml water were added to a 100 ml flask containing 3.0 g of free base of 3S,4S)-8-(6-amino-5-((2-amino-3-chloropyridin-4-yl)thio)pyrazin-2-yl)-3-methyl-2-oxa-8-azaspiro[4.5]decan-4-amine (obtained as A18 for example as described in Example 1) and 848.0 mg of succinic acid. The mixture was heated to 50° C. to generate a clear solution. The temperature was lowered to 15° C. during a period of 3 hours. The solution was kept stirring at 15° C. overnight. Precipitated solid was separated via suction filtration and 50 ml of acetone was added to produce a suspension. The suspension was stirred at 50° C. for 3 hours. The solid was separated with suction filtration and dried at room temperature under vacuum for 3 hours. Yield was about 60%.

The succinate appeared as a highly crystalline solid, with a melting point onset of 94.4° C., and an accompanying enthalpy of 96 J/g. The succinate salt crystals showed aggregates of broken drusy tabular particles.
Variant b)

14.34 g of 3S,4S)-8-(6-amino-5-((2-amino-3-chloropyridin-4-yl)thio)pyrazin-2-yl)-3-methyl-2-oxa-8-azaspiro[4.5]decan-4-amine free form (obtained as A18 for example as described in Example 1) and 4.053 g of succinic acid were equilibrated in 100 mL 95% EtOH at 50° C. Add 5 mL of water into the system and heat to 70-75° C. Add 95 mL of pure EtOH and heat for 30 min more. Stir over night at 25° C. Filter the mixture wash with EtOH and dry under vacuum in an oven at room temperature. Yield is 87.5%.

The title succinate (1:1) hydrate salt Modification $H_A$ obtained according to any one of variants a) and b) is highly crystalline. It holds constant water content over 10% RH to 50% RH at room temperature. The succinate salt modification $H_A$ shows high solubility in aqueous media indicating the potentially good bioavailability.

The following XRPD data were obtained (table of 2-theta values) (both variants):

| Angle (2-theta) in deg. | d-value in Å | Rel. intensity in % |
|---|---|---|
| 4.4 | 19.97 | 9.6% |
| 8.1 | 10.85 | 24.9% |
| 16.3 | 5.42 | 57.5% |
| 17.5 | 5.07 | 100.0% |
| 20.9 | 4.24 | 11.1% |
| 22.5 | 3.95 | 41.7% |
| 23.0 | 3.86 | 25.5% |
| 23.7 | 3.76 | 18.3% |
| 24.6 | 3.61 | 23.9% |
| 26.8 | 3.32 | 21.3% |
| 27.9 | 3.20 | 14.8% |
| 36.3 | 2.47 | 15.3% |

$^1$H NMR (400 MHZ, DMSO-$d_6$) δ 6.16 (s, 2H), 7.63 (d, J=5.8 Hz, 2H), 6.27 (s, 2H), 5.86-5.60 (m, 1H), 4.25-4.05 (m, 1H), 4.05-3.82 (m, 2H), 3.75 (d, J=8.7 Hz, 1H), 3.56 (d, J=8.7 Hz, 1H), 3.24 (dddd, J=23.7, 13.4, 9.9, 3.3 Hz, 2H), 3.09 (d, J=5.0 Hz, 1H), 2.34 (s, 4H), 1.77-1.38 (m, 4H), 1.13 (d, J=6.4 Hz, 3H).

| Name | Shift | Range | H's | Integral | Class | J's |
|---|---|---|---|---|---|---|
| 1 A (d) | 1.13 | 1.17 . . . 1.08 | 3 | 3.00 | d | 6.44 |
| 2 B (m) | 5.74 | 5.86 . . . 5.60 | 1 | 1.01 | m | |
| 3 C (d) | 7.63 | 7.72 . . . 7.48 | 2 | 2.20 | d | 5.77 |
| 4 E (m) | 1.64 | 1.77 . . . 1.38 | 4 | 4.19 | m | |
| 5 F (s) | 6.16 | 6.21 . . . 6.01 | 2 | 2.04 | s | |
| 6 G (s) | 6.27 | 6.40 . . . 6.19 | 2 | 2.04 | s | |
| 7 H (m) | 4.11 | 4.25 . . . 4.05 | 1 | 1.02 | m | |
| 8 I (m) | 3.96 | 4.05 . . . 3.82 | 2 | 2.11 | m | |
| 9 J (d) | 3.75 | 3.86 . . . 3.65 | 1 | 1.22 | d | 8.67 |
| 10 K (d) | 3.56 | 3.63 . . . 3.48 | 1 | 1.17 | d | 8.67 |
| 11 L (d) | 3.09 | 3.15 . . . 3.00 | 1 | 1.12 | d | 5.01 |
| 12 M (dddd) | 3.24 | 3.36 . . . 3.13 | 2 | 2.07 | dddd | 3.31, 9.89, 13.36, 23.70 |
| 13 N (s) | 2.34 | 2.39 . . . 2.24 | 4 | 4.32 | s | |

FIG. 1 shows an XRPD diagram obtained. Molar Stochiometry by NMR; 1:1.08 (Base: Succinic Acid). At 50° C./75% RH, the succinate salt showed acceptable degradation levels in all four experimental excipient mixtures.

Example 7

(3S,4S)-8-(6-amino-5-((2-amino-3-chloropyridin-4-yl)thio)pyrazin-2-yl)-3-methyl-2-oxa-8-azaspiro[4.5]decan-4-amine hydrochloride 50 mg of (3S,4S)-8-(6-amino-5-((2-amino-3-chloropyridin-4-yl)thio)pyrazin-2-yl)-3-methyl-2-oxa-8-azaspiro[4.5]decan-4-amine free form and 23.35 mg of hydrochloric acid were equilibrated in 1 mL ACN at 50° C. for 4 hours. Cool down to room temperature overnight and filter the mixture. This yields the hydrochoride salt.

Data suggested that solvate formation was likely. The following XRPD data were obtained (table of 2-theta values):

| Angle (2-theta) in deg. | d-value in Å | Rel. intensity in % |
|---|---|---|
| 15.3 | 5.80 | 18.9% |
| 16.1 | 5.50 | 75.4% |
| 18.9 | 4.69 | 20.3% |
| 20.9 | 4.25 | 38.0% |
| 21.5 | 4.13 | 100.0% |
| 22.2 | 4.01 | 34.3% |
| 24.0 | 3.70 | 37.3% |
| 27.1 | 3.29 | 33.0% |
| 29.9 | 2.98 | 19.6% |
| 31.0 | 2.89 | 23.9% |
| 15.3 | 5.80 | 18.9% |
| 16.1 | 5.50 | 75.4% |

$^1$H NMR (500 MHz, DMSO-$d_6$) δ 7.70-7.57 (m, 2H), 6.26 (s, 2H), 6.17 (s, 2H), 5.74 (d, J=5.4 Hz, 1H), 4.35 (t, J=5.0 Hz, 1H), 4.28-4.13 (m, 2H), 4.11 (d, J=13.8 Hz, 1H), 3.90 (d, J=9.0 Hz, 1H), 3.67 (d, J=8.9 Hz, 1H), 3.43 (td, J=7.0, 4.9 Hz, 1H), 1.84-1.48 (m, 4H), 1.23 (d, J=6.6 Hz, 3H).

| Name | Shift | Range | H's | Integral | Class | J's |
|---|---|---|---|---|---|---|
| 1 A (d) | 1.23 | 1.31 . . . 1.15 | 3 | 3.00 | d | 6.56 |
| 2 B (m) | 7.64 | 7.70 . . . 7.57 | 2 | 2.01 | m | |
| 3 C (s) | 6.26 | 6.33 . . . 6.22 | 2 | 2.02 | s | |
| 4 D (s) | 6.17 | 6.22 . . . 6.08 | 2 | 1.99 | s | |
| 5 E (d) | 5.74 | 5.82 . . . 5.64 | 1 | 0.97 | d | 5.37 |

-continued

| Name | Shift | Range | H's | Integral | Class | J's |
|---|---|---|---|---|---|---|
| 6 F (t) | 4.35 | 4.45 ... 4.28 | 1 | 0.61 | t | 5.05, 5.05 |
| 7 G (m) | 4.20 | 4.28 ... 4.13 | 2 | 2.18 | m | |
| 8 H (d) | 4.11 | 4.16 ... 4.04 | 1 | 1.08 | d | 13.78 |
| 9 I (d) | 3.90 | 3.94 ... 3.85 | 1 | 0.97 | d | 9.00 |
| 10 J (td) | 3.43 | 3.51 ... 3.38 | 1 | 1.09 | td | 4.87, 7.03, 7.05 |
| 11 K (d) | 3.67 | 3.76 ... 3.57 | 1 | 1.03 | d | 8.93 |
| 12 L (m) | 1.67 | 1.84 ... 1.48 | 4 | 4.08 | m | |

FIG. 2 shows an XRPD diagram obtained.

Example 8

(3S,4S)-8-(6-amino-5-((2-amino-3-chloropyridin-4-yl)thio)pyrazin-2-yl)-3-methyl-2-oxa-8-azaspiro[4.5]decan-4-amine mesylate 50 mg of 3S,4S)-8-(6-amino-5-((2-amino-3-chloropyridin-4-yl)thio)pyrazin-2-yl)-3-methyl-2-oxa-8-azaspiro[4.5]decan-4-amine free form and 11.62 mg of methylsulfonic acid were equilibrated in 1 mL THF at 50° C. Cool down to room temperature overnight and filter the mixture. This yields the mesylate salt.

Data suggested solvate formation was likely. The following XRPD data were obtained (table of 2-theta values):

| Angle (2-theta) in deg. | d-value in Å | Rel. intensity in % |
|---|---|---|
| 11.8 | 7.50 | 13.8% |
| 17.2 | 5.16 | 21.1% |
| 17.8 | 4.97 | 48.7% |
| 18.9 | 4.69 | 100.0% |
| 20.9 | 4.24 | 19.4% |
| 22.5 | 3.95 | 20.1% |
| 23.7 | 3.75 | 37.5% |
| 24.2 | 3.68 | 41.7% |

$^1$H NMR (500 MHZ, DMSO-$d_6$) & 7.88 (s, 3H), 7.74-7.61 (m, 2H), 6.31 (s, 2H), 5.96 (d, J=6.4 Hz, 1H), 4.34-4.06 (m, 4H), 3.88 (d, J=9.0 Hz, 2H), 3.47-3.31 (m, 3H), 2.31 (s, 6H), 1.85-1.40 (m, 4H), 1.22 (d, J=6.5 Hz, 3H),

| Name | Shift | Range | H's | Integral | Class | J's |
|---|---|---|---|---|---|---|
| 1 A (d) | 1.22 | 1.30 ... 1.14 | 3 | 3.00 | d | 6.54 |
| 2 B (s) | 2.31 | 2.35 ... 2.23 | 6 | 6.02 | s | |
| 3 C (m) | 7.70 | 7.74 ... 7.61 | 2 | 2.10 | m | |
| 4 D (d) | 5.96 | 6.05 ... 5.87 | 1 | 0.86 | d | 6.38 |
| 5 E (s) | 6.31 | 6.46 ... 6.21 | 2 | 1.65 | s | |
| 6 F (m) | 1.60 | 1.85 ... 1.40 | 4 | 4.06 | m | |
| 7 G (m) | 4.19 | 4.34 ... 4.06 | 4 | 3.57 | m | |
| 8 H (d) | 3.88 | 3.96 ... 3.82 | 2 | 2.25 | d | 8.97 |
| 9 I (m) | 3.44 | 3.47 ... 3.31 | 3 | 3.02 | m | |
| 10 J (s) | 7.88 | 8.02 ... 7.81 | 3 | 3.00 | s | |

FIG. 3 shows an XRPD diagram obtained.

Example 9

(3S,4S)-8-(6-amino-5-((2-amino-3-chloropyridin-4-yl)thio)pyrazin-2-yl)-3-methyl-2-oxa-8-azaspiro[4.5]decan-4-amine, fumarate 50 mg of (3S,4S)-8-(6-amino-5-((2-amino-3-chloropyridin-4-yl)thio)pyrazin-2-yl)-3-methyl-2-oxa-8-azaspiro[4.5]decan-4-amine free form and 13.89 mg of fumaric acid were equilibrated in 1 mL EtOH at 50° C. Cool down to room temperature overnight and filter the mixture. This yielded the fumarate salt.

The following XRPD data were obtained (table of 2-theta values):

| Angle (2-theta) in deg. | d-value in Å | Rel. intensity in % |
|---|---|---|
| 10.4 | 8.54 | 17.3% |
| 14.9 | 5.93 | 51.9% |
| 17.8 | 4.98 | 22.6% |
| 19.2 | 4.61 | 100.0% |
| 19.7 | 4.50 | 66.7% |
| 21.4 | 4.15 | 26.3% |
| 22.4 | 3.96 | 79.9% |
| 24.9 | 3.57 | 31.7% |
| 25.9 | 3.44 | 25.7% |
| 28.9 | 3.08 | 16.6% |
| 29.7 | 3.00 | 17.1% |
| 31.4 | 2.85 | 17.4% |

$^1$H NMR (500 MHZ, DMSO-$d_6$) δ 7.63 (d, J=6.4 Hz, 2H), 6.52 (s, 2H), 6.26 (s, 2H), 6.14 (s, 2H), 5.74 (d, J=5.3 Hz, 1H), 4.20-4.02 (m, 1H), 3.97 (dd, J=19.6, 14.4 Hz, 2H), 3.76 (d, J=8.6 Hz, 1H), 3.56 (d, J=8.7 Hz, 1H), 3.32-3.16 (m, 3H), 3.11 (d, J=5.1 Hz, 1H), 1.82-1.37 (m, 4H), 1.14 (d, J=6.5 Hz, 3H).

| Name | Shift | Range | H's | Integral | Class | J's |
|---|---|---|---|---|---|---|
| 1 A (d) | 1.14 | 1.25 ... 1.01 | 3 | 3.00 | d | 6.45 |
| 2 B (d) | 7.63 | 7.76 ... 7.49 | 2 | 2.01 | d | 6.41 |
| 3 C (s) | 6.52 | 6.61 ... 6.42 | 2 | 1.76 | s | |
| 4 D (s) | 6.26 | 6.33 ... 6.20 | 2 | 1.87 | s | |
| 5 E (s) | 6.14 | 6.18 ... 6.02 | 2 | 1.87 | s | |
| 6 F (d) | 5.74 | 5.80 ... 5.63 | 1 | 0.90 | d | 5.35 |
| 7 G (m) | 1.64 | 1.82 ... 1.37 | 4 | 4.15 | m | |
| 8 H (d) | 3.11 | 3.14 ... 3.03 | 1 | 1.18 | d | 5.11 |
| 9 I (m) | 4.12 | 4.20 ... 4.02 | 1 | 1.03 | m | |
| 10 J (dd) | 3.97 | 4.02 ... 3.85 | 2 | 1.91 | dd | 14.36, 19.64 |
| 11 K (d) | 3.76 | 3.84 ... 3.67 | 1 | 1.15 | d | 8.64 |
| 12 L (d) | 3.56 | 3.64 ... 3.49 | 1 | 1.50 | d | 8.69 |
| 13 M (m) | 3.22 | 3.32 ... 3.16 | 3 | 3.04 | m | |

FIG. 4 shows an XRPD diagram obtained.

Example 10

(3S,4S)-8-(6-amino-5-((2-amino-3-chloropyridin-4-yl)thio)pyrazin-2-yl)-3-methyl-2-oxa-8-azaspiro[4.5]decan-4-amine adipate (1:1), Modification A 30 ml acetonitrile were added to a 100 ml flask containing 3.0 g of (3S,4S)-8-(6-amino-5-((2-amino-3-chloropyridin-4-yl)thio)pyrazin-2-yl)-3-methyl-2-oxa-8-azaspiro[4.5]decan-4-amine and 1.0 g of adipic acid. The resulting suspension was heated to 50° C. for 3 hours and then cooled to 15° C. during a period of 3 hours. The suspension was kept stirring at 15° C. overnight. The solid was separated with suction filtration and dried at 40° C. under vacuum for 12 hours. Yield of the resulting adipate salt Modification A was about 80%.

The adipate appeared as a highly crystalline solid, with a melting point onset of 145.3° C., and an accompanying enthalpy of 90 J/g. The adipate salt crystals showed aggregates of tabular particles.

Molar Stochiometry by NMR; 1:1.02 (base: adipic acid). The following XRPD data were obtained (table of 2-theta values):

| Angle (2-theta) in deg. | d-value in Å | Rel. intensity in % |
|---|---|---|
| 3.7 | 23.58 | 93.9% |
| 9.2 | 9.58 | 34.1% |
| 10.2 | 8.71 | 40.3% |
| 15.7 | 5.64 | 21.4% |
| 17.0 | 5.20 | 100.0% |
| 17.4 | 5.11 | 68.0% |
| 18.3 | 4.85 | 73.0% |
| 21.9 | 4.06 | 21.1% |
| 23.2 | 3.83 | 35.6% |
| 25.2 | 3.53 | 30.4% |
| 26.2 | 3.40 | 43.5% |
| 27.2 | 3.27 | 19.4% |

$^1$H NMR (400 MHZ, DMSO-$d_6$) δ 7.63 (d, J=5.3 Hz, 2H), 6.27 (s, 3H), 6.14 (s, 2H), 5.74 (d, J=5.3 Hz, 1H), 4.19-4.00 (m, 1H), 3.98-3.77 (m, 2H), 3.68 (d, J=8.5 Hz, 1H), 3.49 (d, J=8.5 Hz, 1H), 3.33 (dddd, J=31.4, 13.1, 9.3, 3.4 Hz, 2H), 2.93 (d, J=5.1 Hz, 1H), 2.28-2.09 (m, 4H), 1.80-1.56 (m, 2H), 1.57-1.37 (m, 6H), 1.09 (d, J=6.4 Hz, 3H).

| | Name | Shift | Range | H's | Integral | Class | J's |
|---|---|---|---|---|---|---|---|
| 1 | A (d) | 1.09 | 1.17 ... 0.99 | 3 | 3.00 | d | 6.40 |
| 2 | B (d) | 7.63 | 7.81 ... 7.46 | 2 | 2.02 | d | 5.31 |
| 3 | C (s) | 6.27 | 6.41 ... 6.23 | 3 | 2.50 | s | |
| 4 | D (s) | 6.14 | 6.18 ... 6.05 | 2 | 1.93 | s | |
| 5 | E (d) | 5.74 | 5.80 ... 5.62 | 1 | 1.16 | d | 5.31 |
| 6 | F (m) | 4.08 | 4.19 ... 4.00 | 1 | 1.02 | m | |
| 7 | G (m) | 3.86 | 3.98 ... 3.77 | 2 | 1.93 | m | |
| 8 | H (d) | 3.68 | 3.77 ... 3.62 | 1 | 0.95 | d | 8.48 |
| 9 | I (d) | 3.49 | 3.58 ... 3.42 | 1 | 0.96 | d | 8.50 |
| 10 | J (d) | 2.93 | 3.01 ... 2.82 | 1 | 0.84 | d | 5.13 |
| 11 | K (dddd) | 3.33 | 3.42 ... 3.13 | 2 | 1.74 | dddd | 3.38, 9.28, 13.09, 31.38 |
| 12 | L (m) | 2.19 | 2.28 ... 2.09 | 4 | 3.91 | m | |
| 13 | M (m) | 1.66 | 1.80 ... 1.56 | 2 | 1.77 | m | |
| 14 | N (m) | 1.49 | 1.57 ... 1.37 | 6 | 6.06 | m | |

FIG. 5 shows an XRPD diagram obtained. The Adipate showed strong degradation with a mixture of pharmaceutical ingredients containing mannitol, Ac-di-Sol and microcrystalline cellulose.

Example 11

(3S,4S)-8-(6-amino-5-((2-amino-3-chloropyridin-4-yl)thio)pyrazin-2-yl)-3-methyl-2-oxa-8-azaspiro[4.5]decan-4-amine, succinate (1:1), anhydrous form, Modification A 2.0 g (3S,4S)-8-(6-amino-5-((2-amino-3-chloropyridin-4-yl)thio)pyrazin-2-yl)-3-methyl-2-oxa-8-azaspiro[4.5]decan-4-amine free form and 1.13 g succinic acid were added into an EasyMax reactor, followed by addition of 40 mL of ethanol. Obtained mixture was stirred at 25° C. for three days. The mixture was filtered. The solid phase was washed with 40 mL of ethanol and dried at ambient environment. This yielded mono-succinate, anhydrous form, Modification A.

The following XRPD data were obtained (table of 2-theta values):

| Angle (2-theta) in deg. | d-value in Å | Rel. intensity in % |
|---|---|---|
| 10.3 | 8.61 | 15.6% |
| 14.8 | 5.97 | 48.4% |
| 17.8 | 4.99 | 26.5% |
| 19.2 | 4.63 | 100.0% |
| 19.7 | 4.51 | 63.8% |
| 21.3 | 4.16 | 31.5% |
| 22.3 | 3.98 | 74.0% |
| 24.8 | 3.59 | 35.0% |
| 25.8 | 3.45 | 33.8% |
| 28.8 | 3.09 | 18.7% |

-continued

| Angle (2-theta) in deg. | d-value in Å | Rel. intensity in % |
|---|---|---|
| 29.6 | 3.01 | 24.0% |
| 31.3 | 2.86 | 18.0% |

$^1$H NMR (400 MHZ, DMSO-$d_6$) δ 7.73-7.53 (m, 2H), 6.27 (s, 2H), 6.16 (s, 2H), 5.73 (d, J=5.4 Hz, 1H), 4.26-4.03 (m, 1H), 4.04-3.87 (m, 2H), 3.75 (d, J=8.7 Hz, 1H), 3.56 (d, J=8.7 Hz, 1H), 3.23 (dddd, J=23.6, 13.3, 9.9, 3.3 Hz, 2H), 3.10 (d, J=5.0 Hz, 1H), 2.35 (s, 5H), 1.72-1.40 (m, 4H), 1.13 (d, J=6.4 Hz, 3H).

| | Name | Shift | Range | H's | Integral | Class | J's |
|---|---|---|---|---|---|---|---|
| 1 | A (d) | 1.13 | 1.17 ... 1.09 | 3 | 3.00 | d | 6.43 |
| 2 | B (s) | 6.16 | 6.23 ... 6.08 | 2 | 2.09 | s | |
| 3 | C (s) | 6.27 | 6.39 ... 6.22 | 2 | 1.99 | s | |
| 4 | D (m) | 7.64 | 7.73 ... 7.53 | 2 | 2.21 | m | |
| 5 | E (m) | 1.63 | 1.72 ... 1.40 | 4 | 3.98 | m | |
| 6 | F (s) | 2.35 | 2.42 ... 2.23 | 5 | 4.56 | s | |
| 7 | G (d) | 3.10 | 3.13 ... 3.02 | 1 | 1.07 | d | 5.01 |
| 8 | H (dddd) | 3.23 | 3.31 ... 3.11 | 2 | 2.13 | dddd | 3.29, 9.88, 13.30, 23.62 |
| 9 | I (d) | 3.56 | 3.64 ... 3.52 | 1 | 1.10 | d | 8.68 |
| 10 | J (d) | 3.75 | 3.80 ... 3.68 | 1 | 1.10 | d | 8.69 |
| 11 | K (m) | 3.96 | 4.04 ... 3.87 | 2 | 2.08 | m | |

| Name | Shift | Range | H's | Integral | Class | J's |
|---|---|---|---|---|---|---|
| 12 L (m) | 4.11 | 4.26 ... 4.03 | 1 | 1.08 | m | |
| 13 M (d) | 5.73 | 5.85 ... 5.65 | 1 | 1.04 | d | 5.36 |

FIG. 6 shows an XRPD diagram obtained.

Example 12

(3S,4S)-8-(6-amino-5-((2-amino-3-chloropyridin-4-yl)thio)pyrazin-2-yl)-3-methyl-2-oxa-8-azaspiro[4.5]decan-4-amine, succinate (2:1), hydrate, Modification $H_A$ 2 g of (3S,4S)-8-(6-amino-5-((2-amino-3-chloropyridin-4-yl)thio)pyrazin-2-yl)-3-methyl-2-oxa-8-azaspiro[4.5]decan-4-amine monosuccinate, hydrate, Modification $H_A$ was added into an appropriate flask. 20 mL of a mixture of acetonitrile/water (80:20, volume/volume) was added in to the flask and the obtained suspension was stirred overnight. The mixture was filtered and dried to solid phase at ambient environment. This yielded hemisuccinate, hydrate, Modification $H_A$.

The following XRPD data were obtained (table of 2-theta values):

| Angle (2-theta) in deg. | d-value in Å | Rel. intensity in % |
|---|---|---|
| 11.5 | 7.67 | 55.6% |
| 12.1 | 7.33 | 19.9% |
| 15.8 | 5.60 | 14.5% |
| 18.2 | 4.88 | 14.5% |
| 19.1 | 4.64 | 100.0% |
| 21.5 | 4.14 | 14.5% |
| 22.0 | 4.04 | 35.1% |
| 23.7 | 3.76 | 52.5% |
| 24.9 | 3.57 | 36.9% |
| 28.4 | 3.14 | 25.3% |
| 28.7 | 3.11 | 21.6% |

$^1$H NMR (400 MHZ, DMSO-$d_6$) δ 7.73-7.50 (m, 2H), 6.26 (s, 2H), 6.14 (s, 2H), 5.74 (d, J=5.4 Hz, 1H), 4.17-4.02 (m, 1H), 3.91 (t, J=13.0 Hz, 2H), 3.72 (d, J=8.6 Hz, 1H), 3.53 (d, J=8.6 Hz, 2H), 3.01 (d, J=5.1 Hz, 1H), 2.33 (s, 2H), 1.85-1.40 (m, 4H), 1.11 (d, J=6.4 Hz, 3H).

| Name | Shift | Range | H's | Integral | Class | J's |
|---|---|---|---|---|---|---|
| 1 A (d) | 1.11 | 1.18 ... 1.06 | 3 | 3.00 | d | 6.41 |
| 2 B (m) | 7.64 | 7.74 ... 7.53 | 2 | 1.99 | m | |
| 3 C (s) | 6.26 | 6.37 ... 6.21 | 2 | 2.01 | s | |
| 4 D (s) | 6.14 | 6.21 ... 6.01 | 2 | 2.01 | s | |
| 5 E (d) | 5.74 | 5.84 ... 5.66 | 1 | 1.01 | d | 5.35 |
| 6 F (m) | 4.09 | 4.19 ... 4.02 | 1 | 1.06 | m | |
| 7 G (t) | 3.91 | 4.02 ... 3.84 | 2 | 2.09 | t | 13.10, 13.10 |
| 8 H (d) | 3.72 | 3.77 ... 3.66 | 1 | 1.20 | d | 8.56 |
| 9 I (d) | 3.53 | 3.60 ... 3.51 | 2 | 1.57 | d | 8.59 |
| 10 J (d) | 3.01 | 3.04 ... 2.97 | 1 | 1.18 | d | 5.07 |
| 11 K (s) | 2.33 | 2.36 ... 2.27 | 2 | 2.37 | s | |
| 12 L (m) | 1.61 | 1.83 ... 1.38 | 4 | 4.17 | m | |

FIG. 7 shows an XRPD obtained.

Example 13

(3S,4S)-8-(6-amino-5-((2-amino-3-chloropyridin-4-yl)thio)pyrazin-2-yl)-3-methyl-2-oxa-8-azaspiro[4.5]decan-4-amine free base Modification A 12 g of (3S,4S)-8-(6-amino-5-((2-amino-3-chloropyridin-4-yl)thio)pyrazin-2-yl)-3-methyl-2-oxa-8-azaspiro[4.5]decan-4-amine was added into 150 mL of IPA. The mixture was stirred at 70° C. for 30 minutes to dissolved all of the solid. The mixture was cooled to 25° C. in 2 hours and stirred for another 1 hour. The solid was collected by vacuum filtration, dried unerder vacuum to afford the free form Modification A (10.4 g, 86.7%).

The free form showed strong degradation with an excipient mixture containing HPMC.

The following XRPD data were obtained (table of 2-theta values):

| Angle (2-theta) in deg. | d-value in Å | Rel. intensity in % |
|---|---|---|
| 9.5 | 9.27 | 10.0% |
| 12.3 | 7.20 | 14.8% |
| 14.2 | 6.22 | 21.9% |
| 15.6 | 5.68 | 43.8% |
| 16.5 | 5.35 | 100.0% |
| 18.8 | 4.71 | 47.5% |
| 21.3 | 4.17 | 34.8% |
| 22.3 | 3.98 | 28.5% |
| 23.0 | 3.86 | 17.8% |
| 24.7 | 3.60 | 42.7% |
| 25.6 | 3.48 | 53.4% |
| 28.7 | 3.11 | 16.1% |

$^1$H NMR (400 MHZ, DMSO-$d_6$) δ 7.72-7.54 (m, 2H), 6.25 (s, 2H), 6.12 (s, 2H), 5.74 (d, J=5.3 Hz, 1H), 4.06 (qd, J=6.4, 5.1 Hz, 1H), 3.83 (tt, J=13.2, 5.5 Hz, 2H), 3.66 (d, J=8.4 Hz, 1H), 3.48 (d, J=8.5 Hz, 1H), 3.44-3.22 (m, 3H), 2.90 (d, J=5.1 Hz, 1H), 1.72 (ddd, J=13.2, 9.3, 3.8 Hz, 1H), 1.62 (ddd, J=13.1, 9.0, 4.0 Hz, 1H), 1.48 (ddt, J=20.1, 13.2, 3.5 Hz, 2H), 1.08 (d, J=6.4 Hz, 3H).

| Name | Shift | Range | H's | Integral | Class | J's |
|---|---|---|---|---|---|---|
| 1 A (d) | 1.08 | 1.14 ... 1.00 | 3 | 3.00 | d | 6.40 |
| 2 B (m) | 7.63 | 7.72 ... 7.54 | 2 | 1.97 | m | |
| 3 C (s) | 6.25 | 6.33 ... 6.18 | 2 | 1.96 | s | |
| 4 D (s) | 6.12 | 6.18 ... 5.94 | 2 | 2.01 | s | |
| 5 E (d) | 5.74 | 5.83 ... 5.62 | 1 | 1.01 | d | 5.34 |
| 6 F (qd) | 4.06 | 4.20 ... 3.96 | 1 | 1.01 | qd | 5.06, 6.39, 6.43, 6.43 |
| 7 G (tt) | 3.83 | 3.91 ... 3.72 | 2 | 1.99 | tt | 5.54, 5.54, 13.18, 13.18 |
| 8 H (d) | 3.66 | 3.70 ... 3.62 | 1 | 1.01 | d | 8.44 |
| 9 I (d) | 3.48 | 3.52 ... 3.44 | 1 | 1.00 | d | 8.46 |
| 10 J (m) | 3.34 | 3.44 ... 3.22 | 3 | 3.10 | m | |
| 11 K (d) | 2.90 | 2.95 ... 2.86 | 1 | 0.98 | d | 5.12 |
| 12 L (ddd) | 1.72 | 1.79 ... 1.67 | 1 | 1.01 | ddd | 3.78, 9.27, 13.21 |
| 13 M (ddd) | 1.62 | 1.67 ... 1.55 | 1 | 1.06 | ddd | 3.96, 9.04, 13.10 |
| 14 N (ddt) | 1.48 | 1.56 ... 1.41 | 2 | 2.11 | ddt | 3.54, 3.54, 13.25, 20.11 |

FIG. 9 shows an XRPD obtained.

Example 14

(3S,4S)-8-(6-amino-5-((2-amino-3-chloropyridin-4-yl)thio)pyrazin-2-yl)-3-methyl-2-oxa-8-azaspiro[4.5]decan-4-amine, succinate (2:1), anhydrate, Modification A 1.0 g of (3S,4S)-8-(6-amino-5-((2-amino-3-chloropyridin-4-yl)thio)pyrazin-2-yl)-3-methyl-2-oxa-8-azaspiro[4.5]decan-4-amine monosuccinate, hydrate, Modification $H_A$ was added into a 20 mL glass vial and 5 mL of Methanol were added. The obtained mixture was stirred at 50° C. for one week. The mixture was filtered and dried to solid phase at ambient environment. This yields hemisuccinate, anhydrate, Modification A.

The following XRPD data were obtained (table of 2-theta values):

| Angle (2-theta) in deg. | d-value in Å | Rel. intensity in % |
|---|---|---|
| 4.9 | 18.17 | 30.3% |
| 11.4 | 7.73 | 17.4% |
| 12.1 | 7.30 | 18.7% |
| 13.3 | 6.64 | 36.7% |
| 16.4 | 5.38 | 68.9% |
| 17.0 | 5.21 | 57.6% |
| 17.8 | 4.97 | 31.0% |
| 19.6 | 4.53 | 100.0% |
| 20.6 | 4.30 | 67.3% |
| 22.7 | 3.91 | 20.6% |
| 23.5 | 3.78 | 61.8% |

$^1$H NMR (400 MHZ, DMSO-$d_6$) δ 7.77-7.51 (m, 2H), 6.26 (s, 2H), 6.14 (s, 2H), 5.74 (d, J=5.4 Hz, 1H), 4.22-3.99 (m, 1H), 3.91 (t, J=13.7 Hz, 2H), 3.72 (d, J=8.6 Hz, 1H), 3.54 (d, J=8.6 Hz, 2H), 3.02 (d, J=5.1 Hz, 1H), 2.34 (s, 3H), 1.86-1.39 (m, 4H), 1.11 (d, J=6.4 Hz, 3H).

| | Name | Shift | Range | H's | Integral | Class | J's |
|---|---|---|---|---|---|---|---|
| 1 | A (d) | 1.11 | 1.16 ... 1.02 | 3 | 3.00 | d | 6.45 |
| 2 | B (m) | 1.62 | 1.86 ... 1.39 | 4 | 4.06 | m | |
| 3 | C (s) | 2.34 | 2.39 ... 2.26 | 3 | 2.67 | s | |
| 4 | D (m) | 4.09 | 4.22 ... 3.99 | 1 | 1.08 | m | |
| 5 | E (t) | 3.91 | 4.00 ... 3.79 | 2 | 2.11 | t | 13.66, 13.66 |
| 6 | F (d) | 3.72 | 3.79 ... 3.68 | 1 | 1.21 | d | 8.59 |
| 7 | G (d) | 3.54 | 3.58 ... 3.49 | 2 | 1.77 | d | 8.61 |
| 8 | H (d) | 5.74 | 5.83 ... 5.66 | 1 | 0.97 | d | 5.38 |
| 9 | I (s) | 6.14 | 6.16 ... 6.04 | 2 | 1.77 | s | |
| 10 | J (s) | 6.26 | 6.37 ... 6.19 | 2 | 2.02 | s | |
| 11 | K (m) | 7.64 | 7.77 ... 7.51 | 2 | 1.89 | m | |
| 12 | L (d) | 3.02 | 3.07 ... 2.97 | 1 | 1.32 | d | 5.10 |

FIG. 8 shows an XRPD obtained.

Example 15

(3S,4S)-8-(6-amino-5-((2-amino-3-chloropyridin-4-yl)thio)pyrazin-2-yl)-3-methyl-2-oxa-8-azaspiro[4.5]decan-4-amine succinate (2:1), hydrate, modification $H_B$ The title compound is obtained during DVS from succinate (2:1) Modification $H_A$.

| Angle (2-theta) in deg. | d-value in Å | Rel. intensity in % |
|---|---|---|
| 4.8 | 18.29 | 62.3% |
| 11.6 | 7.61 | 28.4% |
| 12.1 | 7.28 | 58.3% |
| 13.3 | 6.65 | 33.9% |
| 16.4 | 5.38 | 64.9% |
| 17.0 | 5.21 | 55.1% |
| 19.6 | 4.54 | 100.0% |
| 20.6 | 4.31 | 69.7% |
| 23.6 | 3.77 | 59.3% |

Example 16

Comparison Different Forms of Examples 6 to 14

The succinate hemihydrate (Modification $H_A$) (Example 6) was chosen over its anhydrous form (Modification A) as the anhydrous form could be rapidly converted into Modification $H_A$ in aqueous organic solvent mixtures with very small quantities of water (1-2%), preventing the risk of form change during stability storage or tabletting. Further, Modification $H_A$ was chosen over the hemisuccinate forms as these were highly hygroscopic and showed a higher degree of polymorphism as Modification $H_A$.

Succinate Modification $H_A$ of Example 6 holds constant water content over 10% RH to 50% RH at room temperature. The succinate modification $H_A$ of Example 6 shows high solubility in aqueous media indicating potentially good bioavailability:

| Solvent | Solubility at 25° C., 24 h equilibration, target concentration = 2 mg/ml) in mg/mL (pH) |
|---|---|
| Borate buffer, pH 6.8 | 0.50 (pH 6.74) |
| Water | >2.00 (pH 5.52) |
| SGF, pH 2.0 | >2.00 (pH 2.61) |
| FaSSIF-V2, pH 6.5 | >2.00 (pH 5.93) |
| FeSSIF-V2, pH 5.8 | >2.00 (pH 5.66) |
| Phosphate buffer, pH 6.8 | 1.35 (pH 6.38) |

FaSSIF=Fasted State Simulated Intestinal Fluid (V2: sodium taurocholate 3 mM, lecithin 0.2 mM, sodium chloride 68.6 mM, maleic acid 19.1 mM, sodium hydroxide 101 mM, pancreatin 10.0 mg/l).

FeSSIF V2=Fed State Simulated Intestinal Fluid (V2: 10 mM sodium taurocholate, 2.0 mM lecithin, 0.8 mM sodium oleate, 5.0 mM glycerol monooleate, 125.5 mM sodium chloride, 81.7 mM sodium hydroxide, 55.0 mM maleic acid, pancreatin 40.0 mg/l).

SGF=Simulated Gastric Fluid (sodium chloride 2 g/l, triton X-100 1 g/l, HCl 0.1 M 100 ml/l.

At 50° C./75% RH, the succinate salt form $H_A$ showed acceptable degradation levels in all four experimental excipient mixtures when mixed with the following four excipients (the free form shows strong degradation with the mixture containing HPMC, the adipate salt with the mixture containing mannitol, Ac-di-Sol and microcrystalline cellulose);

Mixture 1: Gelatin powder
Mixture 2; HPMC
Mixture 3: MCC PH101 (45 wt-%); lactose monohydate (44 wt-%), PVP K30 (4 wt-%), Aerosil (0.5 wt-%), Mg stearate (1.5 wt-%), then 20 wt-% water added to the mixture.
Mixture 4: Mannitol DC (68.7 wt-%), MCC PH102 (26 wt-%), Ac-di-Sol (4 wt-%), Acrosil (0.3 wt-%), Mg stearate (1 wt-%).

The invention claimed is:

1. A compound, wherein said compound is (3S,4S)-8-(6-amino-5-((2-amino-3-chloropyridin-4-yl)thio)pyrazin-2-yl)-3-methyl-2-oxa-8-azaspiro[4.5]decan-4-amine monosuccinate salt, or a hydrate thereof, in crystalline form.

2. The compound of claim 1 which is (3S,4S)-8-(6-amino-5-((2-amino-3-chloropyridin-4-yl)thio)pyrazin-2-yl)-3-methyl-2-oxa-8-azaspiro[4.5]decan-4-amine monosuccinate hydrate.

3. The compound of claim 1 which is (3S,4S)-8-(6-amino-5-((2-amino-3-chloropyridin-4-yl)thio)pyrazin-2-yl)-3-methyl-2-oxa-8-azaspiro[4.5]decan-4-amine, succinate (1:1) in anhydrous form.

4. The compound of claim 1 which is (3S,4S)-8-(6-amino-5-((2-amino-3-chloropyridin-4-yl)thio)pyrazin-2-yl)-3-methyl-2-oxa-8-azaspiro[4.5]decan-4-amine, succinate (2:1) hydrate.

5. The compound of claim 1 which is (3S,4S)-8-(6-amino-5-((2-amino-3-chloropyridin-4-yl)thio)pyrazin-2-yl)-3-methyl-2-oxa-8-azaspiro[4.5]decan-4-amine, succinate (2:1) anhydrate.

6. A pharmaceutical composition comprising the compound of claim 1 and at least one pharmaceutically acceptable carrier.

7. The composition according to claim 6, wherein the compound is (3S,4S)-8-(6-amino-5-((2-amino-3-chloropyridin-4-yl)thio)pyrazin-2-yl)-3-methyl-2-oxa-8-azaspiro[4.5]decan-4-amine succinate (1:1) hydrated form $H_A$.

8. A method of treatment comprising administering the compound of claim 1 to a patient in need of such treatment in an effective amount for the prophylactic or therapeutic treatment of a disease or disorder which is mediated by the activity of SHP2.

9. The method of claim 8, wherein the disease or disorder mediated by the activity of SHP2 is selected from Noonan Syndrome, Leopard Syndrome, juvenile myelomonocytic leukemias, neuroblastoma, melanoma, acute myeloid leukemia, breast cancer, esophageal cancer, lung cancer, colon cancer, head cancer, neuroblastoma, squamous-cell carcinoma of the head and neck, gastric carcinoma, anaplastic large-cell lymphoma and glioblastoma.

10. A combination comprising the compound of claim 1, and one or more other pharmacologically active compounds for simultaneous, sequential or separate administration.

11. The combination of claim 10, wherein the one or more other pharmacologically active compounds is an antiproliferative agent.

12. The compound of claim 2, characterized by an XRPD pattern with at least three of the following 2-theta values; 8.1°, 16.3°, 17.5°, 22.5° and 26.8°.

13. The compound of claim 2, characterized by an XRPD pattern substantially as shown in FIG. 1.

14. The compound of claim 2, in form $H_A$.

* * * * *